(12) United States Patent
Babayoff

(10) Patent No.: US 10,944,953 B2
(45) Date of Patent: Mar. 9, 2021

(54) METHOD AND APPARATUS FOR COLOUR IMAGING A THREE-DIMENSIONAL STRUCTURE

(71) Applicant: ALIGN TECHNOLOGY, INC., San Jose, CA (US)

(72) Inventor: Noam Babayoff, Rishon Le Zion (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 16/427,101

(22) Filed: May 30, 2019

(65) Prior Publication Data

US 2019/0281272 A1 Sep. 12, 2019

Related U.S. Application Data

(63) Continuation of application No. 16/270,419, filed on Feb. 7, 2019, which is a continuation of application
(Continued)

(51) Int. Cl.
*H04N 13/15* (2018.01)
*G01B 11/25* (2006.01)
(Continued)

(52) U.S. Cl.
CPC ......... *H04N 13/15* (2018.05); *A61B 1/00009* (2013.01); *A61B 1/00096* (2013.01);
(Continued)

(58) Field of Classification Search
None
See application file for complete search history.

(56) References Cited

U.S. PATENT DOCUMENTS

| 2,467,432 A | 4/1949 | Kesling et al. |
| 2,531,222 A | 11/1950 | Kesling |

(Continued)

FOREIGN PATENT DOCUMENTS

| AU | 3031677 A | 5/1979 |
| AU | 517102 B2 | 7/1981 |

(Continued)

OTHER PUBLICATIONS

Cha et al.: Nontranslational Three-Dimensional Profilometry by Chromatic Confocal Microscopy with Dynamically Configurable Micromirror Scanning. Appl Opt. 39(16): 2605-2613 (2000).
(Continued)

*Primary Examiner* — Rebecca A Volentine
(74) *Attorney, Agent, or Firm* — FisherBroyles, LLP

(57) ABSTRACT

A device for determining the surface topology and associated color of a structure, such as a teeth segment, includes a scanner for providing depth data for points along a two-dimensional array substantially orthogonal to the depth direction, and an image acquisition means for providing color data for each of the points of the array, while the spatial disposition of the device with respect to the structure is maintained substantially unchanged. A processor combines the color data and depth data for each point in the array, thereby providing a three-dimensional color virtual model of the surface of the structure. A corresponding method for determining the surface topology and associate color of a structure is also provided.

29 Claims, 18 Drawing Sheets

Related U.S. Application Data

No. 15/175,267, filed on Jun. 7, 2016, which is a continuation of application No. 14/755,171, filed on Jun. 30, 2015, now Pat. No. 9,404,740, which is a continuation of application No. 14/511,091, filed on Oct. 9, 2014, now Pat. No. 9,101,433, which is a continuation of application No. 14/150,505, filed on Jan. 8, 2014, now Pat. No. 8,885,175, which is a continuation of application No. 13/868,926, filed on Apr. 23, 2013, now Pat. No. 8,675,207, which is a continuation of application No. 13/620,159, filed on Sep. 14, 2012, now Pat. No. 8,451,456, which is a continuation of application No. 13/333,351, filed on Dec. 21, 2011, now Pat. No. 8,363,228, which is a continuation of application No. 12/770,379, filed on Apr. 29, 2010, now Pat. No. 8,102,538, which is a continuation of application No. 12/379,343, filed on Feb. 19, 2009, now Pat. No. 7,724,378, which is a continuation of application No. 11/889,112, filed on Aug. 9, 2007, now Pat. No. 7,511,829, which is a continuation of application No. 11/154,520, filed on Jun. 17, 2005, now Pat. No. 7,319,529.

(60) Provisional application No. 60/580,109, filed on Jun. 17, 2004, provisional application No. 60/580,108, filed on Jun. 17, 2004.

(51) Int. Cl.

| | | |
|---|---|---|
| *H04N 13/207* | (2018.01) | |
| *H04N 13/257* | (2018.01) | |
| *H04N 13/271* | (2018.01) | |
| *H04N 13/296* | (2018.01) | |
| *A61B 1/00* | (2006.01) | |
| *A61B 1/06* | (2006.01) | |
| *A61B 1/24* | (2006.01) | |
| *A61B 1/247* | (2006.01) | |
| *A61B 5/00* | (2006.01) | |
| *A61B 5/107* | (2006.01) | |
| *G01B 11/24* | (2006.01) | |
| *G01J 3/02* | (2006.01) | |
| *G01J 3/10* | (2006.01) | |
| *G01J 3/50* | (2006.01) | |
| *G06T 7/12* | (2017.01) | |
| *G06T 7/90* | (2017.01) | |
| *A61C 9/00* | (2006.01) | |
| *G06T 7/00* | (2017.01) | |
| *G01N 21/25* | (2006.01) | |
| *H01L 27/148* | (2006.01) | |
| *A61C 19/04* | (2006.01) | |
| *G01J 3/46* | (2006.01) | |
| *G01J 3/51* | (2006.01) | |

(52) U.S. Cl.
CPC .......... *A61B 1/0615* (2013.01); *A61B 1/0638* (2013.01); *A61B 1/0646* (2013.01); *A61B 1/0676* (2013.01); *A61B 1/0684* (2013.01); *A61B 1/24* (2013.01); *A61B 1/247* (2013.01); *A61B 5/0068* (2013.01); *A61B 5/0088* (2013.01); *A61B 5/1077* (2013.01); *A61B 5/1079* (2013.01); *A61C 9/0053* (2013.01); *A61C 9/0066* (2013.01); *A61C 19/04* (2013.01); *G01B 11/24* (2013.01); *G01B 11/25* (2013.01); *G01J 3/02* (2013.01); *G01J 3/0205* (2013.01); *G01J 3/0208* (2013.01); *G01J 3/0216* (2013.01); *G01J 3/0218* (2013.01); *G01J 3/0224* (2013.01); *G01J 3/0243* (2013.01); *G01J 3/0256* (2013.01); *G01J 3/10* (2013.01); *G01J 3/50* (2013.01); *G01J 3/501* (2013.01); *G01J 3/508* (2013.01); *G01N 21/255* (2013.01); *G06T 7/0012* (2013.01); *G06T 7/12* (2017.01); *G06T 7/90* (2017.01); *H01L 27/14868* (2013.01); *H04N 13/207* (2018.05); *H04N 13/257* (2018.05); *H04N 13/271* (2018.05); *H04N 13/296* (2018.05); *G01J 3/462* (2013.01); *G01J 3/51* (2013.01); *G06T 2207/10024* (2013.01); *G06T 2207/10028* (2013.01); *G06T 2207/30036* (2013.01)

(56) References Cited

U.S. PATENT DOCUMENTS

| | | |
|---|---|---|
| 2,779,470 A | 1/1957 | Walters |
| 3,013,467 A | 12/1961 | Marvin et al. |
| 3,407,500 A | 10/1968 | Kesling et al. |
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,971,065 A | 7/1976 | Bayer |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,349,277 A | 9/1982 | Mundy |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,629,324 A | 12/1986 | Stern |
| 4,640,620 A | 2/1987 | Schmidt |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,727,416 A | 2/1988 | Cooper |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,802,846 A | 2/1989 | Posca |
| 4,836,674 A | 6/1989 | Lequime et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,895,431 A | 1/1990 | Tsujiuchi |
| 4,935,635 A | 6/1990 | O'Harra |
| 4,936,862 A | 6/1990 | Walker et al. |
| 4,937,928 A | 7/1990 | Van Der Zel et al. |
| 4,941,826 A | 7/1990 | Loran et al. |
| 4,964,770 A | 10/1990 | Steinbichler et al. |

(56) References Cited

U.S. PATENT DOCUMENTS

| | | |
|---|---|---|
| 4,975,052 A | 12/1990 | Spencer et al. |
| 4,983,120 A | 1/1991 | Coleman |
| 4,983,334 A | 1/1991 | Adell et al. |
| 5,003,166 A | 3/1991 | Girod |
| 5,008,743 A | 4/1991 | Katzir |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,151,609 A | 9/1992 | Nakagawa |
| 5,151,856 A | 9/1992 | Halmann |
| 5,155,558 A | 10/1992 | Tannenbaum |
| 5,168,386 A | 12/1992 | Galbraith |
| 5,176,517 A | 1/1993 | Truax et al. |
| 5,177,556 A | 1/1993 | Rioux |
| 5,184,306 A | 2/1993 | Erdman et al. |
| 5,186,623 A | 2/1993 | Breads et al. |
| 5,193,124 A | 3/1993 | Subbarao |
| 5,239,178 A | 8/1993 | Derndinger |
| 5,257,203 A | 10/1993 | Riley et al. |
| 5,273,429 A | 12/1993 | Rekow et al. |
| 5,278,756 A | 1/1994 | Lemchen et al. |
| 5,305,430 A | 4/1994 | Glassner |
| 5,306,144 A | 4/1994 | Hibst |
| 5,328,362 A | 7/1994 | Watson et al. |
| 5,338,198 A | 8/1994 | Wu et al. |
| 5,339,154 A | 8/1994 | Gassler |
| 5,340,309 A | 8/1994 | Robertson et al. |
| 5,342,202 A | 8/1994 | Deshayes et al. |
| 5,363,159 A | 11/1994 | Melvin |
| 5,368,478 A | 11/1994 | Andreiko et al. |
| 5,372,502 A | 12/1994 | Massen et al. |
| 5,381,224 A | 1/1995 | Dixon |
| 5,381,236 A | 1/1995 | Morgan et al. |
| 5,382,164 A | 1/1995 | Stern et al. |
| 5,395,238 A | 3/1995 | Andreiko et al. |
| 5,417,572 A | 5/1995 | Kawai |
| 5,431,562 A | 7/1995 | Andreiko et al. |
| 5,440,326 A | 8/1995 | Quinn et al. |
| 5,440,393 A | 8/1995 | Wenz et al. |
| 5,440,496 A | 8/1995 | Andersson et al. |
| 5,447,432 A | 9/1995 | Andreiko et al. |
| 5,448,472 A | 9/1995 | Mushabac |
| 5,452,219 A | 9/1995 | Dehoff et al. |
| 5,454,717 A | 10/1995 | Andreiko et al. |
| 5,455,899 A | 10/1995 | Forslund |
| 5,456,600 A | 10/1995 | Andreiko et al. |
| 5,458,487 A | 10/1995 | Komatsu |
| 5,474,448 A | 12/1995 | Andreiko et al. |
| 5,495,429 A | 2/1996 | Craven |
| RE35,169 E | 3/1996 | Lemchen et al. |
| 5,512,036 A | 4/1996 | Tamburrino |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,606,459 A | 2/1997 | Nakatsuji |
| 5,607,305 A | 3/1997 | Andersson et al. |
| 5,608,529 A | 3/1997 | Hori |
| 5,614,075 A | 3/1997 | Andre, Sr. et al. |
| 5,615,003 A | 3/1997 | Hermary |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,659,420 A | 8/1997 | Wakai |
| 5,661,519 A | 8/1997 | Franetzki |
| 5,675,380 A | 10/1997 | Florent |
| 5,675,407 A | 10/1997 | Geng |
| 5,683,243 A | 11/1997 | Andreiko et al. |
| 5,690,486 A | 11/1997 | Zigelbaum |
| 5,692,894 A | 12/1997 | Schwartz et al. |
| 5,702,249 A | 12/1997 | Cooper |
| 5,725,376 A | 3/1998 | Poirier et al. |
| 5,725,378 A | 3/1998 | Wang et al. |
| 5,730,151 A | 3/1998 | Summer |
| 5,733,126 A | 3/1998 | Andersson et al. |
| 5,737,084 A | 4/1998 | Ishihara |
| 5,737,121 A | 4/1998 | Dixon |
| 5,740,267 A | 4/1998 | Echerer et al. |
| 5,742,700 A | 4/1998 | Yoon et al. |
| 5,743,730 A | 4/1998 | Clester |
| 5,749,830 A | 5/1998 | Kaneko et al. |
| 5,754,298 A | 5/1998 | Falk |
| 5,759,030 A | 6/1998 | Jung |
| 5,766,006 A | 6/1998 | Murljacic et al. |
| 5,784,098 A | 7/1998 | Shoji |
| 5,788,639 A | 8/1998 | Zavislan |
| 5,793,900 A | 8/1998 | Nourbakhsh |
| 5,799,100 A | 8/1998 | Clarke et al. |
| 5,800,164 A | 9/1998 | Pfau |
| 5,800,174 A | 9/1998 | Andersson et al. |
| 5,823,778 A | 10/1998 | Schmitt et al. |
| 5,847,832 A | 12/1998 | Liskow et al. |
| 5,848,115 A | 12/1998 | Little et al. |
| 5,857,853 A | 1/1999 | Van Nifterick et al. |
| 5,864,640 A | 1/1999 | Miramonti et al. |
| 5,866,058 A | 2/1999 | Batchelder et al. |
| 5,878,152 A | 3/1999 | Sussman |
| 5,879,158 A | 3/1999 | Doyle et al. |
| 5,880,826 A | 3/1999 | Jung |
| 5,880,961 A | 3/1999 | Crump et al. |
| 5,880,962 A | 3/1999 | Andersson et al. |
| 5,912,735 A | 6/1999 | Xu |
| 5,934,288 A | 8/1999 | Avila et al. |
| 5,951,475 A | 9/1999 | Gueziec |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,007,332 A | 12/1999 | O'Brien |
| 6,015,289 A | 1/2000 | Andreiko et al. |
| 6,019,721 A | 2/2000 | Holmes |
| 6,026,172 A | 2/2000 | Lewis, Jr. |
| 6,030,209 A | 2/2000 | Panzera |
| 6,033,222 A | 3/2000 | Schneider, II |
| 6,044,309 A | 3/2000 | Honda et al. |
| 6,049,743 A | 4/2000 | Baba et al. |
| 6,057,909 A | 5/2000 | Yahav |
| 6,059,721 A | 5/2000 | Rudischhauser |
| 6,061,091 A | 5/2000 | Van De Poel |
| 6,062,861 A | 5/2000 | Andersson |
| 6,068,482 A | 5/2000 | Snow et al. |
| 6,081,739 A | 6/2000 | Lemchen |
| 6,097,854 A | 8/2000 | Szeliski |
| 6,099,314 A | 8/2000 | Kopelman et al. |
| 6,118,521 A | 9/2000 | Jung |
| 6,123,544 A | 9/2000 | Cleary |
| 6,137,893 A | 10/2000 | Michael |
| 6,148,120 A | 11/2000 | Sussman |
| 6,152,731 A | 11/2000 | Jordan et al. |
| 6,179,611 B1 * | 1/2001 | Everett ............... A61B 5/0088 433/29 |
| 6,181,474 B1 | 1/2001 | Ouderkirk |
| 6,183,248 B1 | 2/2001 | Chishti et al. |
| 6,190,165 B1 | 2/2001 | Andreiko et al. |
| 6,190,170 B1 | 2/2001 | Morris |
| 6,205,243 B1 | 3/2001 | Migdal et al. |
| 6,208,788 B1 | 3/2001 | Nosov |

(56) References Cited

U.S. PATENT DOCUMENTS

| | | |
|---|---|---|
| 6,217,325 B1 | 4/2001 | Chishti et al. |
| 6,217,334 B1 | 4/2001 | Hultgren et al. |
| 6,219,461 B1 | 4/2001 | Wallack |
| 6,222,174 B1 | 4/2001 | Tullis |
| 6,229,913 B1 | 5/2001 | Nayar |
| 6,238,567 B1 | 5/2001 | Van De Moortele |
| 6,244,861 B1 | 6/2001 | Andreiko et al. |
| 6,246,479 B1 | 6/2001 | Jung |
| 6,262,738 B1 | 7/2001 | Gibson |
| 6,263,233 B1 | 7/2001 | Zavislan et al. |
| 6,263,234 B1 | 7/2001 | Engelhardt et al. |
| 6,276,934 B1 | 8/2001 | Rakocz |
| 6,281,931 B1 | 8/2001 | Tsao |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,362,888 B1 | 3/2002 | Jung |
| 6,376,818 B1 | 4/2002 | Wilson |
| 6,377,298 B1 | 4/2002 | Scheele |
| 6,379,593 B1 | 4/2002 | Datzmann |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,414,750 B2 | 7/2002 | Jung |
| 6,417,917 B1 | 7/2002 | Jung |
| 6,420,698 B1 | 7/2002 | Dimsdale |
| 6,450,949 B1 | 9/2002 | Farkas |
| 6,477,403 B1 | 11/2002 | Eglichi |
| 6,482,298 B1 | 11/2002 | Bhatnagar et al. |
| 6,511,183 B2 | 1/2003 | Shimizu |
| 6,519,037 B2 | 2/2003 | Jung |
| 6,519,359 B1 | 2/2003 | Nafis |
| 6,522,777 B1 | 2/2003 | Paulsen |
| 6,524,101 B1 | 2/2003 | Phan et al. |
| 6,525,819 B1 | 2/2003 | Delawter et al. |
| 6,525,828 B1 | 2/2003 | Grosskopf et al. |
| 6,530,882 B1 | 3/2003 | Farkas |
| 6,538,726 B2 | 3/2003 | Dejung |
| 6,549,288 B1 | 4/2003 | Migdal et al. |
| 6,554,611 B2 | 4/2003 | Shishti et al. |
| 6,570,654 B2 | 5/2003 | Jung |
| 6,572,372 B1 | 6/2003 | Phan et al. |
| 6,573,984 B2 | 6/2003 | Jung |
| 6,575,751 B1 | 6/2003 | Lehmann et al. |
| 6,577,405 B2 | 6/2003 | Kranz |
| 6,594,539 B1 | 7/2003 | Geng |
| 6,614,539 B1 | 9/2003 | Shimizu |
| 6,621,491 B1 | 9/2003 | Baumrind |
| 6,629,840 B2 | 10/2003 | Chishti et al. |
| 6,648,640 B2 | 11/2003 | Rubbert |
| 6,697,162 B1 | 2/2004 | Sakai |
| 6,697,164 B1 | 2/2004 | Babayoff et al. |
| 6,705,863 B2 | 3/2004 | Phan et al. |
| 6,722,880 B2 | 4/2004 | Chishti et al. |
| 6,739,869 B1 | 5/2004 | Taub |
| 6,750,873 B1 | 6/2004 | Bernardini |
| 6,765,606 B1 | 7/2004 | Iddan |
| 6,769,769 B2 | 8/2004 | Podoleanu |
| 6,788,210 B1 | 9/2004 | Huang |
| 6,788,338 B1 | 9/2004 | Dinev |
| 6,816,625 B2 | 11/2004 | Lewis, Jr. |
| 6,819,318 B1 | 11/2004 | Geng |
| 6,845,175 B2 | 1/2005 | Kopelman |
| 6,937,348 B2 | 8/2005 | Geng |
| 6,947,582 B1 | 9/2005 | Vilsmeier |
| 6,958,766 B2 | 10/2005 | Cooper |
| 6,962,289 B2 | 11/2005 | Vatan |
| 6,977,732 B2 | 12/2005 | Chen |
| 7,010,223 B2 | 3/2006 | Thoms |
| 7,012,700 B2 | 3/2006 | De Groot |
| 7,013,191 B2 | 3/2006 | Rubbert |
| 7,062,311 B1 | 6/2006 | Sendai |
| 7,064,830 B2 | 6/2006 | Giorgianni |
| 7,068,825 B2 | 6/2006 | Rubbert |
| 7,069,186 B2 | 6/2006 | Jung |
| 7,078,720 B2 | 7/2006 | Yamaguchi |
| 7,086,863 B2 | 8/2006 | Van Der Zel |
| 7,098,435 B2 | 8/2006 | Mueller et al. |
| 7,099,732 B2 | 8/2006 | Geng |
| 7,110,124 B2 | 9/2006 | Jensen |
| 7,110,594 B2 | 9/2006 | Jones |
| 7,142,312 B2 | 11/2006 | Quadling |
| 7,160,110 B2 | 1/2007 | Imgrund |
| 7,161,741 B1 | 1/2007 | Schaack |
| 7,166,537 B2 | 1/2007 | Jacobsen |
| 7,205,531 B2 | 4/2007 | Watanabe |
| 7,230,725 B2 | 6/2007 | Babayoff |
| 7,296,996 B2 | 11/2007 | Sachdeva |
| 7,305,121 B2 | 12/2007 | Kaufmann |
| 7,319,529 B2 | 1/2008 | Babayoff |
| 7,383,094 B2 | 6/2008 | Kopelman |
| 7,397,505 B2 | 7/2008 | Brehmer |
| 7,446,885 B2 | 11/2008 | Zabolitzky |
| 7,456,842 B2 | 11/2008 | Kosolapov |
| 7,474,307 B2 | 1/2009 | Chishti |
| 7,494,338 B2 | 2/2009 | Durbin |
| 7,495,778 B2 | 2/2009 | Sieckmann |
| 7,511,829 B2 | 3/2009 | Babayoff et al. |
| 7,538,774 B2 | 5/2009 | Kunita |
| 7,625,335 B2 | 12/2009 | Deichmann |
| 7,630,538 B2 | 12/2009 | Nishiyama |
| 7,679,723 B2 | 3/2010 | Schwotzer |
| 7,698,068 B2 | 4/2010 | Babayoff |
| 7,724,378 B2 | 5/2010 | Babayoff et al. |
| 7,751,871 B2 | 7/2010 | Rubbert |
| 7,756,327 B2 | 7/2010 | Komiya |
| 7,762,814 B2 | 7/2010 | Van Der Zel |
| 7,936,392 B2 | 5/2011 | Ng |
| 8,102,538 B2 | 1/2012 | Babayoff |
| 8,363,228 B2 | 1/2013 | Babayoff |
| 8,400,635 B2 | 3/2013 | Inglese |
| 8,451,456 B2 | 5/2013 | Babayoff |
| 8,537,204 B2 | 9/2013 | Cho |
| 8,675,207 B2 | 3/2014 | Babayoff |
| 8,885,175 B2 | 11/2014 | Babayoff |
| 9,101,433 B2 | 8/2015 | Babayoff |
| 9,404,740 B2 | 8/2016 | Babayoff et al. |
| 2001/0046317 A1 | 11/2001 | Kamon |
| 2002/0006217 A1 | 1/2002 | Rubbert |
| 2002/0006597 A1 | 1/2002 | Andreiko et al. |
| 2002/0010568 A1 | 1/2002 | Rubbert |
| 2002/0028418 A1 | 3/2002 | Farag et al. |
| 2002/0050988 A1 | 5/2002 | Petrov et al. |
| 2002/0057438 A1 | 5/2002 | Decker |
| 2002/0091402 A1 | 7/2002 | Feinsod |
| 2002/0100884 A1 | 8/2002 | Maddock |
| 2003/0009252 A1 | 1/2003 | Pavlovskaia et al. |
| 2003/0026469 A1 | 2/2003 | Kreang-Arekul et al. |
| 2003/0031596 A1 | 2/2003 | Tanaami |
| 2003/0071194 A1 | 4/2003 | Mueller et al. |
| 2003/0107747 A1 | 6/2003 | Iwasaki |
| 2003/0139834 A1 | 7/2003 | Nikolskiy et al. |
| 2003/0198384 A1 | 10/2003 | Vrhel |
| 2003/0219148 A1 | 11/2003 | Scharlack |
| 2003/0224311 A1 | 12/2003 | Cronauer et al. |
| 2003/0231793 A1 | 12/2003 | Crampton |
| 2004/0027450 A1 | 2/2004 | Yoshino |
| 2004/0029068 A1 | 2/2004 | Sachdeva et al. |
| 2004/0107080 A1 | 6/2004 | Deichmann et al. |
| 2004/0125205 A1 | 7/2004 | Geng |
| 2004/0128010 A1 | 7/2004 | Pavlovskaia et al. |
| 2004/0165097 A1 | 8/2004 | Drowley |
| 2004/0197727 A1 | 10/2004 | Sachdeva |
| 2004/0254476 A1 | 12/2004 | Quadling et al. |
| 2005/0055118 A1 | 3/2005 | Nikolskiy et al. |
| 2005/0088529 A1 | 4/2005 | Geng |
| 2005/0089213 A1 | 4/2005 | Geng |
| 2005/0128196 A1 | 6/2005 | Popescu et al. |
| 2005/0225849 A1 | 10/2005 | Gouch |
| 2005/0243330 A1 | 11/2005 | Magarill |
| 2005/0283065 A1 | 12/2005 | Babayoff |
| 2006/0017720 A1 | 1/2006 | Li |
| 2006/0025692 A1 | 2/2006 | Ishihara |

(56) References Cited

U.S. PATENT DOCUMENTS

| | | |
|---|---|---|
| 2006/0087645 A1 | 4/2006 | Davidson-Sokal |
| 2006/0098213 A1 | 5/2006 | Itoh |
| 2006/0103854 A1 | 5/2006 | Franke |
| 2006/0245187 A1 | 11/2006 | Scott |
| 2007/0035641 A1 | 2/2007 | Yamada |
| 2007/0194214 A1 | 8/2007 | Pfeiffer |
| 2008/0082000 A1 | 4/2008 | Thoms |
| 2008/0280258 A1 | 11/2008 | Wen |
| 2011/0199606 A1 | 8/2011 | Jung |
| 2012/0092678 A1 | 4/2012 | Babayoff |
| 2013/0070985 A1 | 3/2013 | Babayoff |
| 2013/0243284 A1 | 9/2013 | Babayoff |
| 2014/0119622 A1 | 5/2014 | Babayoff |
| 2015/0022824 A1 | 1/2015 | Babayoff |
| 2015/0164335 A1* | 6/2015 | Van Der Poel ...... A61C 9/0053 433/29 |
| 2015/0297329 A1* | 10/2015 | Babayoff ........... A61B 1/00009 433/29 |
| 2016/0295191 A1 | 10/2016 | Babayoff et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 19883810455 | 10/1989 |
| DE | 19904034007 | 4/1992 |
| DE | 1995136297 | 4/1997 |
| DE | 19636354 A1 | 3/1998 |
| DE | 1997149974 | 5/1999 |
| DE | 69327661 T2 | 7/2000 |
| DE | 19922870 A1 | 12/2000 |
| DE | 1999155702 | 5/2001 |
| DE | 2003128040 | 1/2005 |
| DE | 2003156412 | 6/2005 |
| EP | 0091876 A1 | 10/1983 |
| EP | 0299490 A2 | 1/1989 |
| EP | 0360657 A1 | 3/1990 |
| EP | 0367647 A1 | 5/1990 |
| EP | 0376873 A2 | 7/1990 |
| EP | 0490848 A2 | 6/1992 |
| EP | 0541500 A1 | 5/1993 |
| EP | 0607295 | 7/1994 |
| EP | 0665686 | 8/1995 |
| EP | 0837659 A1 | 4/1998 |
| EP | 0667753 B1 | 1/2000 |
| EP | 1041378 | 10/2000 |
| EP | 0774933 B1 | 12/2000 |
| EP | 0731673 B1 | 5/2001 |
| EP | 1256831 | 11/2002 |
| EP | 1301140 | 4/2003 |
| EP | 1596158 | 11/2005 |
| ES | 463897 A1 | 1/1980 |
| FR | 2369828 A1 | 6/1978 |
| FR | 2652256 A1 | 3/1991 |
| FR | 2707018 | 12/1994 |
| FR | 2758076 | 7/1998 |
| GB | 1550777 A | 8/1979 |
| JP | S5358191 A | 5/1978 |
| JP | S5596406 | 7/1980 |
| JP | H0428359 A | 1/1992 |
| JP | 3321866 | 7/1994 |
| JP | 06201337 | 7/1994 |
| JP | H03063507 | 7/1994 |
| JP | 08508174 | 9/1996 |
| JP | H08508174 A | 9/1996 |
| JP | H0926312 | 1/1997 |
| JP | H09304685 | 11/1997 |
| JP | H10239023 | 9/1998 |
| JP | 200182935 | 3/2001 |
| JP | 2001066112 | 3/2001 |
| JP | 2001074422 | 3/2001 |
| JP | 2001082935 A | 3/2001 |
| JP | 2004029537 | 1/2004 |
| JP | 2004062093 | 2/2004 |
| JP | 2004226072 | 8/2004 |
| JP | 2004294097 | 10/2004 |
| JP | 2005279028 | 10/2005 |
| KR | 100765300 | 10/2007 |
| WO | WO-8911260 A1 | 11/1989 |
| WO | WO-9008512 A1 | 8/1990 |
| WO | 9103988 | 4/1991 |
| WO | WO-9104713 A1 | 4/1991 |
| WO | WO-9410935 A1 | 5/1994 |
| WO | 9703622 | 2/1997 |
| WO | 9829708 | 7/1998 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |
| WO | 0066972 | 11/2000 |
| WO | 0069358 | 11/2000 |
| WO | 0070303 | 11/2000 |
| WO | 02056756 | 7/2002 |
| WO | WO-02056756 A2 | 7/2002 |
| WO | 03052347 | 6/2003 |
| WO | 03060587 | 7/2003 |
| WO | 03094102 | 11/2003 |
| WO | WO-03105289 A2 | 12/2003 |
| WO | 2004008981 A2 | 1/2004 |
| WO | 2005059470 | 6/2005 |
| WO | WO-2010145669 A1 | 12/2010 |

OTHER PUBLICATIONS

Dixon et al.: A New Confocal Scanning Beam Laser MACROscope Using a Telecentric, F-Theta Laser Scan Lens. J. Microscopy 178(3): 261-266 (1995).
H. Hugli et al., "Object Modeling by Geometric Matching for a Prospective Portable 3D Scanner," Proceedings Neuchatel COST 254 Workshop 67-70, 1999, pp. 1-5.
Ishihara et al., "High-speed 3D shape measurement using a non-scanning multiple-beam confocal imaging system," SPIE, 1998, pp. 68-75, vol. 3478.
K. Omasa et al., "3-D Color Video Microscopy of Intact Plants: A New Method for Measuring Shape and Growth," Environ. Control in Biol., 36(4), 217-226 (1998).
Kozubek et al.: An Efficient Algorithm for Measurement and Correction of Chromatic Aberrations in Fluorescence Microscopy. Journal of Microscopy 200(Pt 3): 206-217. (2000).
Liang et al.: Confocal Pattern Period in Multiple-Aperture Confocal Imaging Systems with Coherent Illumination. Opt Lett. 22(1): 751-753(1997).
M. Niederoest et al., "Shape from Focus: Fully Automated 3D Reconstruction and Visualization of Microscopic Objects," ETH Zurich Research Collection, pp. 4-11 (2003).
Paddock et al.: Methods and Applications of Three-Color Confocal Imaging. Biotechniques. 22(1): 120-126 (1997).
Subbarao et al.: Depth from Defocus: A Spatial Domain Approach. International Journal of Computer Vision 13(3): 271-294 (1994).
Tiziani H. J. et al., Confocal principle for macro—and microscopic surface and defect analysis. Optical Engineering, vol. 39.1 (Jan. 1, 2000), pp. 32-39. Society of Photo-Optical Instrumentation Engineers.
Tiziani, et al., "Three-dimensional analysis by a microlens-array confocal arrangement," Applied Optics, 1994, pp. 567-572, vol. 33 (4).
Tiziani, et al., "Three-dimensional image sensing by chromatic confocal microscopy," Applied Optics, 1994, pp. 1838-1843, vol. 33 (10).
Tiziani, H. J., et al., "Theoretical analysis of confocal microscopy with microlenses," Applied Optics 35(1):120-25 (1996).
Watanabe et al.: Real-Time Computation of Depth from Defocus. Hitachi Ltd., Production Engineering Research Lab, 292 Yoshida-cho, Totsuka, Yokohama 244, Japan. Columbia University, Department of Computer Science New York, NY 10027.12 pages.
Institution Decision, *3SHAPE A/S v. Align Technology, Inc.*, IPR2019-00154, Paper No. 8, (P.T.A.B. Jun. 5, 2019).

(56) References Cited

OTHER PUBLICATIONS

Institution Decision, *3SHAPE A/S v. Align Technology, Inc.*, IPR2019-00155, Paper No. 9, (P.T.A.B. Jun. 7, 2019).
Institution Decision, *3SHAPE A/S v. Align Technology, Inc.*, IPR2019-00156, Paper No. 9, (P.T.A.B. Jun. 11, 2019).
Institution Decision, *3SHAPE A/S v. Align Technology, Inc.*, IPR2019-00157, Paper No. 9, (P.T.A.B. Jun. 5, 2019).
Institution Decision, *3SHAPE A/S v. Align Technology, Inc.*, IPR2019-00159, Paper No. 9, (P.T.A.B. Jun. 7, 2019).
Institution Decision, *3SHAPE A/S v. Align Technology, Inc.*, IPR2019-00160, Paper No. 9, (P.T.A.B. Jun. 11, 2019).
Institution Decision, *3SHAPE A/S v. Align Technology, Inc.*, IPR2019-00163, Paper No. 8, (P.T.A.B. Jun. 11, 2019).
AADR. American Association for Dental Research, Summary of Activities, Mar. 20-23, 1980, Los Angeles, CA, p. 195.
Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures, " IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Cha, et al. 3D profilometry using a dynamically configurable confocal microscope, 3640 IS&T/SPIE. Conference on Three Dimensional Image Capture and Applications II. 246-253. Jan. 1999.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cogswell, et al. Colour confocal reflection microscopy using red, green and blue lasers, 165 J. Microscopy 103-117 (1990).
Cogswell, et al. High-resolution, multiple optical mode confocal microscope: I. System design, image acquisition and 3D visualization, 2184 SPIE 48-54 (1994).
Constans. The Confocal Microscope, 18(22) The Scientist 32-33 (2004).
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

(56) References Cited

OTHER PUBLICATIONS

DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et a/., "Computer-Based Image Analysis of Artificial Root Surface Caries," Abstracts of Papers, J. Dent. Res., 70:528 (Apr. 17-21, 1991).
Hibbs, A.R., Confocal Microscopy for Biologists, Appx. 1, 355-443 (2004).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 p. (1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jernvall, et al. Laser confocal microscopy and geographic information systems in the study of dental morphology. Palaeontological electronica 2(1). 1999. http://www.biocenter.helsinki.fi/bi/evodevo/pdf/pe99.pdf.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Cfin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).

(56) References Cited

OTHER PUBLICATIONS

Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, Oct. 22-23, 1990.
Nishiyama et al., "A New Construction of Tooth Repositioner by LTV Vinyl Silicone Rubber," J. Nihon Univ. Sch. Dent., 19(2):93-102 (1977).
Okuda, et al., "Evaluation of in vitro secondary caries using confocal laser scanning microscope and X-ray analytical microscope" Journal of Dentistry 16(3), Summary pp. 191-196 (2003).
Paddock, Confocal Laser Scanning Microscopy, 27 Biotechniques 992-1004 (1999).
Paddock, Confocal Reflection Microscopy: The "Other" Confocal Mode, 32(2) Biotechniques 274-278 (2002).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993).
Pulli, Surface Reconstruction and Display from Range and Color Data (Dec. 2, 1997) available at UMI Microform No. 9819292 (1998).
Raintree Essix & ARS Materials, Inc., Raintree Essix, Technical Magazine Table of contents and Essix Appliances,< http:// www.essix.com/magazine/defaulthtml> Aug. 13, 1997.
Rajadhyaksha. Confocal Reflectance Microscopy: Diagnosis of Skin Cancer Without Biopsy?, Symp. Front. of Eng. (1999).
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
Tang, et al. Automatic, Accurate Surface Model Inference for Dental CAD/CAM. Proceedings of the First International Conference on Medical image Computing and Computer-Assisted Intervention, pp. 732-742 (Oct. 11-13, 1998).
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.

(56) References Cited

OTHER PUBLICATIONS

Verstreken et al., "An Image-Guided Planning System for Endosseous Oral Implants," IEEE Trans. Med. Imaging, 17(5):842-852 (Oct. 1998).
Wakabayashi, Development of the Computerized Dental Cast Form Analyzing System—Three Dimensional Diagnosis of Dental Arch Form and the Investigation of Measuring Condition, Dental Materials Journal. vol. 16(2), pp. 180-190 (1997).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Watson. Applications of confocal scanning optical microscopy to dentistry. British Dental Journal 171 (9), Summary pp. 287-291 (1991).
Watson, et al. Confocal light microscopic techniques for examining dental operative procedures and dental materials. A status report for the American Journal of Dentistry. American Journal of Dentistry 4(4), Summary pp. 193-200 (1991).
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).
Co-pending U.S. Appl. No. 16/270,419, filed Feb. 7, 2019.
Co-pending U.S. Appl. No. 16/373,482, filed Apr. 2, 2019.
Co-pending U.S. Appl. No. 16/379,657, filed Apr. 9, 2019.

Notice of Issuance of Initial Determination on Violation of Section 337 with Recommendation on Remedy and Bond, in the matter of Certain Dental and Orthodontic Scanners and Software, Inv. No. 337-TA-1144 (Apr. 30, 2020).
Jahne et al.: Handbook of Computer Vision and Applications. vol. 1: Sensors and Imaging. 1-624 (1999).
Jahne et al.: Handbook of Computer Vision and Applications. vol. 2: Signal Processing and Pattern Recognition. 1-942 (1999).
Jahne et al.: Handbook of Computer Vision and Applications. vol. 3: Systems and Applications. 1-894 (1999).
Initial Determination on Violation of Section 337 with Recommended Determination on Remedy and Bond, in the matter of Certain Dental and Orthodontic Scanners and Software, Inv. No. 337-TA-1144 (Apr. 30, 2020), dated Jun. 1, 2020.
Gove, "Image Processing Equipment," John Wiley & Sons, Inc. (Dec. 27, 1999).
Commission Opinion, in the Matter of Certain Color intraoral Scanners and Related Hardware and Software, Inv. No. 337-TA-1091 (Dec. 19, 2019).
Initial Determination on Violation of Section 337 and Recommended Determination on Remedy and Bond, in the Matter of Certain Color intraoral Scanners and Related Hardware and Software, Inv. No. 337-TA-1091 (Mar. 1, 2019).
Notice of Commission Determination Finding No Violation of Section 337; Termination of the Investigation, in the Matter of Certain Color Intraoral Scanners and Related Hardware and Software, Inv. No. 337-TA-1091 (Nov. 22, 2019).
Judgement Granting Request for Adverse Judgment After Institution of Trail, *3Shape A/S and 3Shape Inc. v. Align Tech., Inc.*, IPR2019-00157, Paper 28 (PTAB Feb. 12, 2020).
Judgement Granting Request for Adverse Judgment After Institution of Trail, *3Shape A/S and 3Shape Inc. v. Align Tech., Inc.*, IPR2019-00159, Paper 28 (PTAB Feb. 12, 2020).
Judgement Granting Request for Adverse Judgment After Institution of Trail, *3Shape A/S and 3Shape Inc. v. Align Tech., Inc.*, IPR2019-00160, Paper 31 (PTAB Feb. 19, 2020).
Judgement Granting Request for Adverse Judgment After Institution of Trail, *3Shape A/S and 3Shape Inc. v. Align Tech., Inc.*, IPR2019-00154, Paper 25 (PTAB Feb. 12, 2020).
Judgement Granting Request for Adverse Judgment After Institution of Trail, *3Shape A/S and 3Shape Inc. v. Align Tech., Inc.*, IPR2019-00155, Paper 25 (PTAB Feb. 12, 2020).
Judgement Granting Request for Adverse Judgment After Institution of Trail, *3Shape A/S and 3Shape Inc. v. Align Tech., Inc.*, IPR2019-00156, Paper 27 (PTAB Feb. 19, 2020).
Decision Denying Institution of Inter Partes Review, *3Shape A/S And 3Shape Inc. v. Align Tech., Inc.*, IPR2020-00173, Paper 14 (PTAB Jun. 12, 2020).
Decision Denying Institution of Inter Partes Review, *3Shape A/S And 3Shape Inc. v. Align Tech., Inc.*, IPR2020-00174, Paper 14 (PTAB Jun. 12, 2020).
*3Shape A/S and 3Shape Inc. v, Align Tech., Inc.*, IPR2019-00154, Paper 25 (PTAB Feb. 12, 2020).
*3Shape A/S and 3Shape Inc. v. Align Tech., Inc.*, IPR2019-00156, Paper 29 (PTAB Feb. 19, 2020).
*3Shape A/S and 3Shape Inc. v. Align Tech., Inc.*, IPR2019-00157, Paper 28 (PTAB Feb. 12, 2020).
*3Shape A/S and 3Shape Inc. v. Align Tech., Inc.*, IPR2019-00159, Paper 25 (PTAB Feb. 12, 2020).
*3Shape A/S and 3Shape Inc. v. Align Tech., Inc.*, IPR2019-00159, Paper 28 (PTAB Feb. 12, 2020).
*3Shape A/S and 3Shape Inc. v. Align Tech., Inc.*, IPR2019-00160, Paper 25 (PTAB Feb. 19, 2020).
*3Shape A/S and 3Shape Inc. v. Align Tech., Inc.*, IPR2019-00160, Paper 31 (PTAB Feb. 19, 2020).
Agathos et al., "Colour Texture Fusion of Multiple Range Images," an article published in 2003 in the IEEE Proceedings of the Fourth International Conference on 3-D Digital Imaging and Modeling.
Barequet, Gill et al., "Filling Gaps in the Boundary of a Polyhedron," Computer Aided Geometric Design, vol. 12, No. 2, pp. 207-229 (Mar. 1995).

(56) References Cited

OTHER PUBLICATIONS

Beltrame, Francesco, et al., "Three-dimensional reconstruction of paramecium primaurelia oral apparatus through confocal laser scanning optical microscopy," Proc. of SPIE 1660:728-736 (Jun. 26, 1992).
Binefa, Xavier, et al., "Three-dimensional inspection of integrated circuits: a depth from focus approach," Proc. of SPIE 1661:372-378 (Aug. 1, 1992).
Callieri et al., "Reconstructing textured meshes from multiple range+rgb maps," an article published in 2002 by the Istituto di Scienza e Tecnologie dell'Informazione.
Chen, Su-Shing, et al,, "Shape-from-focus: surface reconstruction of hybrid surfaces," Proc. of SPIE 1569:446-450 (Oct. 1, 1991).
Co-pending U.S. Appl. No. 16/791,994, submitted Feb. 14, 2020.
Co-pending U.S. Appl. No. 16/840,267, submitted Apr. 3, 2020.
Cogswell, D.K. Hamilton, and C.J.R. Sheppard, "Confocal reflection microscopy using red, green, and blue lasers," J. Microscopy 165:103-117 (Jan. 1992).
Commer, P. et al. Construction and testing of a computer-based intraoral laser scanner for determining tooth positions, Medical Engineering & Physics 22 (2000) 625-635.
Corle, Timothy R. and Gordon S. Kino, "Confocal Scanning Optical Microscopy and Related Imaging Systems," Academic Press.
Diaspro, A., "Characterizing biostructures and cellular events in 2D/3D [using wide-field and confocal optical sectioning microscopy]," IEEE Engineering in Medicine and Biology, 15(1):92-100 (Feb. 1996).
Direct Dimensions, Vivid 910 Non-Contact 3-D Digitizer. Owings Mills, MD: Direct Dimensions.
Dostalova, T., et al., "Three computer vision applications in dentistry," Proc. of SPIE 2168:416-424 (1994).
Dürrenberger, M., "Confocal laser scanning microscopy within the field of biomaterials," European Cells & Materials, vol. 1, Supp. 2, 10-11 (2001).
Eisner et al., "Confocal microscopy with a refractive microlens—pinhole array", Optics Letters/vol. 23, No. 10/May 15, 1998, Received Feb. 11, 1998.
Favaro, P. and Soatto, S., "Learning shape from defocus," Proc. European Conf. Computer Vision, 13 pages (2002).
Gmitro, "Confocal microscopy through a fiber-optic imaging bundle", Optics Letters/Apr. 15, 1993/vol. 18, No. 8, pp. 565-567.
Gühring, J., Dense 3-D Surface Acquisition by Structured Light Using Off-The-Shelf Components, 4309 Proc. SPIEE 220-231 (2000).
Guttag, K., et al., "A Single-Chip Multiprocessor for Multimedia: The MVP," IEEE Computer Graphics & Applications, pp. 53-64 (Nov. 1992).
Hajeer et al., Current Products and Practices Applications of 3D imaging in orthodontics: Part II, Journal of Orthodontics, vol. 31 (2004).
Hamilton, D.K. et al., Three-Dimensional Surface Measurement Using the confocal Scanning Microscope, University of Oxford, Department of Engineering Science, Appl. Phys. B 27, 211-213 (1982).
Herron, R.E., "The Light Beam Profiler—Past, Present, and Future," Proc. of SPIE 283:61-65 (Oct. 29, 1981).
Ishihara, Mitsuhiro, et al., "Three-dimensional surface measurement using grating projection method by detecting phase and contrast," Proc. of SPIE 3740:114-117 (May 7, 1999).
Johnson and Kang, "Registration and Integration of Textured 3-D Data," Proc. Int'l Conf. Recent Advances in 3-D Digital Imaging and Modeling, pp. 234-241, published May 1997.
Jovanovski, V. and Lynch, E., "Analysis of the morphology of oral structures from 3-D coordinate data," Monogr Oral Sci. Basel, Karger, 17:73-129 (2000).
Jovanovski, V. and Lynch, E., Analysis of the Morphology of Oral Structures from 3-D Co-Ordinate Data, 17 Assessment of Oral Health 73-129 (2000).
Koch, R. M. et al., "Simulating Facial Surgery Using Finite Element Models," SIGGRAPH '96 Proceedings of the 23rd Annual Conference on Computer Graphics and Interactive Techniques, pp. 421-428 (1996).
Konica Minolta Sensing, Inc. Minolta Non-Contact 3-D Digitizer Vivid 910/VI-910, Ramsey, NJ: Konica Minolta Sensing Advertisement (Jun. 8, 2004).
Konica Minolta Sensing, Inc. Non-Contact 3D Digitizer Vivid 910/VI-910. Ramsey, NJ: Konica Minolta Sensing Manual.
Korner, Klaus, et al., "New approaches in depth-scanning optical metrology," Proc. of SPIE 5457:320-333 (Sep. 10, 2004).
Kuhmstedt, Peter, et al., "Optical 3D sensor for large objects in industrial application," Proc. of SPIE 5856:118-127 (Jun. 13, 2005).
Kuhn, M.H. et al., "Multimodality Medical Image Analysis for Diagnosis and Treatment Planning: The COVIRA Project (Computer Vision in Radiology)," Extract from the Final Edited Report of AIM Project A2003, Commission of the European Union, DC XIII, COVIRA Status Report Jan. 1995, pp. 1-15. ("Kuhn").
Lin et al., "Vision system for fast 3-D model reconstruction," Optical Engineering, vol. 43 No. 7, published in 2004.
Lorensen, William E. et al., "Marching Cubes: A High Resolution 3D Surface Construction Algorithm," Computer Graphics, vol. 21, No. 4, pp. 163-169 (Jul. 1987).
Mac Raighne, A., et al., "Variable-focus microlenses: Issues for confocal imaging," Proc. SPIE 5827, Opto-Ireland 2005: Photonic Engineering, (Jun. 8, 2005).
Myszkowski, Karol et al., Computer modeling for the occlusal surface of teeth, The University of Aizu, pp. 965-80 Japan. IEEE. 1996.
National Semiconductor Corporation, LM9704 Real Time Digital image Processor Datasheet, Oct. 2002.
Nayar et al., "Focus range sensors," Robotics Research, pp. 378-90, published in 1995.
Nayar et al., "Shape from focus: An effective approach for rough surfaces," Proceedings., IEEE International Conference on Robotics and Automation, pp. 218-225 published in 1990.
Nayar, et al., "Real-Time Focus Range Sensor," an article published in 1996 in the IEEE Transactions on Pattern Analysis and Machine Intelligence, vol. 18, No. 12, Dec. 1996.
Nayer et al., "Shape from Focus," IEEE Transactions on Pattern analysis and machine intelligence, 16 No. 8, pp. 824-831, published in 1994.
Niederöst, M., et al., "Automatic 3D reconstruction and visualization of microscopic objects from a monoscopic multifocus image sequence," researchgate.net, 9 pages (Jan. 2002).
Nivet, Jean-Marc, et al., "Depth-scanning fringe projection technique (DSFP) with 3D calibration," Proc. of SPIE 5144:443-450 (May 30, 2003).
Noack, Joachim, et al., "Functional Topographic Imaging of the Human Retina by Confocal Scanning Laser Angiography," Proc. of SPIE 3564:132-137, Medical Applications of Lasers in Dermatology, Cardiology, Ophthalmology, and Dentistry ll, (Feb. 4, 1999).
Noguchi, M. And Nayar, S. K., "Microscopic Shape from Focus Using a Projected Illumination Pattern," Mathl. Comput. Modelling 24(5/6):31-48 (1996).
Noguchi, M. And Nayar, S. K., "Microscopic Shape from Focus Using Active Illumination," in Proceedings of 12th international Conference on Pattern Recognition, Jerusalem, Israel, 1994 pp. 147-152.
Paulus et al., "Three-dimensional computer vision for tooth restoration," Medical image analysis 3, No. 1, pp. 1-19, published in 1999.
Pulli et al., "Acquisition and Visualization of Colored 3D Objects," an article published in 1998 in the IEEE Proceedings. Fourteenth International Conference on Pattern Recognition (Cat. No. 98EX170).
Pulli et al., "Surface Reconstruction and Display from Range and Color Data,," an article published in 2000 in Graphical Models 62, 165-201.
Rivas, Jorge A, Three-dimensional digital image processing and reconstruction of granular particles, Dissertations, University of South Florida (Oct. 26, 2005).

(56) References Cited

OTHER PUBLICATIONS

Sato et al., "Object Shape and Reflectance Modeling from Observation," an article published in 2001 in Modeling from Reality, pp. 95-116.
Schick, Anton, et al., "Fast scanning confocal sensor provides high-fidelity surface profiles on a microscopic scale," Proc. of SPIE 5457:115-125 (Sep. 10, 2004).
Sheppard, C. F., "Progress in confocal microscopy and its application", Department of Physical Optics, School of Physics, University of Sydney, Australia 1994, pp. 91-94.
Subbarao, M., et al., "Accurate reconstruction of three-dimensional shape and focused image from a sequence of noisy defocused images," Proc. of SPIE 2909:178-191 (1996).
Subbarao, Murali, "Parallel Depth Recovery by Changing Camera Parameters," an article published in 1988 in the IEEE Second international Conference on Computer Vision.
Turk, Greg et al., "Zippered Polygon Meshes from Range Images," Proceedings of the 21st annual conference on Computer graphics and interactive techniques, pp. 311-318 (1994).
Tyan, Jenn-Kwei, "Analysis and application of autofocusing and three-dimensional shape recovery," Dissertation, State University of New York at Stony Brook (Dec. 1997).
Viitanen, Jouko O., et al., "Depth from focus using a compact camera arrangement," Proc. of SPIE 2904:178-182 (Oct. 29, 1996).
Watanabe et al., "Real-time computation of depth from defocus," Three-Dimensional and Unconventional Imaging for Industrial Inspection and Metrology, vol. 2599, pp. 14-25, published in 1995.
Watanabe et al., "Telocentric Optics for Focus Analysis," IEEE Transactions on Pattern Analysis and Machine Intelligence, vol. 19, No. 12, pp. 1360-1365, published Dec. 1997.
Watson et al., "In vivo confocal microscopy in clinical dental research: an initial appraisal", J. Dent. 1992; 20: 352-358.
Watson, Timothy F., "Applications of High-Speed Confocal Imaging Techniques in Operative Dentistry", Scanning vol. 16, 168-173 (1994).
Welch, William et al., "Free-Form Shape Design Using Triangulated Surfaces," Proceedings of the 21st Annual Conference on Computer Graphics and Interactive Techniques, pp. 247-256 (1994).
Willson et al., "Acitve lens control for high precision computer imaging," pp. 2063-2070, published in 1991.
Willson et. al, "Dynamic lens compensation for active color imaging and constant magnification focusing," No. CMU-RI-TR-91-26. Carnegie-Mellon Univ Pittsburgh PA Robotics Inst, published in 1991.
Xiao, G. Q., et al., "Real-time confocal scanning optical microscope," Appl. Phys. Lett. 53(8):716-18 (1988).
Yamany et al., "Free-Form Surface Registration Using Surface Signatures," The Proceedings of the Seventh IEEE international Conference on Computer Vision, Sep. 20-27, 1999; 7 pages.
Yoshizawa, Toru, et al., "Uniaxis rangefinder using contrast detection of a projected pattern," Proc. of SPIE 4190:115-122 (Feb. 12, 2001).
Inter-Parties Review Case No. IPR2019-00154, U.S. Pat. No. 8,363,228.
Inter-Parties Review Case No. IPR2019-00157, U.S. Pat. No. 8,363,228.
Inter-Parties Review Case No. IPR2019-00155, U.S. Pat. No. 8,451,456.
Inter-Parties Review Case No. IPR2019-00159, U.S. Pat. No. 8,451,456.
Inter-Parties Review Case No. IPR2019-00156, U.S. Pat. No. 8,675,207.
Inter-Parties Review Case No. IPR2019-00160, U.S. Pat. No. 8,675,207.
Inter-Parties Review Case No. IPR2019-00163, U.S. Pat. No. 9,101,433.
Inter-Parties Review Case No. IPR2020-00173, U.S. Pat. No. 8,102,538.
Inter-Parties Review Case No. IPR2020-00174, U.S. Pat. No. 8,102,538.
International Trade Commission, Color Intraoral Scanners and Related Hardware and Software.
Delaware District Court, *Align Technology, Inc.* v. *3Shape A/S et al.* Commission Opinion, In the Matter of Certain Dental and Orthodontic Scanners and Software, Inv. No. 337-TA-1144 (Dec. 3, 2020).
Notice of the Commission's Final Determination Finding No Violation of Section 337; Termination of the Investigation, In the Matter of Certain Dental and Orthodontic Scanners and Software, Inv. No. 337-TA-1144 (Nov. 17, 2020).
Watson, Timothy F., "The application of real-time confocal microscopy to the study of high-speed dental-bur-tooth-cutting interactions". Journal of Microscopy. Jan. 1, 1990 (Jan. 1, 1990). pp. 51-60. XP055538067. DOI:10.1111//.1365-2818.1990.tb02946.x Retrieved from the Internet: URL:https://onlinelibrary.wiley.com/doi/pdf/10.1111//.1365-2818.1990.tb02946.x or https://api.wiley.com/onlinelibrary/tdm/v1/articles/10.1111%2F/.1365-2818.1990.tb02946.x [retrieved on Jan. 3, 2019].
Yamany et al., "A 3-D Reconstruction System for the Human Jaw Using a Sequence of Optical Images," IEEE Transactions on Medical Imaging, May 2000, vol. 19 (5), pp. 538-547.

\* cited by examiner

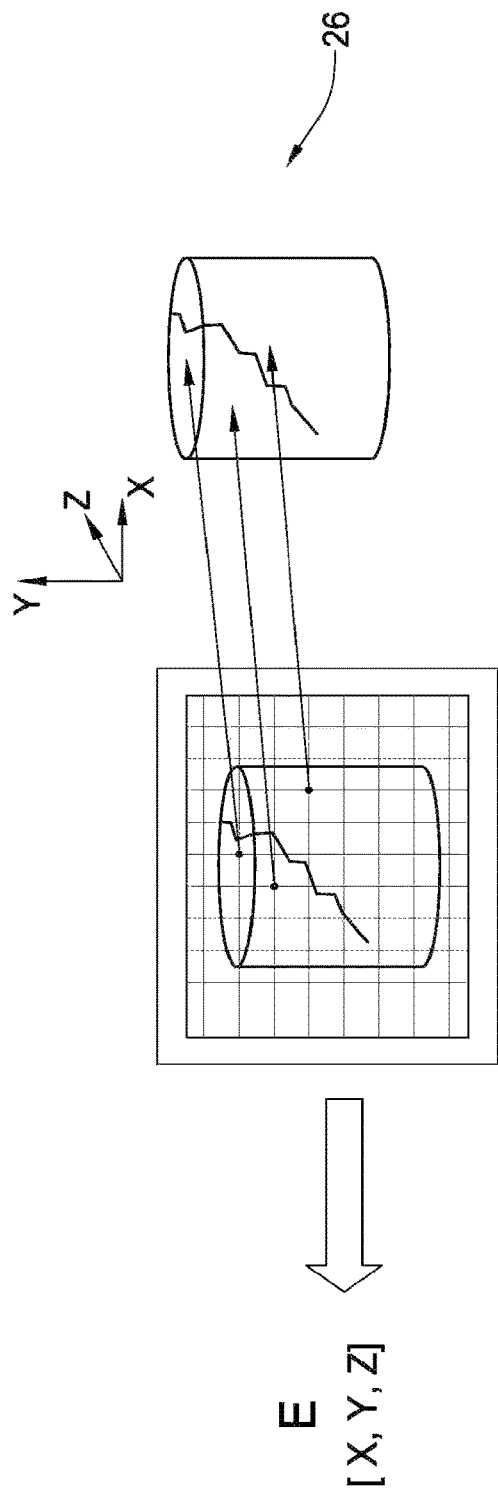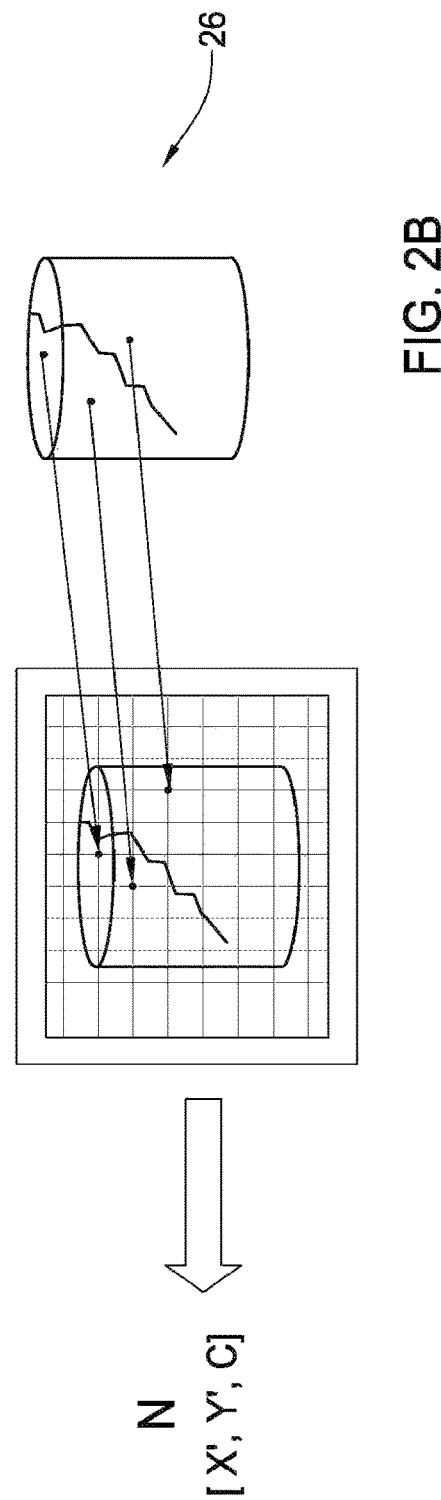

METHOD AND APPARATUS FOR COLOUR IMAGING A THREE-DIMENSIONAL STRUCTURE

CROSS-REFERENCE

This application is a continuation of U.S. patent application Ser. No. 16/270,419, filed on Feb. 7, 2019, now U.S. Pat. No. 10,812,773, issued October 20, 2020, which is a continuation of U.S. patent application Ser. No. 15/175,267, filed on Jun. 7, 2016, which is a continuation of U.S. patent application Ser. No. 14/755,171, filed on Jun. 30, 2015, now U.S. Pat. No. 9,404,740, issued Aug. 2, 2016, which is a continuation of U.S. patent application Ser. No. 14/511,091, filed on Oct. 9, 2014, now U.S. Pat. No. 9,101,433, issued Aug. 11, 2015, which is a continuation of U.S. patent application Ser. No. 14/150,505, filed on Jan. 8, 2014, now U.S. Pat. No. 8,885,175, issued Nov. 11, 2014, which is a continuation of U.S. patent application Ser. No. 13/868,926, filed on Apr. 23, 2013, now U.S. Pat. No. 8,675,207, issued Mar. 18, 2014, which is a continuation of U.S. patent application Ser. No. 13/620,159, filed on Sep. 14, 2012, now U.S. Pat. No. 8,451,456, issued May 28, 2013, which is a continuation of U.S. patent application Ser. No. 13/333,351, filed on Dec. 21, 2011, now U.S. Pat. No. 8,363,228, issued Jan. 29, 2013, which is a continuation of U.S. patent application Ser. No. 12/770,379, filed on Apr. 29, 2010, now U.S. Pat. No. 8,102,538, issued Jan. 24, 2012, which is a continuation of U.S. patent application Ser. No. 12/379,343, filed on Feb. 19, 2009, now U.S. Pat. No. 7,724,378, issued May 25, 2010, which is a continuation of U.S. patent application Ser. No. 11/889,112, filed on Aug. 9, 2007, now U.S. Pat. No. 7,511,829, issued Mar. 31, 2009, which is a continuation of U.S. patent application Ser. No. 11/154,520, filed on Jun. 17, 2005, now U.S. Pat. No. 7,319,529, issued Jan. 15, 2008, an application claiming the benefit under 35 U.S.C. § 119(e) of U.S. Provisional Application No. 60/580,109, filed on Jun. 17, 2004, and claiming the benefit under 35 U.S.C. § 119(e) of U.S. Provisional Application No. 60/580,108, filed on Jun. 17, 2004, the contents of each of which are hereby incorporated by reference in their entirety.

FIELD OF THE INVENTION

The present invention relates to optical scanners, particularly for providing a digital representation of three-dimensional objects including color. The invention finds particular application in the surveying of the intraoral cavity.

BACKGROUND OF THE INVENTION

Many methods have been developed for obtaining the three dimensional location of surface points of an object, for a host of applications including, inter alia, the intraoral cavity. Techniques for direct non-contact optical measurement, in particular for direct optical measurement of teeth and the subsequent automatic manufacture of dentures, are known. The term "direct optical measurement" signifies surveying of teeth in the oral cavity of a patient. This facilitates the obtainment of digital constructional data necessary for the computer-assisted design (CAD) or computer-assisted manufacture (CAM) of tooth replacements without having to make any cast impressions of the teeth. Such systems typically include an optical probe coupled to an optical pick-up or receiver such as charge coupled device (CCD) and a processor implementing a suitable image processing technique to design and fabricate virtually the desired product. Such methods include, for example, confocal imaging techniques as described in WO 00/08415 assigned to the present assignee. These methods provide a digital three-dimensional surface model that is inherently monochromatic, i.e., no color information is obtained in the imaging process.

Associating color information with three-dimensional objects is not straightforward, particularly when the position information is obtained by using a three dimensional scanning method, while the color information is obtained by using a two dimensional scanning method. The problem of conformally mapping the two dimensional color information onto the three dimensional surface model is difficult and it is common for mismatching of the color with three-dimensional points to occur. Essentially, where two-dimensional color detectors are used for obtaining the color information, it is difficult to accurately associate color information from the detectors with the correct points on the three dimensional surface model, particularly where relative movement between the object and the device occurs between the acquisition of the three-dimensional topological data and acquisition of the two-dimensional image data.

EP 837 659 describes a process and device for obtaining a three dimensional image of teeth. Three-dimensional surface data is obtained by first covering the surface with an opaque, diffusely reflecting material, and the object is illuminated with monochromatic light. The image of the object under the layer is obtained by the process described in U.S. Pat. No. 4,575,805 using intensity pattern techniques. In order to obtain a two-dimensional color image of the object, the reflecting layer has to be removed. The method thus requires the camera to be manually re-aligned so that the two-dimensional color image should more or less correspond to the same part of the object as the three dimensional image. Then, the three dimensional image may be viewed on a screen as a two-dimensional image, and it is possible to superimpose on this two-dimensional image the two-dimensional color image of the teeth taken by the camera.

U.S. Pat. No. 6,594,539 provides an intraoral imaging system that produces images of a dental surface, including three dimensional surface images and also two dimensional color images, with the same camera.

In U.S. Pat. No. 5,440,393, the shape and dimensions of a dental patients mouth cavity including upper and lower tooth areas and the jaw structure, are measured by an optical scanner using an external radiation source, whose reflected signals are received externally and converted into electronic signals for analysis by a computer. Both surface radiation and reflection from translucent internal surfaces are scanned, and processing of reflections may involve a triangulation system or holograms.

In U.S. Pat. No. 5,864,640, a scanner is described having a multiple view detector responsive to a broad spectrum of visible light. The detector is operative to develop several images of a three dimensional object to be scanned. The images are taken from several relative angles with respect to the object. The images depict several surface portions of the object to be scanned. A digital processor, coupled to the detector, is responsive to the images and is operative to develop with a computational unit 3-D coordinate positions and related image information of the surface portions of the object, and provides 3-D surface information that is linked to color information without need to conformally map 2-D color data onto 3-D surface.

Of general background interest, U.S. Pat. Nos. 4,836,674, 5,690,486, 6,525,819, EP 0367647 and U.S. Pat. No. 5,766,006 describe devices for measuring the color of teeth.

SUMMARY OF THE INVENTION

In accordance with the present invention, a device and method for determining the surface topology and color of at least a portion of a three dimensional structure is provided. Preferred non-limiting embodiments of the invention are concerned with the imaging of a three-dimensional topology of a teeth segment, optionally including such where one or more teeth are missing. This may allow the generation of data for subsequent use in design and manufacture of, for example, prosthesis of one or more teeth for incorporation into said teeth segment. Particular examples are the manufacture of crowns, bridges dental restorations or dental filings. The color and surface data is provided in a form that is highly manipulable and useful in many applications including prosthesis color matching and orthodontics, among others.

The determination of the 3D surface topology of a portion of a three-dimensional structure is preferably carried out using a confocal focusing method, comprising:

(a) providing an array of incident light beams propagating in an optical path leading through a focusing optics and a probing face; the focusing optics defining one or more focal planes forward said probing face in a position changeable by said optics, each light beam having its focus on one of said one or more focal plane; the beams generating a plurality of illuminated spots on the structure;

(b) detecting intensity of returned light beams propagating from each of these spots along an optical path opposite to that of the incident light;

(c) repeating steps (a) and (b) a plurality of times, each time changing position of the focal plane relative to the structure; and (d) for each of the illuminated spots, determining a spot-specific position, being the position of the respective focal plane, yielding a maximum measured intensity of a respective returned light beam; and based on the determined spot-specific positions, generating data representative of the topology of said portion.

The determination of the spot-specific positions in fact amounts to determination of the in-focus distance. The determination of the spot-specific position may be by measuring the intensity per se, or typically is performed by measuring the displacement (S) derivative of the intensity (I) curve (dI/dS) and determining the relative position in which this derivative function indicates a maximum intensity. The term "spot-specific position (SSP)" will be used to denote the relative in-focus position regardless of the manner in which it is determined. It should be understood that the SSP is always a relative position as the absolute position depends on the position of the sensing face. However the generation of the surface topology does not require knowledge of the absolute position, as all dimensions in the cubic field of view are absolute.

The SSP for each illuminated spot will be different for different spots. The position of each spot in an X-Y frame of reference is known and by knowing the relative positions of the focal plane needed in order to obtain maximum intensity (namely by determining the SSP), the Z or depth coordinate can be associated with each spot and thus by knowing the X-Y-Z coordinates of each spot the surface topology can be generated.

In order to determine the Z coordinate (namely the SSP) of each illuminated spot the position of the focal plane may be scanned over the entire range of depth or Z component possible for the measured surface portion. Alternatively the beams may have components, each of which has a different focal plane. Thus, by independent determination of SSP for the different light components, e.g. 2 or 3 with respective corresponding 2 or 3 focal planes, the position of the focal planes may be changed by the focusing optics to scan only part of the possible depth range, with all focal planes together covering the expected depth range. Alternatively, the determination of the SSP may involve a focal plane scan of only part of the potential depth range and for illuminated spots where a maximum illuminated intensity was not reached, the SSP is determined by extrapolation from the measured values or other mathematical signal processing methods. Thus, in each case, a Z-value is obtained for each point along an X-Y grid representing a plurality of light beams. In this manner, a three-dimensional (3D) numerical entity E may be crated, comprising a plurality of coordinates (X, Y, Z) representative of the surface topology of the object being scanned.

Alternatively, any other suitable method may be employed to obtain the 3D entity E.

According to the present invention, a two dimensional (2D) color image of the 3D structure that is being scanned is also obtained, but typically within a short time interval with respect to the 3D scan. Further, the 2D color image is taken at substantially the same angle and orientation with respect to the structure as was the case when the 3D scan was taken. Accordingly, there is very little or no substantial distortion between the X-Y plane of 3D scan, and the plane of the image, i.e., both planes are substantially parallel, and moreover substantially the same portion of the structure should be comprised in both the 3D scan and the 2D image. This means that each X-Y point on the 2D image substantially corresponds to a similar point on the 3D scan having the same relative X-Y values. Accordingly, the same point of the structure being scanned has substantially the same X-Y coordinates in both the 2D image and the 3D scan, and thus the color value at each X, Y coordinate of the 2D color scan may be mapped directly to the spatial coordinates in the 3D scan having the same X, Y coordinates, wherein to create a numerical entity I representing the color and surface topology of the structure being scanned.

Where the X, Y coordinates of the color image do not precisely correspond to those of the 3D scan, for example as may arise where one CCD is for the 3D scanning, while another CCD is used for the 2D color image, suitable interpolation methods may be employed to map the color data to the 3D spartial data.

To provide a more accurate mapping, it is possible to construct a 2D image along the X-Y plane of the 3D model, and using procedures such as optical recognition, manipulate the color 2D image to best fit over this 3D image. This procedure may be used to correct for any slight misalignment between the 2D color scan and the 3D scan. Once the color 2D image has been suitably manipulated, the color values of the color 2D image are mapped onto the adjusted X-Y coordinates of the 3D scan.

Thus the present invention provides a relatively simple and effective way for mapping 2D color information onto a 3D surface model.

The present invention thus provides a device and method for obtaining a numerical entity that represents the color and surface topology of an object. When applied particularly to the intraoral cavity, the device of the invention provides advantages over monochrome 3D scaners, including such scanners that are based on confocal focusing techniques. For example, the 2D color image capability on its own enables the dental practitioner to identify the area of interest within the oral cavity with a great degree of confidence in order to better aim the device for the 3D scanning. In other words, an improved viewfinder is automatically provided. Further, rendition of a full color 3D image of the target area can help the practitioner to decide on the spot whether the scan is sufficiently good, or whether there are still parts of the teeth or soft tissues that should have been included, and thus help the practitioner to deciode whether or not to acquire another 3D color entity.

Creation of a color 3D entity that is manipulable by a computer is extremely useful in enabling the practitioner to obtain data from such an entity that is useful for procedures carried out in the dental cavity.

Thus, according to the present invention, a device is provided for determining the surface topology and associated color of at least a portion of a three dimensional structure, comprising:

scanning means adapted for providing depth data of said portion corresponding to a two-dimensional reference array substantially orthogonal to a depth direction;

imaging means adapted for providing two-dimensional color image data of said portion associated with said reference array;

wherein the device is adapted for maintaining a spatial disposition with respect to said portion that is substantially fixed during operation of said scanning means and said imaging means. In other words, operation of the scanning means and the imaging means is substantially or effectively simultaneous in practical terms, and thus the actual time interval that may exist between operation of the two means is so short that the amplitude of any mechanical vibration of the device or movement of the oral cavity will be so small as can be ignored.

The device is adapted for providing a time interval between acquisition of said depth data and acquisition of said color image data such that substantially no significant relative movement between said device and said portion occurs. The time interval may be between about 0 seconds to about 100 milliseconds, for example 5, 10, 20, 30, 40, 50, 60, 70, 80, 90 or 100 milliseconds, and preferably between about 0 to about 50 milliseconds, and more preferably between about 0 and 20 milliseconds.

The device further comprise processing means for associating said color data with said depth data for corresponding data points of said reference array. In described embodiments, the operation of said scanning means is based on confocal imaging techniques. Such scanning means may comprise:

a probing member with a sensing face;

first illumination means for providing a first array of incident light beams transmitted towards the structure along an optical path through said probing unit to generate illuminated spots on said portion along said depth direction, wherein said first array is defined within said reference array;

a light focusing optics defining one or more focal planes forward said probing face at a position changeable by said optics, each light beam having its focus on one of said one or more focal plane;

a translation mechanism for displacing said focal plane relative to the structure along an axis defined by the propagation of the incident light beams;

a first detector having an array of sensing elements for measuring intensity of each of a plurality of light beams returning from said spots propagating through an optical path opposite to that of the incident light beams;

a processor coupled to said detector for determining for each light beam a spot-specific position, being the position of the respective focal plane of said one or more focal planes yielding maximum measured intensity of the returned light beam, and based on the determined spot-specific positions, generating data representative of the topology of said portion.

The first array is arranged to provide depth data at a plurality of predetermined spatial coordinates substantially corresponding to the spatial disposition of said incident light beams.

The first illumination means comprises a source emitting a parent light beam and a beam splitter for splitting the parent beam into said array of incident light beams. The first illumination means may comprise a grating or microlens array.

The device may comprise a polarizer for polarizing said incident light beams are polarized. Further, the device may comprise a polarization filter for filtering out from the returned light beams light components having the polarization of the incident light beams.

The illumination unit may comprise at least two light sources and each of said incident beams is composed of light components from the at least two light sources. The at least two light sources emit each a light component of different wavelength. The light directing optics defines a different focal plane for each light component and the detector independently detects intensity of each light components.

The at least two light sources may be located so as to define optical paths of different lengths for the incident light beams emitted by each of the at least two light sources.

Typically, the focusing optics operates in a telecentric confocal mode. Optionally, the light directing optics comprises optical fibers.

Typically, the sensing elements are an array of charge coupled devices (CCD). The detector unit may comprise a pinhole array, each pinhole corresponding to one of the CCDs in the CCD array.

The operation of said imaging means may be based on:

illuminating said portion with three differently-colored illumination radiations, the said illuminations being combinable to provide white light, capturing a monochromatic image of said portion corresponding to each said illuminating radiation, and combining the monochromatic images to create a full color image, wherein each said illuminating radiation is provided in the form of a second array of incident light beams transmitted towards the portion along an optical path through said probing unit to generate illuminated spots on said portion along said depth direction, wherein said second array is defined within said reference frame.

The second array is arranged to provide color data at a plurality of spatial coordinates substantially corresponding to the spatial coordinates of said first array. The device may comprise color illumination means adapted for providing three second illuminating radiations, each of a different color. The color illumination means comprises second illumination means for providing said three second illuminating radiations, each of a different color. Alternatively, the color illumination means comprises second illumination means for providing two said second illuminating radiations, and wherein said first illumination means provides another said second illuminating radiation each said second illuminating radiation being of a different color. Optionally, each one of said second illumination radiations is a different one of red, green or blue light. The second illumination means may comprise radiation transmission elements that are configured to be located out of the path of said light beams or said returned light beam at least within said light focusing optics. The probing member may be made from a light transmissive material having an upstream optical interface with said light focusing optics and a reflective face for reflecting light between said optical interface and said sensing face. The second illumination means may be optically coupled to said optical interface for selectively transmitting illuminating radiations in at least two colors to said portion via said sensing face. The color illumination means may comprise second illumination means for providing two said second illuminating radiations, and wherein said first illumination means provides another said second illuminating radiation each said second illuminating radiation being of a different color. The probing member may comprise a removable sheath having an inner surface substantially complementary to an outer surface of said probing member, and having a window in registry with said sensing face, wherein said sheath is made from a waveguiding material and is adapted to transmit said light from said second illuminating means from an upstream face thereof to a downstream face associated with said window. The second illumination means may be optically coupled to said upstream face for selectively transmitting said second illuminating radiations in at least two colors to said portion via said downstream face. Preferably, the sheath is disposable after use with a patient.

In another embodiment, the reflective face comprises a dichroic coating, having relatively high reflectivity and low optical transmission properties for a said second illuminating radiation provided by said first illumination means, and relatively low reflectivity and high optical transmission properties for the two said second illuminating radiations provided by said second illumination means.

The second illumination means may be adapted for providing second illuminating radiations within said light focusing optics. In particular, the second illumination means may be adapted for providing second illuminating radiations at an aperture stop plane of said light focusing optics. The second illumination means may be provided on a bracket having an aperture configured to allow said light beams and said returning light beams to pass therethrough without being optically affected by said bracket.

Optionally, the device further comprises:
 a first polarizing element located just downstream of said illumination means so as to polarize the light emitted therefrom;
 a second polarizing element located just upstream of said first detector, wherein said second polarizing element is crossed with respect to the first polarizing element; and
 a quarter waveplate at the downstream end of said device.

Further optionally the second illumination means are adapted for selective movement in the depth direction.

The device may comprise a mirror inclined to the optical axis of said light focusing optics and having, an aperture configured to allow said light beams and said returning light beams to pass therethrough without being optically affected by said mirror, and wherein said second illumination means comprises at least one white illumination source optically coupled with suitable color filters, said filters selectively providing illumination radiation in each color in cooperation with said white illumination source, wherein said mirror is coupled to said white illumination source to direct radiation therefrom along said optical axis. The white illumination source may comprise a phosphorus InGaN LED. The filters may be arranged on sectors of a rotatable disc coupled to a motor, predetermined selective angular motion of said disc selectively couples said white illumination source to each said filter in turn.

Optionally, the second illumination means are in the form of suitable LED's, comprising at least one LED for providing illumination radiation in each color. Optionally, the second illumination means are in the form of suitable LED's, comprising at least one white illumination source optically coupled with suitable color filters, said filters selectively providing illumination radiation in each color in cooperation with said white illumination source. The white illumination source may comprise a phosphorus InGaN LED. The filters may be arranged on sectors of a rotatable disc coupled to a motor, predetermined selective angular motion of said disc selectively couples said white illumination source to each said filter in turn. The device may further comprise a plurality of optical fibers in optical communication with said filters and with radiation transmission elements comprised in said second illumination means.

The first detector is adapted for selectively measuring intensity of each said second illuminating radiation after reflection from said portion.

Alternatively, the operation of said imaging means is based on illuminating said portion with substantially white illumination radiation, and capturing a color image of said portion, wherein said white illuminating radiation is provided in the form of a second array of incident light beams transmitted towards the portion along an optical path through said probing unit to generate illuminated spots on said portion along said depth direction, wherein said second array is defined within said reference frame. The second array is arranged to provide color data at a plurality of spatial coordinates substantially corresponding to the spatial coordinates of said first array. The imaging means comprises:—
 white illumination radiation means;
 second detector having an array of sensing elements for measuring intensity of said white illuminating radiation after reflection from said portion.

Alternatively, the operation of said imaging means is based on illuminating said portion with substantially white illumination radiation, selectively passing radiation reflected from said portion through a number of color filters, capturing a monochromatic image of said portion corresponding to each said filter, and combining the monochromatic images to create a full color image, wherein said illuminating radiation is provided in the form of a second array of incident light beams transmitted towards the portion along an optical path through said probing unit to generate illuminated spots on said portion along said depth direction, wherein said second array is defined within said reference frame. The second array is arranged to provide color data at a plurality of spatial coordinates substantially corresponding to the spatial coordinates of said first array.

Alternatively, the operation of said imaging means is based on illuminating said portion with three differently-colored illumination radiations, capturing a monochromatic image of said portion corresponding to each said illuminating radiation, and combining the monochromatic images to create a full color image, wherein each said illuminating radiation is provided in the form of a second array of incident light beams transmitted towards the portion along an optical path through said probing unit to generate illuminated spots on said portion along said depth direction, wherein said second array is defined within said reference frame, and wherein said illuminating radiations are provided by said first illumination source. The second array is arranged to provide color data at a plurality of spatial coordinates substantially corresponding to the spatial coordinates of said first array.

The device may further comprise a tri-color sequence generator for controlling the illumination of said portion with said second illuminating radiations.

The device further comprises a processor coupled to said detector for conformally mapping color data provided by said imaging means to said depth data provided by said scanning means for each said spatial coordinates of said first array to provide a color three-dimensional numerical entity comprising a plurality of data points, each data point comprising three-dimensional surface coordinate data and color data associated therewith. The device may also optionally comprise a unit for generating manufacturing data for transmission to CAD/CAM device based on said entity, and a communication port of a communication medium.

The device is adapted for determining color and surface topology of a teeth portion, but may be used for determining color and surface topology of any suitable surface.

The present invention is also directed to a method for determining the surface topology and associated color of at least a portion of a three dimensional structure, comprising:

(a) providing depth data of said portion corresponding to a two-dimensional reference array substantially orthogonal to a depth direction;

(b) providing two-dimensional image data of said portion associated with said reference array;

(c) ensuring that a spatial disposition with respect to said portion during steps (a) and (b) is substantially fixed;

(d) conformally mapping said color data to said depth data for said reference array.

Preferably, in step (c), a minimum time interval is allowed between acquisition of said depth data and acquisition of said image data. The time interval may be between about 0 seconds to about 100 milliseconds, preferably between 0 and 50 milliseconds, and more preferably between 0 and 20 milliseconds.

In described embodiments, the depth data is provided using confocal imaging techniques. The method can then comprise:

(i) providing a first array of incident light beams defined within said reference array propagating in an optical path leading through a focusing optics and through a probing face; the focusing optics defining one or more focal planes forward said probing face in a position changeable by said optics, each light beam having its focus on one of said one or more focal plane; the beams generating a plurality of illuminated spots on the structure;

(ii) detecting intensity of returned light beams propagating from each of these spots along an optical path opposite to that of the incident light;

(iii) repeating steps (i) and (ii) a plurality of times, each time changing position of the focal plane relative to the structure;

(iv) for each of the illuminated spots, determining a spot-specific position, being the position of the respective focal plane yielding a maximum measured intensity of a respective returned light beam; and (v) generating data representative of the topology of said portion.

Step (ii) may be based on illuminating said portion with at least three differently-colored illumination radiations, said illumination radiations being combinable to produce white radiation, capturing a monochromatic image of said portion corresponding to each said illuminating radiation, and combining the monochromatic images to create a full color image, wherein each said illuminating radiation is provided in the form of a second array of incident light beams transmitted towards the portion along an optical path through said probing unit to generate illuminated spots on said portion along said depth direction, wherein said second array is defined within said reference frame. The second array is arranged to provide color data at a plurality of spatial coordinates substantially corresponding to the spatial coordinates of said first array.

Optionally, the sources for the at least three colored illuminations may be located at the confocal system aperture stop, and facing the objective lens of the system. Preferably, the illumination sources are configured to have a relatively low numerical aperture compared with that of the first array of light beams. Further preferably, the confocal system is configured for chromatically dispersing said colored illuminations therethrough.

Preferably, the method further comprises providing an improved focus 2D color image of said structure, comprising:—

(I) sequentially illuminating the structure with each one of a plurality of illuminations, each said illumination having a different wavelength in the visible spectrum;

(II) providing a monochrome image of the structure when illuminated with each illumination in (I);

(III) manipulating image data obtained in (II) to provide a best focus composite image;

(IV) manipulating image data in (II) and (III) to provide a composite focused color image of the structure.

Further preferably, the said sources for the colored illuminations are moveable in the depth direction.

Optionally, the method of the invention further comprises the steps of:

polarizing the emitted colored illuminations by means of a first polarizing element;

modifying the said polarized color illuminations on the way to the structure and on their return therefrom by means of a quarter waveplate;

causing the returning color illuminations to pass through a second polarizing element located just upstream of said first detector, wherein said second polarizing element is crossed with respect to the first polarizing element.

Step (ii) may be based on illuminating said portion with substantially white illumination radiation, selectively passing radiation reflected from said portion through a number of color filters, capturing a monochromatic image of said portion corresponding to each said filter, and combining the monochromatic images to create a full color image, wherein said illuminating radiation is provided in the form of a second array of incident light beams transmitted towards the portion along an optical path through said probing unit to generate illuminated spots on said portion along said depth direction, wherein said second array is defined within said reference frame. The second array is arranged to provide color data at a plurality of spatial coordinates substantially corresponding to the spatial coordinates of said first array.

Step (ii) may be based on illuminating said portion with three differently-colored illumination radiations, capturing a monochromatic image of said portion corresponding to each said illuminating radiation, and combining the monochromatic images to create a full color image, wherein each said illuminating radiation is provided in the form of a second array of incident light beams transmitted towards the portion along an optical path through said probing unit to generate illuminated spots on said portion along said depth direction, wherein said second array is defined within said reference frame, and wherein said illuminating radiations are provided by said first illumination source. The second array is arranged to provide color data at a plurality of spatial coordinates substantially corresponding to the spatial coordinates of said first array.

The data representative of said topology may be used for constructing an object to be fitted within said structure, or may be converted into a form transmissible through a communication medium to recipient. Typically, the structure is a teeth segment. The structure may be a teeth segment with at least one missing tooth or a portion of a tooth and said object is said at least one missing tooth or the portion of the tooth. Thus, for example, steps (i) to (v) may be repeated for two different surfaces of said structure to provide surface topologies thereof, and the surface topologies may then be combined to obtain color and topological data representative of said structure.

The method of the invention, and also the operation of the device of the present invention, may be modified to take account of any possible relative movement between the device and the intra oral cavity, for example as follows:—

(a) providing depth data of said portion corresponding to a two-dimensional reference array substantially orthogonal to a depth direction;

(b) providing two-dimensional image data of said portion associated with said reference array;

(c) repeating step (a);

(d) for each image color data point obtained in step (b), i.e., for each particular (x, y) point on the array for which a color value was obtained in step (b), providing an estimated value for depth, based on the depth values obtained in steps (a) and (c) for the same part of the array, i.e. based on the Z-values obtained for the same (x, y) point in steps (a) and (c). The estimated value may be based on a simple arithmetic mean, on a weighted mean, or on any suitable empirical or theoretical formula, algorithm and so on.

Of course, step (a) may be repeated a number of times consecutively before step (b), and optionally also after step (b), the time intervals between each step being taken. In any case, for each point on the array (x, y), the values of depth Z may be plotted against elapsed time, for steps (a) (single or repeated), through step (b) and steps (c) (single or repeated), and the best estimate of the value of Z corresponding to the time interval when step (b) was carried out can be calculated, using, for example, any suitable interpolation or curve-fitting method.

Alternatively, the method of the invention, and thus the operation of the device of the present invention, may be modified to take account of any possible relative movement between the device and the intra oral cavity, for example as follows:

(a) providing two-dimensional image data of said portion associated with said reference array;

(b) providing depth data of said portion corresponding to a two-dimensional reference array substantially orthogonal to a depth direction;

(c) repeating step (a);

(d) for each depth data point obtained in step (b), i.e., for each particular (x, y) point on the array for which a depth value was obtained in step (b), providing an estimated value for color, based on the color values obtained in steps (a) and (c) for the same part of the array, i.e. based on the C-values obtained for the same (x, y) point in steps (a) and (c). The estimated value may be based on a simple arithmetic mean, on a weighted mean, or on any suitable empirical or theoretical formula, algorithm and so on.

Of course, step (a) may optionally be repeated a number of times consecutively before step (b), and optionally also after step (b), the time intervals between each step being taken. In any case, for each point on the array (x, y), the values of color C may be plotted against elapsed time, for steps (a) (single or repeated), through step (b) and steps (c) (single or repeated), and the best estimate of the value of C corresponding to the time interval when step (b) was carried out can be calculated, using, for example, any suitable interpolation or curve-fitting method.

Optionally, the steps of providing color values and depth values may be repeated in any sequence, for example in alternate sequence, and a suitable color value may be associated with a corresponding depth value, similarly to the manner described above, mutatis mutandis.

The invention also relates to a method for reconstruction of color and topology of a three-dimensional structure comprising:

determining surface topologies from at least two different positions or angular locations relative to the structure, by the method of the invention described above;

combining the surface topologies to obtain color and topological data representative of said structure.

The method may be applied to the reconstruction of topology of a teeth portion, and comprise the steps:

determining surface topologies of at least a buccal surface and a lingual surface of the teeth portion;

combining the surface topologies to obtain data representative of a three-dimensional structure of said teeth portion.

The method may be applied to obtaining data representative of a three-dimensional structure of a teeth portion with at least one missing tooth or a portion of a tooth.

The data may be used in a process of designing or manufacturing of a prostheses of said at least one missing tooth or a portion of a tooth. Such a prosthesis may be, for example, a crown, a bridge, a dental restoration or a dental filing.

The present invention is directed to a method of providing data useful in procedures associated with the oral cavity comprising:

providing at least one numerical entity representative of the three-dimensional surface geometry and colour of at least part of the intra-oral cavity; and manipulating said entity to provide desired data therefrom.

Typically, the numerical entity comprises surface geometry and colour data associated with said part of the intra-oral cavity, and the colour data includes actual or perceived visual characteristics including hue, chroma, value, translucency, reflectance.

In an first embodiment, particularly useful for differentiating a first tissue from a second tissue, wherein said first tissue comprises substantially different colour characteristics from those of said second tissue, comprises separating said surface geometry and colour data into at least two tissue data sets, wherein a first said tissue data set comprises surface geometry and colour data, wherein said colour data thereof is correlated with a colour representative of said first tissue; and a second said tissue data set comprises surface geometry and colour data, wherein said colour data thereof is correlated with a colour representative of said second tissue.

The first tissue comprises hard tissues such as teeth, and the soft tissue comprises at least one of gums, tongue, cheeks and lips.

The first tissue data set may correspond to a plurality of teeth of said intraoral cavity, and in the next step the first tissue data set is divided into a plurality of sub data sets, wherein each said sub data set correspond to a different said tooth.

In the next step, the sub data sets may be manipulated in a manner simulating an orthodontic treatment on said teeth.

Optionally, the sub data sets may be displayed as images corresponding to individual teeth.

The first embodiment may also be used for determining the finish line for a dental preparation.

The second embodiment is particularly useful for stitching at least two said entities, wherein at least a portion of said entities comprise overlapping spatial data, comprising:— for each entity providing at least one sub entity comprising a first tissue data set comprising surface geometry and colour data, wherein said colour data thereof is correlated with a colour representative of a first tissue; and stitching said first tissue data sets together based on registering portions of said data set comprising said overlapping spatial data.

The first tissue may comprise hard tissues of the intraoral cavity, such as for example teeth.

Optionally, the method may further comprise the step of:

for each entity separating said surface geometry and colour data into a second tissue data set, comprising surface geometry and colour data, wherein said colour data thereof is correlated with a colour representative of a second tissue.

The second tissue typically comprises the soft tissues of the intraoral cavity, including at least one of gums, tongue, cheeks and lips.

In one variation of the method, step (b) comprises:

providing coarse stitching of the original entities of step (a) by registering overlapping spatial data thereof to determine coarse spatial relationships between said entities;

applying said coarse spatial relationships to said first tissue data sets to facilitate registration of overlapping portions; and stitching said first tissue data sets together based on registering said overlapping portions.

By eliminating the data associated with the soft tissues, and proceeding with stitching only the hard tissues using the colour data, the quality of the stitching procedure is significantly better than when using the full infra-oral data for the stitching procedure.

A third embodiment is particularly useful for providing a finish line for a preparation area in said intraoral cavity, though it may also be used for virtually separating the teeth from the gums. The method comprises:— comparing the colour data for each pair of spatially adjacent data points in said numerical entity;

if the colour data for said pair of data points are substantially different one from the other, providing one said data point of said pair of data points; and (c) applying a search algorithm for identifying said finish line in said numerical entity, wherein said application of said algorithm is initially applied to a part of said entity corresponding to the said provided data points of step (b).

Optionally, in step (b) the data point of said pair of data points having colour data associated with a hard tissue is provided for step (c).

In a fourth embodiment of the invention, the colour data associated with at least one tooth of said intraoral cavity is used for providing shading data for a prosthesis for use in said intraoral cavity.

The method typically includes the steps:

providing separate numerical sub-entities each associated with a different one of at least one tooth within said infra-oral cavity;

providing a prosthesis entity comprising surface geometrical data, said prosthesis entity being associated with a desired prosthesis;

mapping colour data from at least one sub entity in step (a) to said prosthesis entity according to predetermined criteria.

Optionally, step (c) comprises transforming the geometrical data of each said separate numerical sub-entities to correspond to a predetermined geometrical form, and mapping said colour data to said geometrical form to provide for each said separate numerical sub-entity a transformed sub-entity;

transforming the geometrical data in (b) to correspond to said prosthesis entity and mapping colour data associated with the transformed sub-entity to said prosthesis entity.

Optionally, in step (a) a single numerical sub-entity associated with one tooth within said infra-oral cavity is provided.

Alternatively, in step (a) a plurality of separate numerical sub-entities associated with a corresponding plurality of teeth within said infra-oral cavity are provided; and wherein in step (c) the said transformed sub-entities are combined to a single transformed sub-entity, wherein colour data corresponding to said plurality of numerical sub-entities in (a) are combined in a predetermined manner. Such a predetermined manner comprises averaging the colour value at each corresponding data point of said plurality of numerical sub-entities in (a). Optionally, the predetermined manner comprises weight averaging the colour value at each corresponding data point of said plurality of numerical sub-entities in (a).

Typically, step (a) comprises:— separating said surface geometry and colour data into at least two tissue data sets, wherein a first said tissue data set comprises surface geometry and colour data, wherein said colour data thereof is correlated with a colour representative of said first tissue; and a second said tissue data set comprises surface geometry and colour data wherein said colour data thereof is correlated with a colour representative of said second tissue.

The first tissue comprises hard tissues such as teeth, and the soft tissue comprises at least one of gums, tongue, cheeks and lips.

The first tissue data set may correspond to a plurality of teeth of said intraoral cavity, and in the next step the first tissue data set is divided into a plurality of sub data sets, wherein each said sub data set correspond to a different said tooth.

In another aspect of the present invention, a computer readable medium is provided that embodies in a tangible manner a program executable for providing data useful in procedures associated with the oral cavity. The computer readable medium comprises:

a first set of data representative of the three dimensional surface geometry and colour of at least part of the intra oral cavity;

means for manipulating said first data set to provide desired data therefrom.

The medium may comprise, for example, optical discs, magnetic discs, magnetic tapes, and so on.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In order to understand the invention and to see how it may be carried out in practice, a number of embodiments will now be described, by way of non-limiting example only, with reference to the accompanying drawings, in which:

FIGS. 2A, 2B, 2C graphically illustrates the creation of a three dimensional color entity from a three dimensional monochrome entity and a two dimensional color entity.

DETAILED DESCRIPTION OF THE INVENTION

The first step of the method according to the present invention relates to providing at least one numerical entity that is representative of the three-dimensional surface geometry and colour of at least part of the intra-oral cavity.

The said numerical entity is typically at least "four-dimensional", that is, each data point of the data set comprises at least four prime independent variables. In the preferred embodiments of the invention, three of the prime independent variables relate to spatial coordinates of a surface, typically defined along orthogonal Cartesian axes, x, y, z. Alternatively, these variables may be defined along polar axes or any other geometric system in which a surface may be described. The fourth prime independent variable refers to a colour parameter that is expressed numerically and associated with the spatial coordinates. The colour parameter may itself be comprised of independent prime colour variables—for example relating to the red, blue and green (RGB) components associated with the colour parameter. Alternatively, the colour parameter may be expressed in terms of the Hue, Saturation and Intensity (HIS). Alternatively, any other colour parameter may be used, including parameters that provide a measure of internal reflectance and translucency, or any other optical property of teeth.

Thus, the numerical entity may comprise a data set of a plurality of 4-dimensional arrays (x, y, z, c), wherein each array represents the x, y, z, geometrical coordinates and the colour c of a point on a surface within the intra-oral cavity.

Any suitable means may be used to provide the numerical entity. For example, a three-dimensional surface scanner with colour capabilities may be used. Advantageously, such a scanner makes use of confocal imaging for providing an accurate three-dimensional representation of the target surface within the intra-oral cavity. Colour values are then added to each data point of this data set by obtaining a two-dimensional colour image of the target surface, and then mapping the colour values of the two-dimensional image onto the three-dimensional "image".

The following are examples on how to obtain the 3d colour numerical entity.

Figure 1:
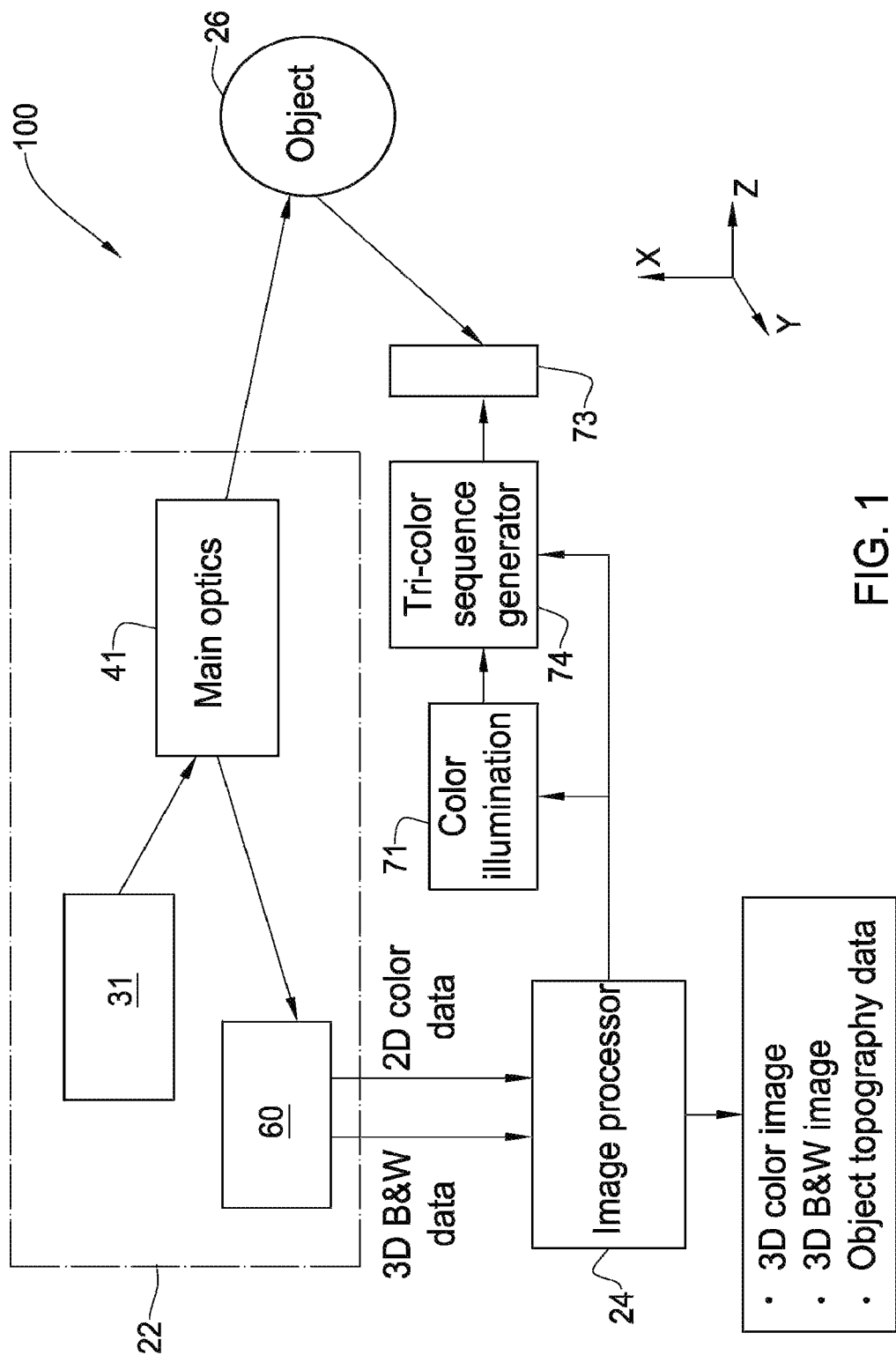
FIG. 1 illustrates the main elements of embodiments of the devices for creating a three-dimensional color numerical entity that is manipulated according to the present invention.

Reference is first being made to FIG. 1 which illustrates the general relationship between the various elements of a device for providing a 3D numerical entity, generally designated with the numeral 100, according to the embodiments described herein.

The device 100 comprises a main illumination source 31 for illuminating the object of interest 26, typically a part of the intraoral cavity, and is optically coupled to main optics 41 to provide depth Z values for an array range of X-Y points (according to a known frame of reference) along the surface of the object 26. Detection optics 60 comprises an image sensor, typically a CCD, that is preferably monochromatic to maximize the resolution of the device, and which typically defines the X-Y frame of reference. Alternatively, the CCD may be adapted to receive color images. The detection optics 60 receives image data from the main optics 41 and the image processor 24 determines the depth Z values for each X-Y point illuminated on the object 26 based on this image data. In this manner, a manipulable three-dimensional numerical entity E comprising the surface coordinates of the object 26.

The device 100 further comprises color illuminating means, such as for example a tri-color sequence generator 74, for selectively illuminating the object 26 with suitable colors, typically Green, Red and Blue, and for each such monochromatic illumination, a two dimensional image of the object 26 is captured by the detection optics 60. The processor 24 then processes the three differently colored monochromatic images and combines the same to provide a full color 2D image of the object. The device 100 is configured for providing color data for an array of X-Y points that is according to the same frame of reference as the X-Y array used for obtaining the 3D entity.

Figure 2C:
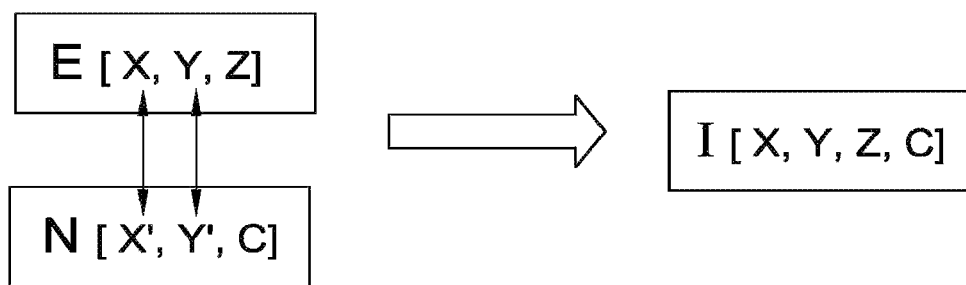

The processor 24 aligns the 2D color image with the 3D entity previously created, and then provides color values to this entity by mapping color values to the entity at aligned X-Y points. Such alignment is straightforward because both the 3D data and the 2D color data are referenced to the same X-Y frame of reference. Referring to FIGS. 2A, 2B, 2C, the mapping procedure is performed as follows. A three-dimensional numerical entity E is obtained by-determining depth Z-values for a grid of X-Y points, illuminated via main optics 41 and determined by image processor 24. The entity E thus comprises an array of (X, Y, Z) points, as illustrated in FIG. 2A. The X-Y plane of entity E is substantially parallel to the sensing face of the image sensing means of the detection optics 60, typically a CCD. Almost concurrently, i.e., either just before or just after the readings for determining the 3D entity E are obtained by the detection optics 60, a 2D color image of the object 26 is taken using the same detection optics 60, at substantially the same relative spatial disposition between the detection optics 60 and the object 26, FIG. 2B. If a monochromatic CCD is used, the 2D color image obtained is a composite created from three separate monochromatic images, each provided by illuminating the object 26 with a different color, such as for example red, green and blue. The 2D color image thus corresponds to another entity N comprised of the location and color value of each pixel forming this image, (X', Y', C). The X'-Y' coordinates' of the pixels are on a plane substantially parallel to the X-Y plane of the entity E, and furthermore these coordinates represent substantially the same part of the object 26 as the X-Y coordinates of entity E. The reason for this is that the optical information that is used for creating both the 3D entity E and the color 2D entity N are obtained almost simultaneously with a very small time interval therebetween, and typically there is insufficient time for any significant relative movement between the image plane of the detection optics 60 and the object 26 to have occurred between the two scans. Thus, similar X-Y and X'-Y' coordinates in the entities E and N, respectively, will substantially represent the same part of the object 26. Accordingly, the color value C of each pixel of entity N can be mapped to the data point of entity E having X-Y coordinates that are the same as the X'-Y' coordinates of the pixel, whereby to create another entity I comprising surface coordinate and color data, (X, Y, Z, C), as illustrated in FIG. 2C.

Were the relative angle and disposition between the plane of the sensing face of the detection optics 60 with respect to the object 26 change significantly between the 2D and the 3D scans, then the X-Y coordinates of entity E having similar values to the X'-Y' coordinates of entity N could correspond to different parts of the object 26, and thus it may then be difficult to map the color values of entity N to entity E. However, if only a small movement between the detection optics 60 with respect to the object 26 occurs, particularly involving a relative translation or a rotation about the depth direction (Z), but substantially no change in the angular disposition between detection optics 60 and the object 26 about the X or Y axes, it may still be possible to map the color values of entity N to entity E, but first an alignment procedure must be followed.

Figure 3:
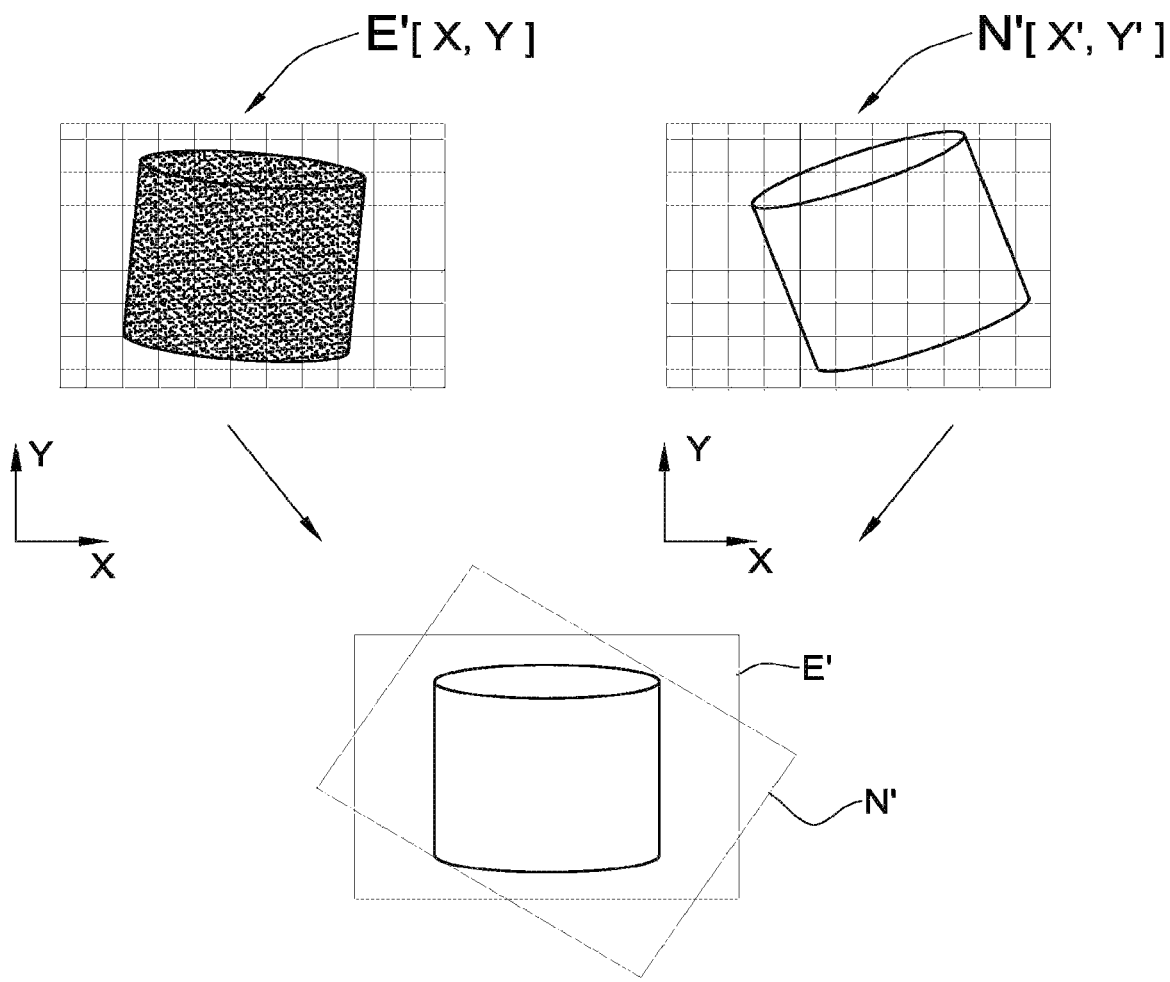
FIG. 3 graphically illustrates an alignment procedure according to the invention for aligning the X-Y coordinates of a three dimensional monochrome entity with corresponding coordinates of a two dimensional color entity.

Referring to FIG. 3, such an alignment procedure may be based on optical character recognition (OCR) techniques. In the X-Y plane, the X-Y coordinates of entity E can be divided up into two groups, one group comprising Z values corresponding to the depth of the object, and a second group for which no reasonable Z value was found and this group corresponds to the background relative to object 26. The profiles of shapes represented by the X-Y coordinates of the first group of entity E, herein referred to as another entity E', are then optically compared with profiles of shapes corresponding to the X'-Y' coordinates of entity N, herein referred to as another entity N'. Accordingly, entity E' is translated or rotated (coplanarly) with respect to entity N' until a best fit between the optical shapes between the two entities is obtained, using OCR techniques that are well known in the art. Typically, the image processor, or another computer, will attempt to align the outer border of the object 26 as seen along the Z-axis and encoded in entity E with optical elements in the 2D color image encoded in entity N. Thereafter, the color value C of each X'-Y' coordinate of entity N is mapped to the appropriate data point of entity E having the aligned X-Y coordinates corresponding thereto. The color mapping operation to create entity I may be executed by any suitable microprocessor means, typically processor 24 of the device 100 (FIG. 4B).

The main optics 41, main illumination source 31, detection optics 60 and image processor 24 are now described with reference to FIGS. 4A and 4B which illustrate, by way of a block diagram an embodiment of a system 20 for confocal imaging of a three dimensional structure according to WO 00/08415 assigned to the present assignee, the contents of which are incorporated herein. Alternatively, any suitable confocal imaging arrangement may be used in the present invention.

The system 20 comprises an optical device 22 coupled to a processor 24. Optical device 22 comprises, in this specific embodiment, a semiconductor laser unit 28 emitting a laser light, as represented by arrow 30. The light passes through a polarizer 32 which gives rise to a certain polarization of the light passing through polarizer 32. The light then enters into an optic expander 34 which improves the numerical aperture of the light beam 30. The light beam 30 then passes through a module 38, which may, for example, be a grating or a micro lens array which splits the parent beam 30 into a plurality of incident light beams 36, represented here, for ease of illustration, by a single line. The operation principles of module 38 are known per se and the art and these principles will thus not be elaborated herein.

The optical device 22 further comprises a partially transparent mirror 40 having a small central aperture. It allows transfer of light from the laser source through the downstream optics, but reflects light travelling in the opposite direction. It should be noted that in principle, rather than a partially transparent mirror other optical components with a similar function may also be used, e.g. a beam splitter. The aperture in the mirror 40 improves the measurement accuracy of the apparatus. As a result of this mirror structure the light beams will yield a light annulus on the illuminated area of the imaged object as long as the area is not in focus; and the annulus will turn into a completely illuminated spot once in focus. This will ensure that a difference between the measured intensity when out-of- and in-focus will be larger. Another advantage of a mirror of this kind, as opposed to a beam splitter, is that in the case of the mirror internal reflections which occur in a beam splitter are avoided, and hence the signal-to-noise ratio improves.

The unit further comprises a confocal optics 42, typically operating in a telecentric mode, a relay optics 44, and an endoscopic probing member 46. Elements 42, 44 and 46 are generally as known per se. It should however be noted that telecentric confocal optics avoids distance-introduced magnification changes and maintains the same magnification of the image over a wide range of distances in the Z direction (the Z direction being the direction of beam propagation). The relay optics enables to maintain a certain numerical aperture of the beam's propagation.

The endoscopic probing member 46 typically comprises a rigid, light-transmitting medium, which may be a hollow object defining within it a light transmission path or an object made of a light transmitting material, e.g. a glass body or tube. At its end, the endoscopic probe typically comprises a mirror of the kind ensuring a total internal reflection and which thus directs the incident light beams towards the teeth segment 26. The endoscope 46 thus emits a plurality of incident light beams 48 impinging on to the surface of the teeth section.

Incident light beams 48 form an array of light beams arranged in an X-Y plane, in the Cartesian frame 50, propagating along the Z axis. As the surface on which the incident light beams hits is an uneven surface, the illuminated spots 52 are displaced from one another along the Z axis, at different $(X_i, Y_i)$ locations. Thus, while a spot at one location may be in focus of the optical element 42, spots at other locations may be out-of-focus. Therefore, the light intensity of the returned light beams (see below) of the focused spots will be at its peak, while the light intensity at other spots will be off peak. Thus, for each illuminated spot, a plurality of measurements of light intensity are made at different positions along the Z-axis and for each of such $(X_i, Y_i)$ location, typically the derivative of the intensity over distance (Z) will be made, the $Z_i$ yielding maximum derivative, $Z_0$, will be the in-focus distance. As pointed out above, where, as a result of use of the punctured mirror 40, the incident light forms a light disk on the surface when out of focus and a complete light spot only when in focus, the distance derivative will be larger when approaching in-focus position thus increasing accuracy of the measurement.

The light scattered from each of the light spots includes a beam travelling initially in the Z-axis along the opposite direction of the optical path traveled by the incident light beams. Each returned light beam 54 corresponds to one of the incident light beams 36. Given the unsymmetrical properties of mirror 40, the returned light beams are reflected in the direction of the detection optics 60. The detection optics 60 comprises a polarizer 62 that has a plane of preferred polarization oriented normal to the plane polarization of polarizer 32. The returned polarized light beam 54 pass through an imaging optic 64, typically a lens or a plurality of lenses; and then through a matrix 66 comprising an array of pinholes. CCD camera has a matrix or sensing elements each representing a pixel of the image and each one corresponding to one pinhole in the array 66.

The CCD camera is connected to the image-capturing module 80 of processor unit 24. Thus, each light intensity measured; in each of the sensing elements of the CCD camera is then grabbed and analyzed, in a manner to be described below, by processor 24.

Unit 22 further comprises a control module 70 connected to a controlling operation of both semi-conducting laser 28 and a motor 72. Motor 72 is linked to telecentric confocal optics 42 for changing the relative location of the focal plane of the optics 42 along the Z-axis. In a single sequence of operation, control unit 70 induces motor 72 to displace the optical element 42 to change the focal plane location and then, after receipt of a feedback that the location has changed, control module 70 will induce laser 28 to generate a light pulse. At the same time, it will synchronize image-capturing module 80 to grab data representative of the light intensity from each of the sensing elements. Then in subsequent sequences the focal plane will change in the same manner and the data capturing will continue over a wide focal range of optics 44.

Image capturing module 80 is connected to a CPU 82, which then determines the relative intensity in each pixel over the entire range of focal planes of optics 42, 44. As explained above, once a certain light spot is in focus, the measured intensity will be maximal. Thus, by determining the Z, corresponding to the maximal light intensity or by determining the maximum displacement derivative of the light intensity, for each pixel, the relative position of each light spot along the Z-axis can be determined. Thus, data representative of the three-dimensional pattern of a surface in the teeth segment, can be obtained. This three-dimensional representation may be displayed on a display 84 and manipulated for viewing, e.g. viewing from different angles, zooming-in or out, by the user control module 86 (typically a computer keyboard).

The device 100 further comprises means for providing a 2D color image of the same object 26, and any suitable technique may be used for providing the color image. A number of such techniques are described below.

Figure 4A:
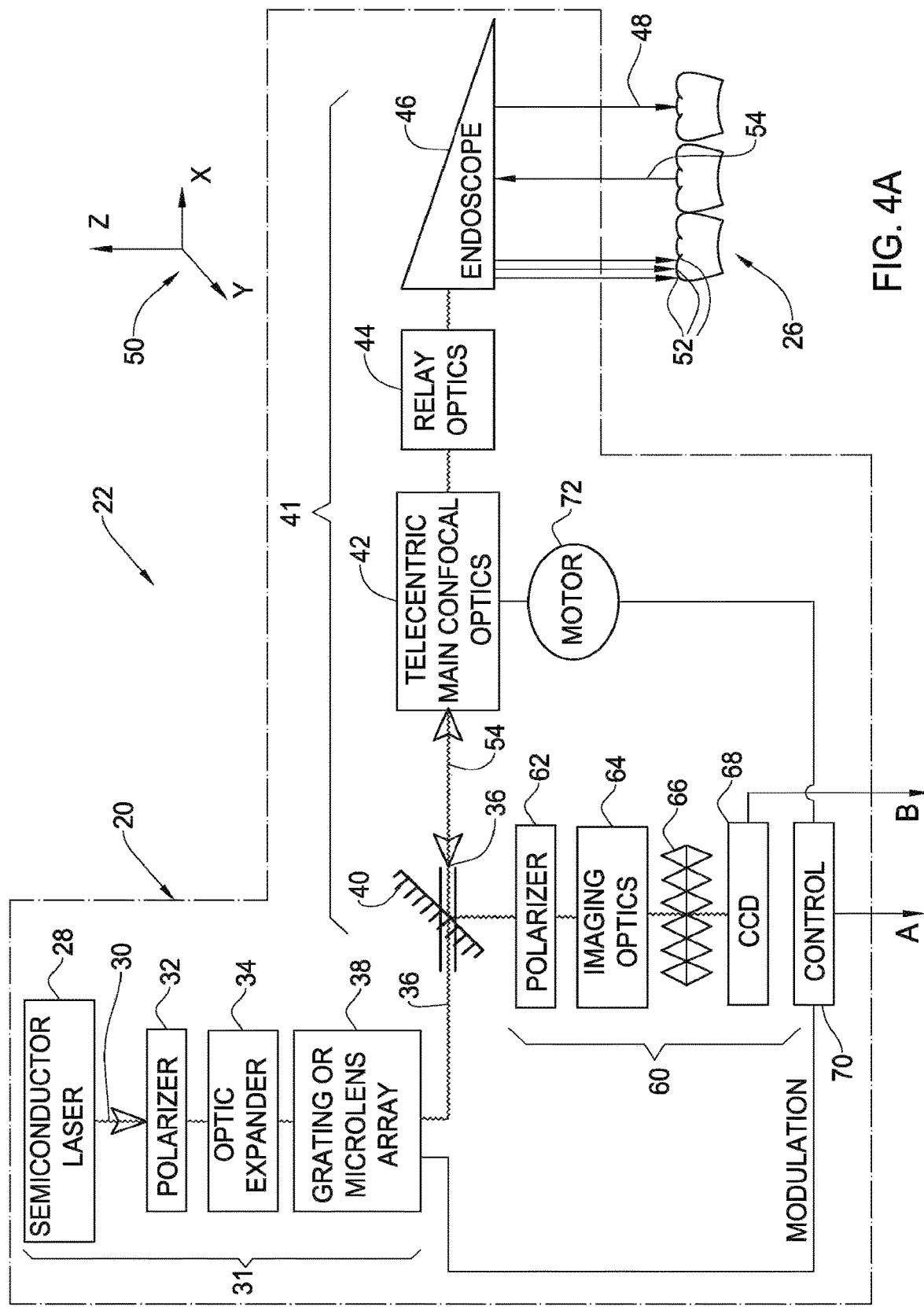
FIGS. 4A and 4B schematically illustrate the main elements of a portion of a device used for providing a three dimensional monochrome entity.
Figure 4B:
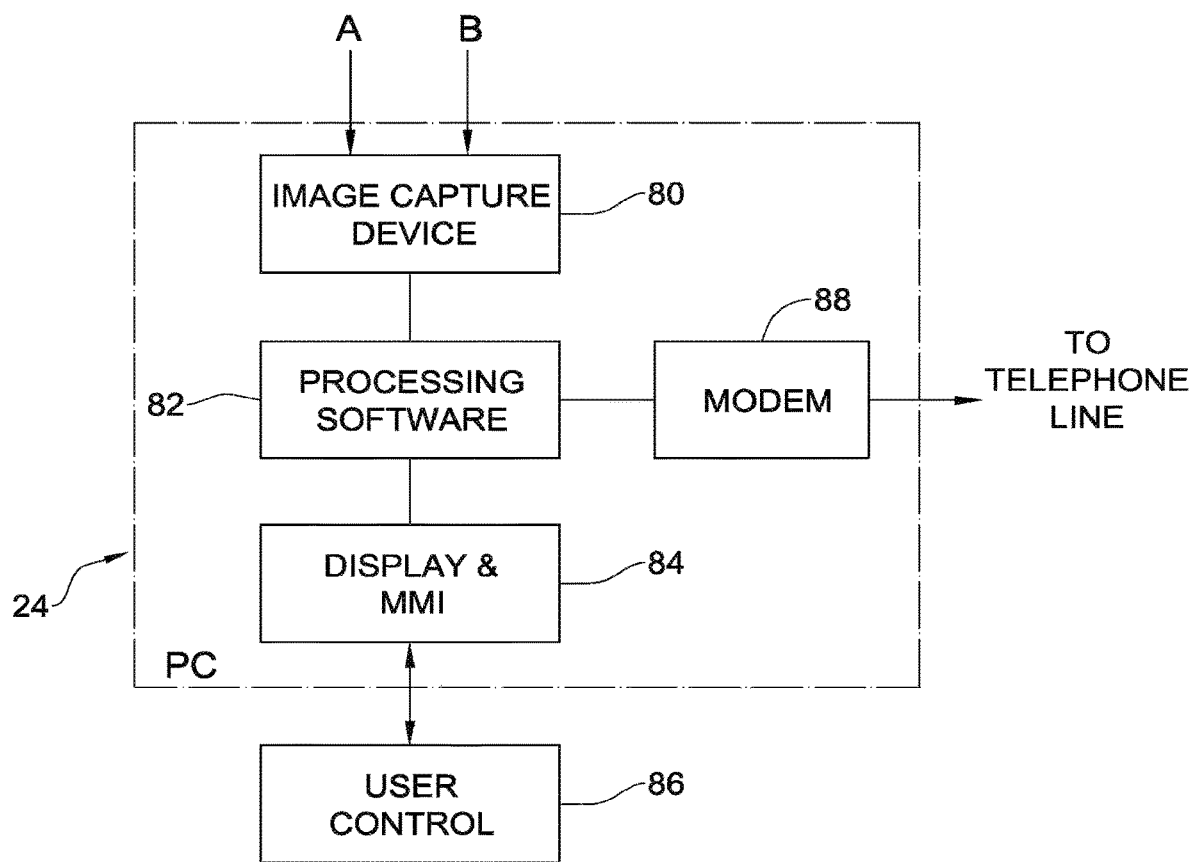

The first technique is based on illuminating the object 26 sequentially with three different colored lights such as red, green and blue, and capturing a monochromatic image corresponding to each color via CCD 68 and the image capture device 80 (see FIGS. 4A, 4B). Referring to FIG. 1, tri-color light sources 71, i.e., one or more light sources that provide illuminating radiations to the object 26 in a plurality of different colors, are coupled to a tri-color sequence generator 74, which are suitably controlled by the processing unit 24 to provide the three colored illuminations via delivery optics 73 in a predetermined sequence. The colored illuminations are provided at a relative short time interval, typically in the range of about 0 to 100 milliseconds, in some cases being in the order of 50 milliseconds or 20 milliseconds, for example, with respect to the 3D scan, directly before or after the same. Suitable processing software 82 combines the three images to provide a 2D color image comprising an array of data points having location (X, Y) and color (C) information for each pixel of the 2D color image.

Figure 5A:
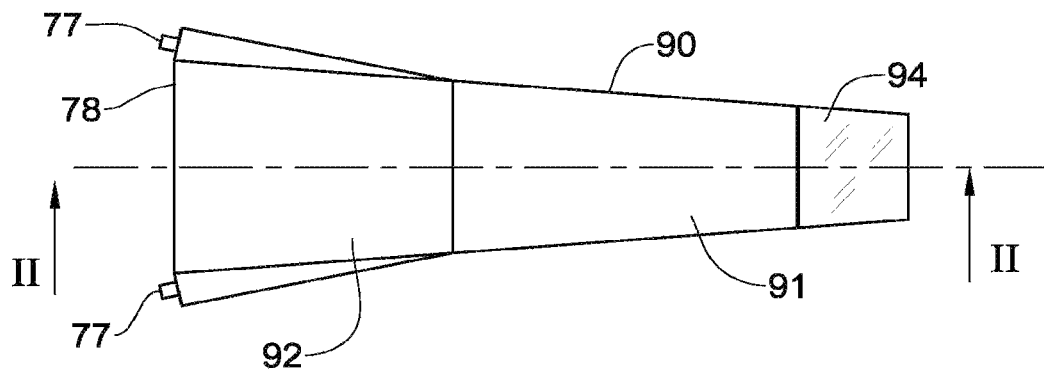
FIGS. 5A, 5B, 5C illustrate in plan view, side view and isometric view, respectively, a probe used in first embodiment of the device of FIG. 1 to provide a two dimensional color entity.
Figure 5B:
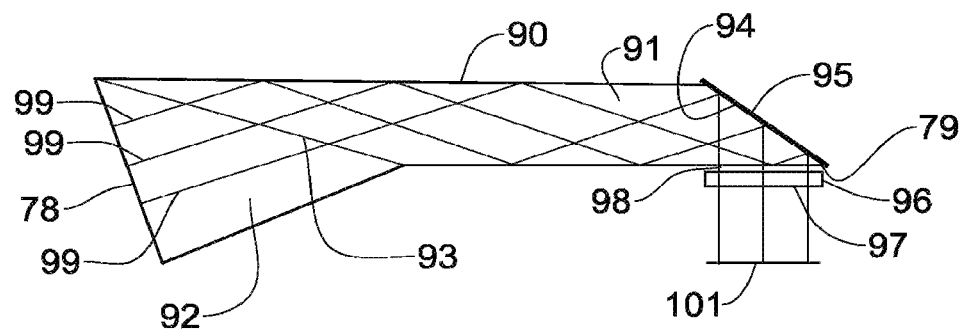
Figure 5C:
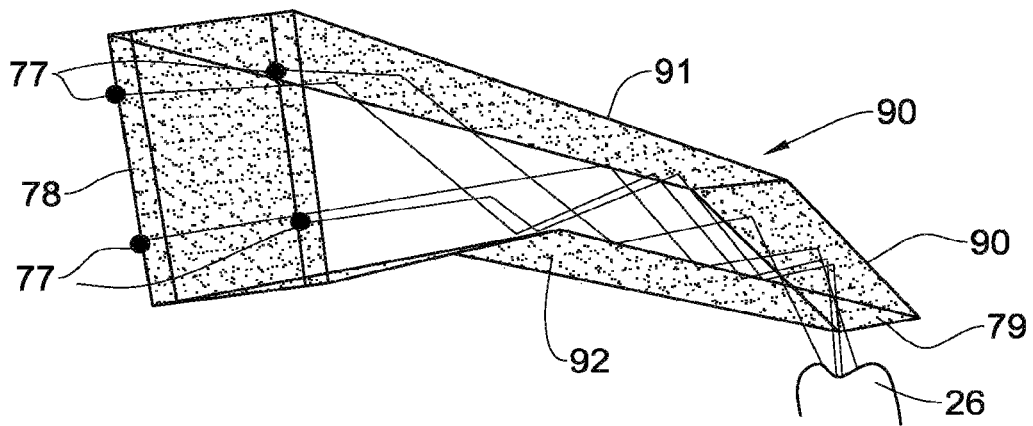

According to a first embodiment of the device 100, the delivery optics 73 is integral with endoscope 46, which is in the form of a probing member 90, as illustrated in FIGS. 5A, 5B and 5C. The probing member 90 is made of a light transmissive material, typically glass and is composed of an anterior segment 91 and a posterior segment 92, tightly glued together in an optically transmissive manner at 93. Slanted face 94 is covered by a totally reflective mirror layer 95. Glass disk 96 defining a sensing surface 97 may be disposed at the bottom in a manner leaving an air gap 98. The disk is fixed in position by a holding structure which is not shown. Three light rays are 99 from the main optics 42 are represented schematically. As can be seen, they bounce at the walls of the probing member at an angle in which the walls are totally reflective and finally bounce on mirror 95 and reflected from there out through the sensing face 97. The light rays focus on focusing plane 101, the position of which can be changed by the focusing optics (not shown in this figure). The probe member 90 comprises an interface 78 via which optical communication is established with the relay optics 44 and the remainder of the, device 100. The probe 90 further comprises a plurality of tri-color LED's 77, for providing the colored illumination to the object 26.

The LED's 77 typically comprise different LED's for providing blue radiation and green radiation when red illuminating radiation is used as the illumination source 31 for the main optics 41 when creating the 3D entity. Alternatively, if a blue illuminating radiation is used as the illumination source 31, the LED's 77 may comprise green and red LED's, and if a green illuminating radiation is used as the illumination source 31, LED's 77 may comprise blue and red LED's.

The tri-color LED's 77 are each capable of providing an illumination radiation in one of three colors, typically red, green or blue, as controlled via the tri-color sequence generator. Alternatively, a plurality of LED's in three groups, each group providing illumination in one of the desired colors, may be provided. The LED's 77 are located at the periphery of the interface 78 such that the LED's do not interfere with the other optical operations of the device 100. In particular such operations include the transmission of the illuminating radiation for the confocal focusing operations, and also the transmission of reflected light from the object 26 to the main optics 41 to provide the 3D entity or the 2D color entity. The LED's are mounted substantially orthogonally with respect to the interface 78, and thus, as illustrated in FIG. 5C, light from each of the LED's 77 is transmitted by internal reflection with respect to the walls of the probe 90, to the user interface end 79 of the probe.

Figure 6:
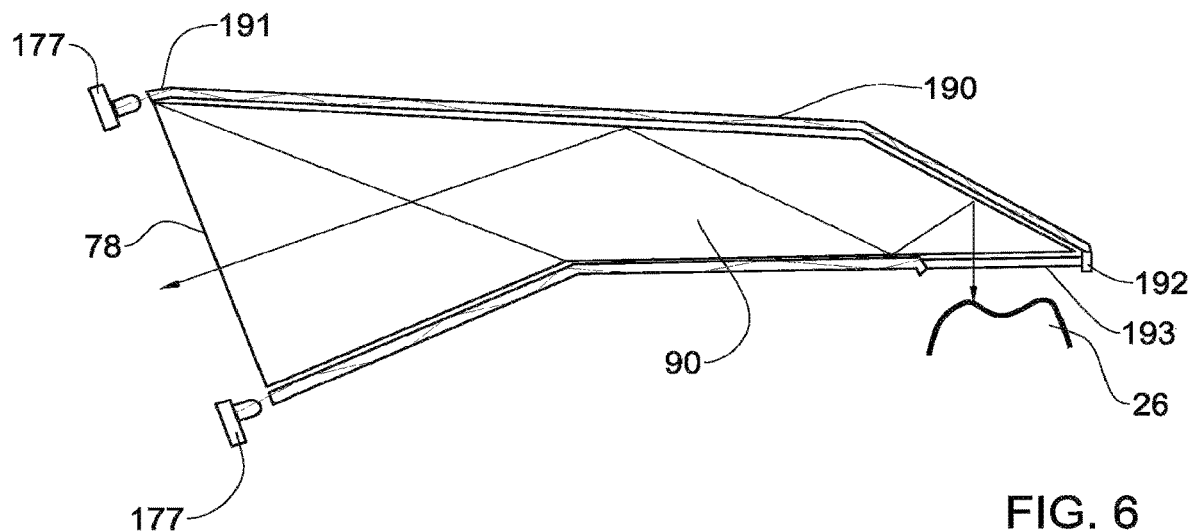
FIG. 6 illustrates in side view a sheath for a probe used in second embodiment of the device of FIG. 1 to provide a two dimensional color entity.

According to a second embodiment of the device 100, the endoscope 46, is also in the form of a probing member 90, substantially as described with respect to the first embodiment, but with the difference that there are no LED's directly mounted thereon at the interface 78, mutatis mutandis. In the second embodiment the delivery optics 73 is in the form of a disposable sleeve, shroud or sheath 190 that covers the outer surface the probing member 90, as illustrated in FIG. 6. The sheath 190 is made from a waveguiding material, such as an acrylic polymer for example, capable of transmitting an illuminating radiation from the upstream face 191 of the sheath 190 therethrough and to the downstream face 192 thereto. The upstream face 191 is in the form of a peripheral surface around the interface 78. The downstream face 192 is formed as a peripheral projection surrounding a window 193 comprised in said sheath 190. The window 193 is in registry with the user interface end 79 of the probe 90. A plurality of tri-color LED's 177 for providing the colored illumination to the object 26 are mounted on the device 100 just upstream of the sheath 190. The tri-color LED's 177 are each capable of providing an illumination radiation in one of three colors, typically red, green or blue, as controlled via the tri-color sequence generator 74. Alternatively, a plurality of LED's in three groups, each group providing one colored illumination, may be provided. The LED's 177 are located outside of the main optics of the device 100, and thus the LED's do not interfere with the other optical operations of the device 100 in particular including the transmission of the illuminating radiation for the confocal focusing operations, or in the transmission of reflected light from the object 26 to provide the 3D entity or the 2D color entity. The LED's are mounted substantially opposite to the upstream face 191, and thus, as illustrated in FIG. 6, light from each of the LED's 177 is transmitted by the waveguiding sheath 190 to downstream face 192 and thence to the object 26. In this embodiment, the sheath 190 is particularly useful in maintaining hygienic conditions between one patient and the next, and avoids the need for sterilizing the probe 90, since the sheath may be discarded after being used with one patient, and replaced with another sterilised sheath before conducting an intra-oral cavity survey with the next patient.

In either one of the first or second embodiments, or variations thereof, a red laser may be used as the illumination source 28 for the main optics when creating the 3D entity. As such, this illumination means may also be used to obtain the red monochromatic image for the creation of the 2D color image, by illuminating the object 26 and recording the image with the optical detector 60. Accordingly, rather than tri-color LED's or LED's or three different colors, it is only necessary to provide LED's adapted to provide only the remaining two colors, green and blue. A similar situation arises if the illumination source for the main optics 41 is a green or blue laser, wherein illuminating radiations in only the remaining two colors need to be provided, mutatis mutandis.

In these embodiments, the positioning of the illumination sources at the upstream end of the probe 90 where there is ample room rather than at the patient interface end 79 where space is tight.

Figure 7A:
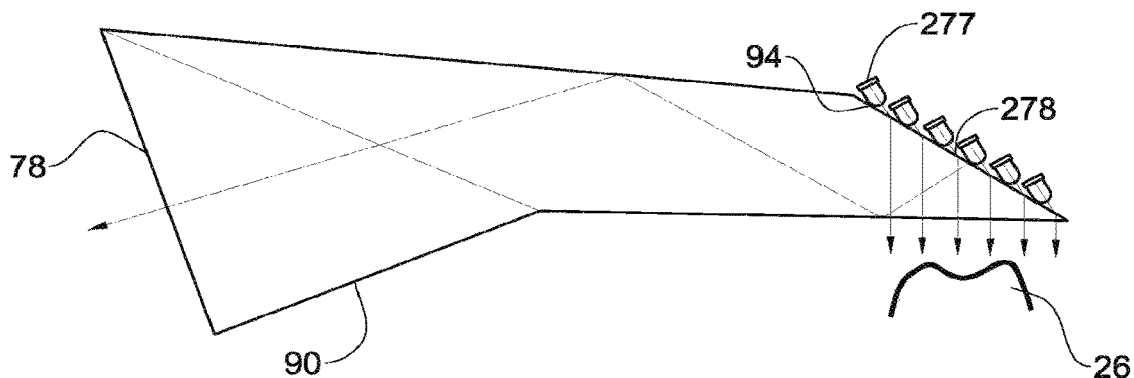
FIG. 7A illustrates in side view a probe used in third embodiment of the invention to provide a two dimensional color entity.
Figure 7B:
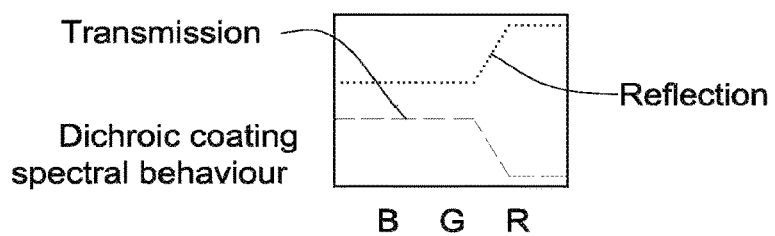
FIG. 7B illustrates the transmission and reflection characteristics of a typical dichroic coating used in the probe of FIG. 7A.

According to a third embodiment of the device 100, the endoscope 46 is also in the form of a probing member 90, substantially as described with respect to the second embodiment with the following differences, mutatis mutandis. As illustrated in FIG. 7A, in the third embodiment the delivery optics 73 comprises a plurality of LED's 277 for providing the colored illumination to the object 26. In this embodiment, a red laser is used as the illumination source for the main optics when creating the 3D entity. As such, this illumination means is also used to obtain the red monochromatic image for the creation of the 2D color image. Thus, the LED's 277 are each capable of providing an illumination radiation in either green or blue, as controlled via the tri-color sequence generator 74. The LED's 277 are located on the outer side of slanted face 94, and thus the LED's do not interfere with the other optical operations of the device 100 in particular including the transmission of the illuminating radiation for the confocal focusing operations, or in the transmission of reflected light from the object 26 to provide the 3D entity or the 2D color entity. The slanted face 94 comprises a dichroic coating 278 on the outer side thereof, which has relatively high reflectivity and low transmission properties with respect to red light, while having substantially high transmission characteristics for blue light and green light, as illustrated in FIG. 7B. Thus, as illustrated in FIG. 7A, light from each of the blue or green LED's 277 is transmitted, in turn, through the dichroic coating to interface 79 and thence to the object 26, as controlled by the generator 74. At the same time the dichroic coating permits internal reflection of the red radiation from the main optics 41 to the interface 79 and object 26, and thus allows the 3D scan to be completed, as well as allowing the red monochromatic image of the object 26 to be taken by the device 100. Optionally, rather than employing blue and green LED's, tricolor LED's may be used, and properly synchronized to illuminate with either green or blue light as controlled by generator 74. Alternatively, the illumination source for the main optics 41 may be a green or blue laser, in which case the LED's are each capable of providing illumination in the remaining two colors, and in such cases the dichroic coating is adapted for allowing transmission of these remaining two colors while providing substantially high reflection for the illuminating laser of the main optics, in a similar manner to that described above for the red laser, mutatis mutandis.

Figure 8:
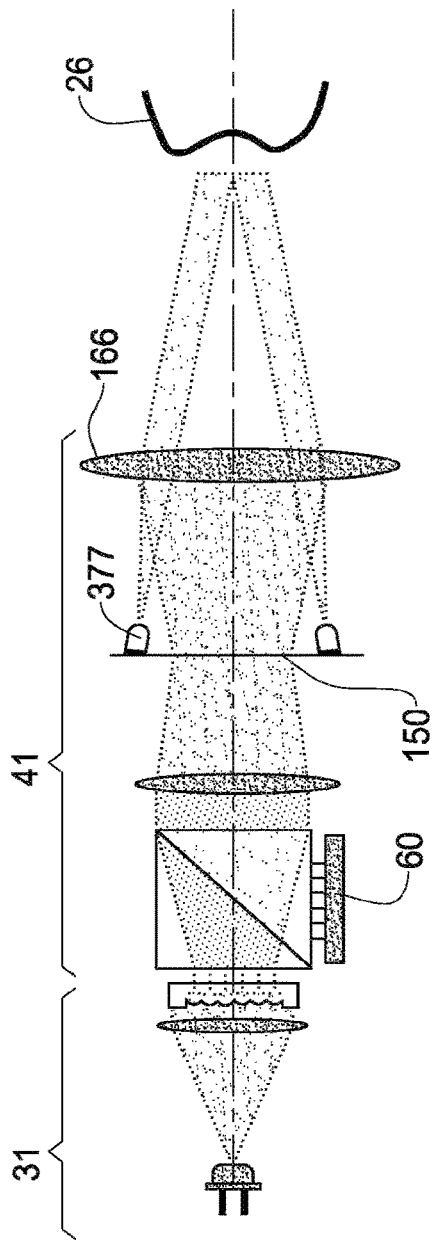
FIG. 8 illustrates in side view the general arrangement of the main elements used in fourth embodiment of the device of FIG. 1 to provide a two dimensional color entity.

In a fourth embodiment of the device 100, and referring to FIG. 8, tri-color illumination is provided within the main focal optics 42, in particular at the confocal system aperture stop, and facing the objective lens of the system. An advantage provided by this form of illumination is that the tri-color illumination illuminates the object 26 through the downstream objective lens 142 in nearly collimated light, and thus the object illumination is highly uniform. The tri-color light sources 377 may be mounted statically on the physical aperture stop at the aperture stop plane 150, or alternatively they may be mounted on a retracting aperture stop, which also serves to stop down the system aperture in preview mode. In this embodiment, by placing the tri-color light sources 377 at the aperture stop plane, wherein the light beam from the illumination source 31 narrows to a minimum within the main optics 41, the external dimensions of the device 100 may still remain relatively compact.

Figure 9:
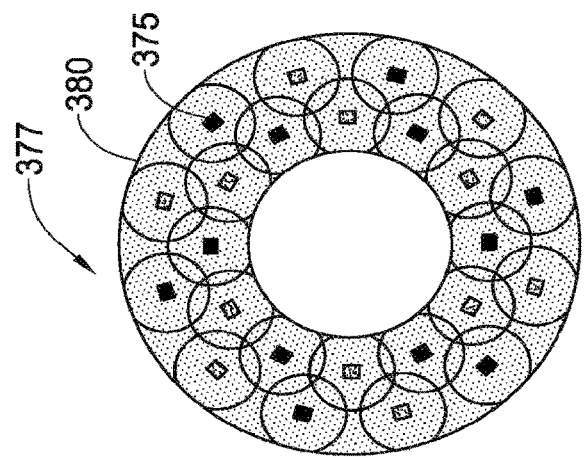
FIG. 9 illustrates an LED arrangement used with the embodiment of FIG. 8.

Referring to FIG. 9, the tri-color light sources 377 may comprise, for example, a plurality of tri-color LED's 385 mounted onto a bracket 380. The bracket 380 is typically annular, having a central aperture to allow illumination light from the illuminating unit 31 to pass therethrough and to the object 26, and to allow light coming from the object 26 to pass therethrough and to the detection optics 60, without being affected by the bracket 380. At the same time, the bracket 380 positions the LED's in the required location upstream of objective lens 166. The LED's are arranged in a spaced radial and circumferential manner as illustrated in FIG. 9 to provide the most uniform illumination of the object 26 possible with this arrangement. Typically, a red laser is used as the illumination source 31 for the main optics 41 when creating the 3D entity. As such, and as in other embodiments, this illumination means is also used to obtain the red monochromatic image for the creation of the 2D color image. Thus, the LED's 385 are each capable of providing an illumination radiation in either green or blue, as controlled via the tri-color sequence generator 74. Alternatively, the illumination source for the main optics 41 may be a green or blue laser, in which case the LED's 385 are each capable of providing illumination in the remaining two colors, in a similar manner to that described above for the red laser, mutatis mutandis. Optionally, rather than employing blue and green LED's, tricolor LED's may be used, and properly synchronized to illuminate with either green or blue light as controlled by generator 74. Further optionally, the LED's 385 may be used to provide, sequentially, all the required colored illuminations, typically red, green and blue. Alternatively, the LED's 385 each provide illumination in one of at least three colors. Thus, some of the LED's 385 provide a blue illumination, while other LED's 385 provide green illumination, while yet other LED's 385 provide red illumination.

The device 100 according to a variation of the fourth embodiment is further adapted for providing improved precision of the color data obtained therewith. In this connection, the device 100 according to this variation of the fourth embodiment is adapted such that the tri-color light sources 377 each illuminate the object 26 with as wide a depth of field as possible, i.e., at a low numerical aperture. Thus, each set of light sources 377 of the same color, for example blue, illuminates a particular depth of the object 26 in the z-direction while substantially in focus. In contrast, the numerical aperture of the confocal system itself is relatively high to maximize accuracy of the depth measurements, and thus provides a relatively narrower depth of field.

Advantageously, the optical system downstream of the light sources 377, in this embodiment the objective lens 166, is chromatic, and in particular maximizes the chromatic dispersion therethrough. Alternatively or additionally, a chromatic dispersion element, for example an optically refractive block of suitable refractive index, may be provided along the optical path between the light sources 377 and the object 26. Thus, each one of the different-colored light sources 377 illuminates a different portion of the object 26 along the z-direction. The light sources 377 providing the blue illumination illuminate in focus a portion of the object 26 closest to the device 100, and the light sources 377 providing the red illumination illuminate in focus a portion of the object 26 furthest from the device 100. At the same time, the light sources 377 providing the green illumination illuminate in focus a portion of the object 26 intermediate the blue and red portions, and a non-illuminated gap may exists between the red and green, and between the green and blue illuminated portions, the depth of these gaps depending on the dispersion characteristics of the downstream optics. Advantageously, the light sources 377 are also adapted for providing illumination in colors intermediate in wavelengths such as to illuminate the aforesaid gaps in focus. Thus, the LED's 385 may be adapted for providing both such additional colored illumination, or some of the LED's 385 may be adapted to provide colored illumination at a first intermediate wavelength, while another set of LED's 385 may be adapted to provide colored illumination at a second intermediate wavelength. For example, the first intermediate wavelength provides an illumination in aqua, and thus illuminates in focus at least a part of the gaps between the blue and green illuminated focused zones of the object 26, while the second intermediate wavelength provides an illumination in amber, and thus illuminates in focus at least a part the gaps between the green and red illuminated focused zones. Of course, additional light sources may be used to provide further intermediate wavelengths and thus provide further depth cover illumination, in focus, of the object.

While the device 100 is used as a viewfinder, typically prior to taking a depth and color scan of the object 26, the above arrangement using at least five different colored illuminations at a low numerical aperture, enables a much clearer and focused real-time color image of the object 26 to be obtained. Thus when in operation in viewfinder mode (also known as "aiming mode", prior to the 3D scan event, while the dental practitioner is in the process of aiming the scanner onto the target dental surface, for example) the device 100 according to this variation of the fourth embodiment repeatedly illuminates the object 26 in cycles, wherein in each cycle the object 26 is separately illuminated in each of the five colors blue, aqua, green, amber, red, in quick succession, and each time a monochromatic image is obtained by the monochromatic image sensor in 60. Each set of five monochromatic images is then analysed to provide a composite color image, and this image is then displayed in substantially real time in the viewfinder display window in the control software, so that the succession of such composite images gives the appearance of a substantially real-time color video feed of the object 26.

Each of the monochrome images in any particular set corresponds to a particular illumination color or wavelength, and thus the zone(s) of the object 26 within the depth of field corresponding to this illumination will be in focus, while the other parts of the object 26 will appear out of focus. Thus, each such image in the aforesaid set of images will contain a portion which has high precision focused image of a part of the object, for the particular illumination wavelength.

In forming a composite image for each set of images, the images are combined in such a way as to maximize the precision of the focused image and corresponding color thereof. Thus, for example, suitable algorithms may be applied to each of the five images of a set to distinguish between the focused and unfocused the areas thereof. Such algorithms may employ, for example, techniques which apply FFT techniques to areas of the images, and which search for high frequency portions which correspond to focused areas. In any case, such algorithms, as well as software and hardware to accomplish the same are well known in the art. Then, the focused areas of each of the five images are merged to provide a monochrome composite substantially focused image of the object. Next, the images obtained using the red, green and blue illuminations are combined and converted to a corresponding luminescence/chroma (Y/C) image, and techniques for doing so are well known in the art. Finally, the luminescence component of the luminescence/chroma (Y/C) image is replaced with the aforesaid corresponding composite focus image, and the resulting new luminescence/chroma image is then transmitted to the display in the viewfinder.

For each set of images, prior to combining the corresponding red, green and blue images, these are preferably first scaled to compensate for magnification effects of the different wavelengths. Thus, the green image, and more so the blue image, needs to be scaled up to match the red image.

When the user is ready to take a depth and color scan of the object 26, having steered the device 100 into position with the aid of the viewfinder, the device 100 takes a depth scan in the z-direction as described herein, and either before or after the same, but in quick succession one with the other, takes a color scan in a similar manner to that described above for the viewfinder mode, mutatis mutandis. Subsequently, the color data and the depth data of the two scans can be combined to provide the full spatial and color data for the surface scanned.

Advantageously, one or more color scans may also be taken during the depth scan, and/or at the beginning and at the end of the depth scan. In one mode of operation, the depth scan is obtained by displacing the objective lends 166 along the z-direction in a continuous or stepped motion. Multiple color scans can then be obtained by associating the color sources 377 with the objective lens, so that these are also displaced along the z-direction. Accordingly, as the light sources 377 are moved in the z-direction towards the object 26 during the depth scan, at each different z-position in which a set of images is taken (concurrently with or alternately with the depth scan), each one of the colored illuminations—red, green, blue and intermediate wavelengths—illuminates a progressively deeper part of the object along the z-direction. Of course, in some cases it is possible that at the downstream end of the depth scan the green and red illuminations completely overshoot the object 26, and the corresponding images may be discarded or otherwise manipulated to provide a composite color image at this station. Thus, a plurality of color images can be obtained, each based on a different z-position, so that each illumination wavelength is used to illuminate in focus a different part (depth) of the object 26. Advantageously, suitable algorithms may be used to form a composite color image of the set of color images associated with a particular z-scan of the object 26 to provide even more precise and accurate color image, than can then be combined with the depth data.

Figure 10:
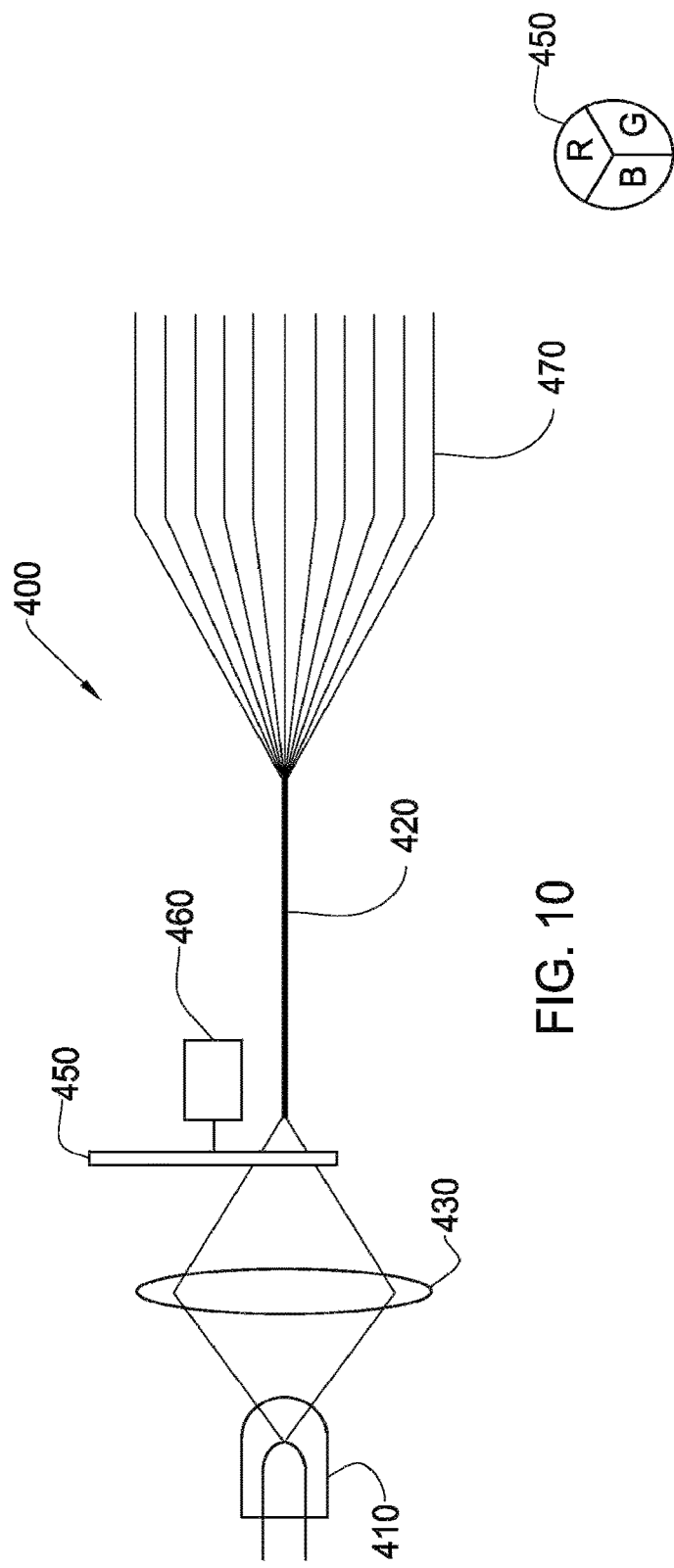
FIG. 10 illustrates an alternative illumination arrangement used with the embodiment of FIG. 8.
Figure 10A:
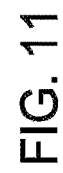
FIG. 10A illustrates details of the tri-color disc used with the illumination arrangement of FIG. 10.

Alternatively, and referring to FIG. 10, the tri-color light sources 377 may be replaced with a rotating filter illumination system 400. The system 400 comprises a while light source 410, such as for example white phosphorus InGaN LED's, and the light therefrom is focused onto an optical fiber bundle 420 by means of condenser optics 430. Between the condenser optics 430 and the fiber bundle 420 is provided a rotating tri-color filter 450. As best seen in FIG. 10A, the filter 450 is divided into three colored sections, comprising blue, green and red filters on adjacent sectors therein. The fiber bundle 420 is flared at the downstream end 470 to form the desired illumination pattern. Optionally, the downstream end 470 of the fibers may be mounted onto an annular bracket similar to bracket 380 illustrated in FIG. 9, at the apertures stop plane of the confocal optics. A suitable motor 460, typically a stepper motor for example, drives the rotating filter such as to sequentially present each colored filter to the light passing from the condenser optics 430 to the fiber bundle 420, as synchronized with the sequence generator 74 (FIG. 1) to enable the detection optics 60 to capture images of the object 26 when selectively illuminated with each of the three colors. Optionally, if a red, blue or green illuminating radiation is used as the illumination source 31 for the main optics 41 when creating the 3D entity, then the rotating filter 450 only requires to comprise the remaining two colors, as discussed above for similar situations regarding the LED's, mutatis mutandis.

Figure 11:
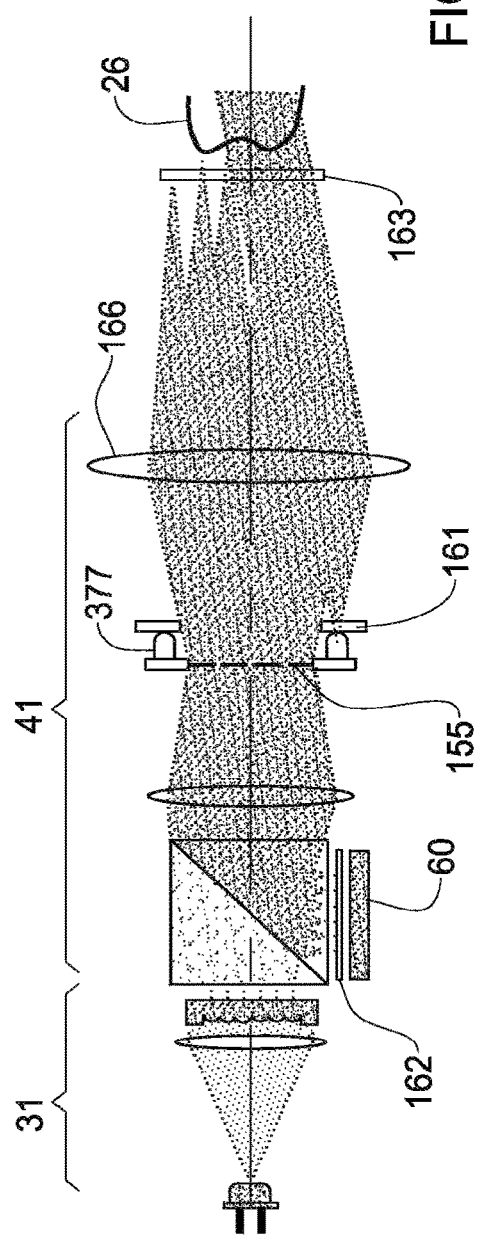
FIG. 11 illustrates in side view the general arrangement of the main elements used in fifth embodiment of the device of FIG. 1 to provide a two dimensional color entity.

A fifth embodiment of system 100 is substantially similar to the fourth embodiment as described herein, with the following difference, mutatis mutandis. In the fifth embodiment, and referring to FIG. 11, polarizers are provided at two locations in order to increase the image contrast. A first polarizing element 161 is located just downstream of the light sources 377 so as to polarize the light emitted from the light sources 377. A second polarizing element 162 is located just upstream of the image sensor of the detection optics 60, and is crossed with respect to the first polarizing element 161. Further, a quarter waveplate 163 is provided just upstream of the object 26, i.e. at the downstream end of the endoscope 46 (FIG. 4A). The first polarizing element 161 is typically annular, having a central aperture to allow illumination light from the illuminating unit 31 to pass therethrough and to the object, and to allow light coming from the object 26 to pass therethrough and to the detection optics 60, without being affected by the polarizing element 161. However, light that is reflected from the object 26 returns to the main confocal optics 42 in a crossed polarization state due to the effect of the quarter waveplate 163, and thus reaches the detection optics 60 at substantially full intensity. However, any light reflected from the objective lens 166 of the confocal optics 42 is reflected at the same polarization state, and is therefore filtered out by the crossed polarizing element 162. This arrangement serves as an effective signal to ghost enhancement system.

Figure 12:
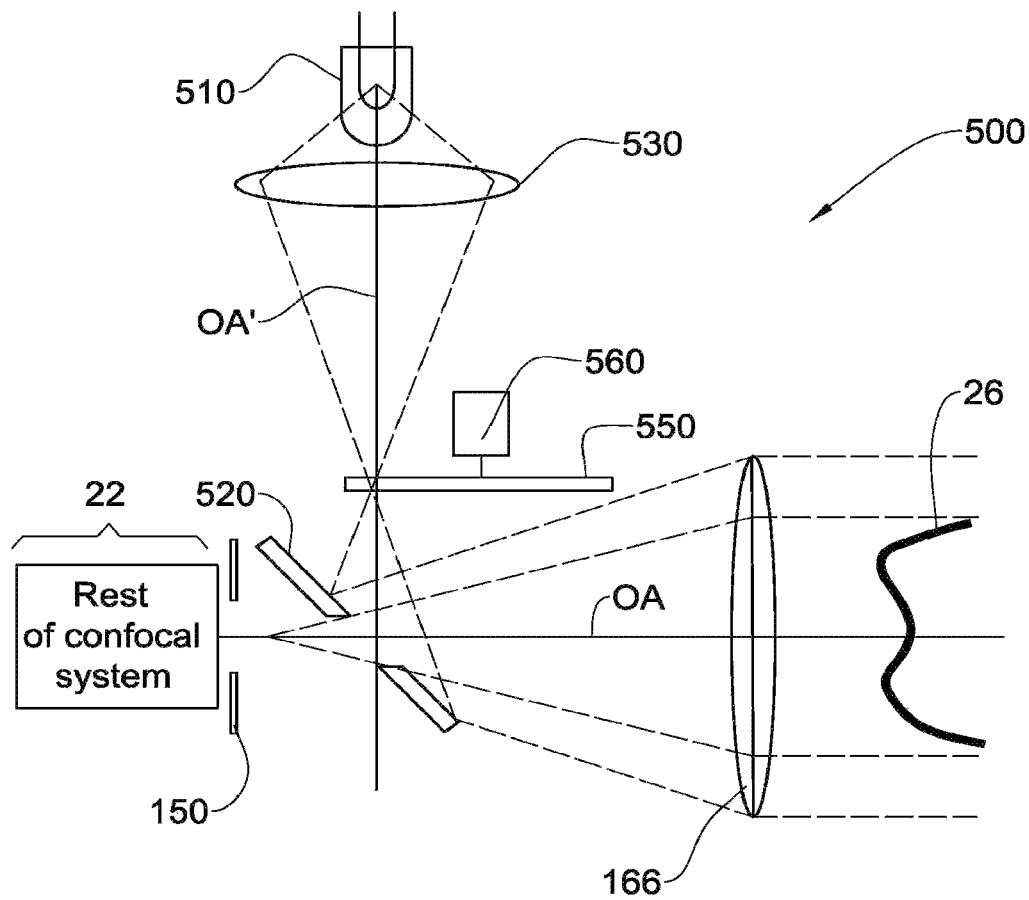
FIG. 12 illustrates in side view the general arrangement of the main elements used in sixth embodiment of the device of FIG. 1 to provide a two dimensional color entity.

A sixth embodiment of the system 100 is substantially as described for the fourth embodiment, with the following difference, mutatis mutandis. In the sixth embodiment, and referring to FIG. 12, the tri-color light sources 377 are replaced with a rotating filter illumination system 500. The system 500 comprises a while light source 510, such as for example white phosphorus InGaN LED's, and the light therefrom is focused onto a mirror 520 by means of condenser optics 530. Between the condenser optics 530 and the mirror 520 is provided a rotating tri-color filter 550, which is similar to the filter 450 illustrated in FIG. 11, and thus comprises three colored sections, comprising blue, green and red filters on adjacent sectors therein, and is actuated by motor 560. The optical axis OA of the confocal optics 41 is orthogonal to the optical axis OA' of the light source 510 and condenser optics 530. The mirror 520 is mounted between the aperture stop plane and the objective lens 166 of the confocal optics, and at an angle to the optical axis OA thereof and to the optical axis OA' of the light source 510 and condenser optics 530. The mirror 520 is typically annular, having a central aperture aligned with optical axis OA to allow illumination light from the illuminating unit 31 to pass therethrough and to the, object 26, and to allow light coming from the object 26 to pass therethrough and to the detection optics 60, without being affected by the mirror 520. At the same time, the mirror 520 has sufficient reflecting surface to reflect light from the source 510 via objective lens 166 and to the object 26. Optionally, if a red, blue or green illuminating radiation is used as the illumination source 31 for the main optics 41 when creating the 3D entity, then the rotating filter 550 only requires the remaining two colors, as discussed above for similar situations, mutandis mutandis.

Figure 13:
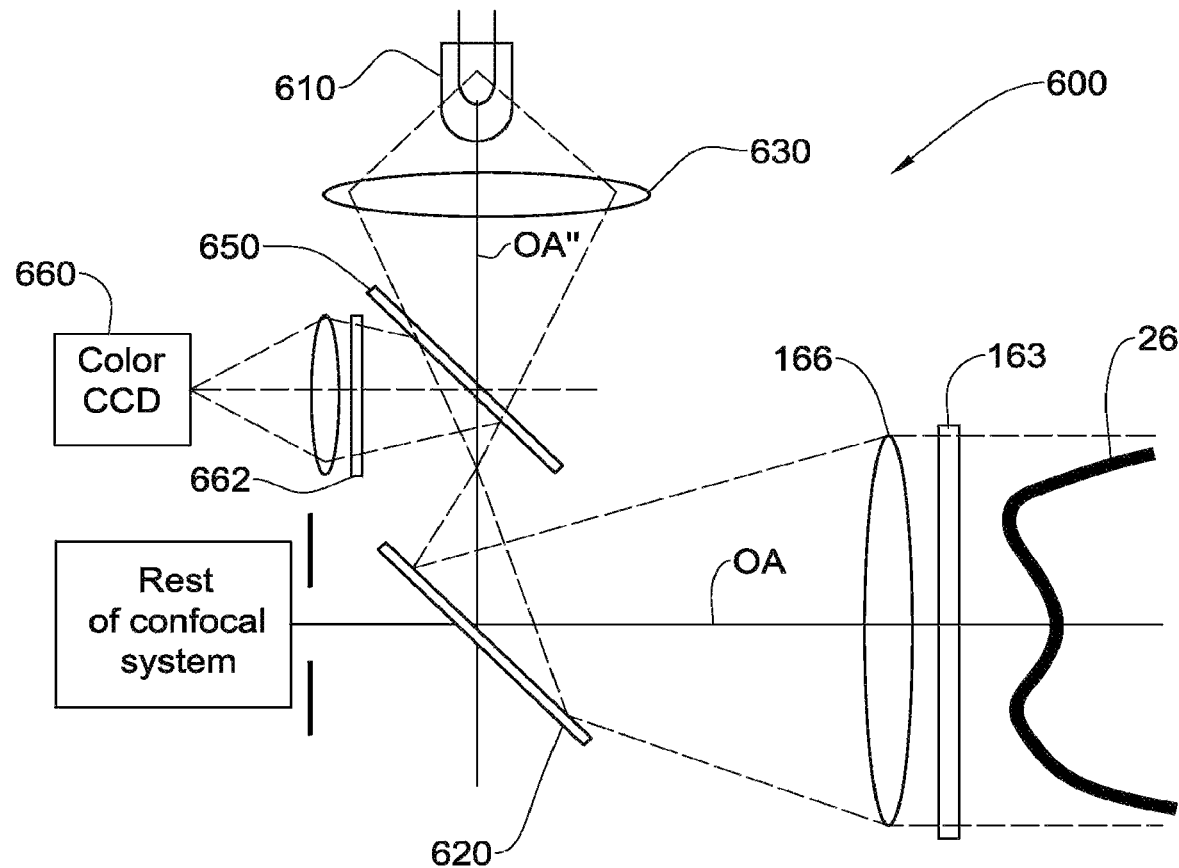
FIG. 13 illustrates in side view the general arrangement of the main elements used in seventh embodiment of the device of FIG. 1 to provide a two dimensional color entity.

According to a second technique for providing the aforesaid 2D color image, the object 26 is illuminated with a white light, and a color CCD is used for receiving the light reflected from the object 26. Thus, a seventh embodiment of the system 100 comprises a white light illumination system 600, illustrated in FIG. 13. The system 600 comprises a while light source 610, such as for example white phosphorus InGaN LED's, and the light therefrom is directed onto a flip mirror 620 via a polarizing beam splitter 650 by means of condenser optics 630. The optical axis OA of the confocal optics 41 is orthogonal to the optical axis OA" of the light source 610 and condenser optics 630. The mirror 620 is mounted between the aperture stop plane 155 and the objective lens 166 of the confocal optics, and at an angle to the optical axis OA thereof and to the optical axis OA" of the light source 610 and condenser optics 630.

The mirror 620 is adapted to flip away from optical axis OA when the device 100 is being used for obtaining the 3D entity E. This allows illumination light from the illuminating unit 31 to pass therethrough and to the object 26, and to allow light coming from the object 26 to pass therethrough and to the detection optics 60, without being affected by the mirror 620. When it is desired to take a 2D color image, the mirror 620 is flipped down to the position shown in FIG. 13. Polarizing beam splitter 650 that polarizes white light from the source 610 and allows the same to pass therethrough and to mirror 620, and thence to the object 26 via the confocal objective 166 and broadband quarter wave plate 163. Light that is reflected from the object 26 returns to the mirror 620 in a crossed polarization state due to the effect of the quarter waveplate 163, and thus reaches the color CCD 660 (and associated detection optics—not shown) at substantially full intensity. However, any light reflected from the objective lens 166 of the confocal optics 42 is reflected at the same polarization state, and is therefore filtered out by a crossed polarizing element 662 just upstream of the CCD 660. This arrangement serves as an effective signal to ghost enhancement system.

Alternatively, the CCD of the detection optics 60 is a color CCD and is also used for the 2D scan. In such a case, flipping mirror 620 is replaced with a fixed mirror having a central aperture similar to mirror 520, having a central aperture, as described for the sixth embodiment, mutatis mutandis.

In the seventh embodiment, the image capture device 80 and processing software 82 (FIG. 4b) automatically provide a 2D color image comprising an array of data points having location (X, Y) and color (C) information for each pixel of the image.

According to a third technique for providing the 2D color image, the object is illuminated with a white light, and the light reflected from the object 26 is passed sequentially through one of three different colored filters such as red, green and blue. Each time a monochromatic image corresponding to each color is captured via CCD 68 and the image capture device 80 (see FIGS. 4A, 4B). Suitable processing software 82 combines the three images to provide a 2D color image comprising an array of data points having location (X, Y) and color (C) information for each pixel of the image.

According to a fourth technique for providing the color image, the main illumination source 31 of device 100 comprises suitable means for providing the three different colored illuminations. In one embodiment, the illumination source 31 comprises three different lasers, each one providing an illumination radiation at a different desired color, red green or blue. In another embodiment, a suitable white light illumination means is provided, coupled to a suitable rotating tri-color filter, similar to the filters described above, mutatis mutandis. In each case, suitable control means are provided, adapted to illuminate the object 26 with each colored radiation in turn, and the 2D colored image is obtained in a similar fashion to that described above, mutatis mutandis. The object is also illuminated with one of the colored illuminations in order to provide the 3D surface topology data.

In each of the embodiments described herein, the illumination radiation that is used for obtaining the 2D color image is injected into the optical axis OA of the confocal optics 42 without affecting the operation thereof or degrading the 3D image capture.

The endoscope 46, the illumination unit 31, the main optics 41, color illumination 71 and tri-color sequence genetrator are preferably included together in a unitary device, typically a hand-held device. The device preferably includes also the detector optics 60, though the latter may be connected to the remainder of the device via a suitable optical link such as a fibre optics cable.

For all embodiments, the data representative of the surface topology and color, i.e., entity I, may be transmitted through an appropriate data port, e.g. a modem 88 (FIG. 4B), through any communication network, e.g. telephone line 90, to a recipient (not shown) e.g. to an off-site CAD/CAM apparatus (not shown).

By capturing, in this manner, an image from two or more angular locations around the structure, e.g. in the case of a teeth segment from the buccal direction, from the lingual direction and optionally from above the teeth, an accurate color three-dimensional representation of the teeth segment may be reconstructed. This may allow a virtual reconstruction of the three-dimensional structure in a computerized environment or a physical reconstruction in a CAD/CAM apparatus.

While the present device has been described in the context of a particular embodiment of an optical scanner that uses confocal focusing techniques for obtaining the 3D entity, the device may comprise any other confocal focusing arrangement, for example as described in WO 00/08415. In fact, any suitable means for providing 3D scanning can be used so long as the 3D scan and the color 2D scan correspond substantially to the same object or portion thereof being scanned, and the same frames of references are maintained. Typically the scans are executed in relatively quick succession, and by the same or different image capturing means such as CCD's that are arranged such that the color 2D image substantially corresponds to the 3D entity. This enables color values at particular x, y coordinates of the 2D color image to be, matched to the same x, y coordinates of the 3D image which also have a z coordinate.

While four main embodiments of the present invention are now described hereinbelow, it may be appreciated that the method of the invention may be used for a very wide variety of applications in which intra oral cavity data may be obtained for use in procedures associated with the oral cavity.

Figure 14:
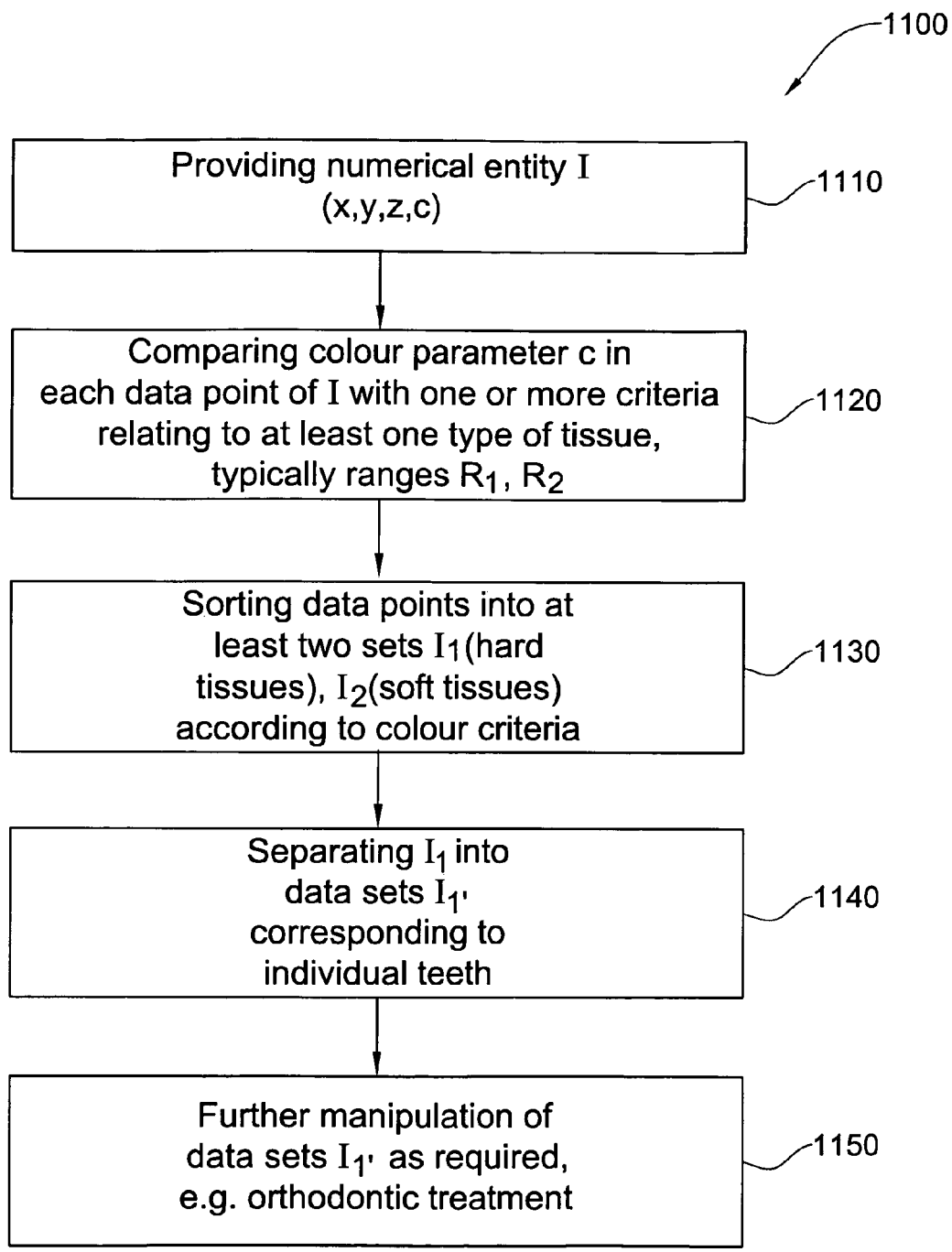
FIG. 14 illustrates the main steps of the method according to the first embodiment of the present invention.

Referring to FIG. 14, in a first embodiment of the present invention, the method of the invention, generally designated 1100, is particularly adapted for automatically differentiating one tissue from another tissue within the oral cavity. As with all embodiments of the invention, the first step 1110 is to obtain numerical entity I comprising a data set representing the surface geometry and colour of at least the portion of the intraoral cavity that contains the area of interest, herein referred to as the target surface. The target surface typically comprises both hard tissues, such as the teeth, and soft tissues which include at least one of the gums, tongue, cheeks and lips. Each data point in the numerical entity I comprises surface coordinates of the tissue, typically expressed as Cartesian (x, y, z) coordinates, plus a colour parameter relating to the colour c of the tissue at these surface coordinates. The colour value for c can be conveniently expressed in component form in terms of the red, green and blue components (RGB), and in particular in terms of a colour component coefficient. For example, a red coefficient ratio Rc, may be defined as the intensity of the red component divided by the average intensity of the red, green and blue components, and is useful in differentiating between the hard and soft tissues. The entity I may be obtained, for example, using the device described herein with respect to FIGS. 1 to 13.

In the next step 1120, the value of the colour parameter c is analysed for each data point in I, and compared with at least one colour criterion, and typically with at least two colour ranges $R_1$, $R_2$. The ranges $R_1$, $R_2$ each represent the values of the colour parameter expected for one or another of the two tissues, such as the teeth and gums. For example, the colour range $R_1$ for the teeth will include values for c typically associated with the hard tissues including the teeth, comprising all appropriate shades appropriate for enamel, dentine, pulp and other parts of teeth. Similarly, the colour range $R_2$ for the soft tissues will include values for c typically associated with gums, cheeks, lips and the tongue including all appropriate shades of pink and red associated with these tissues, including when the tissues are at least partially drained of blood, as may happen, for example when the tissues are anaesthetised. In some cases it may be appropriate to compare the value of the colour parameter c with a specific value, for example a single (R, G, B) or Rc value, rather than a range of values.

Table I lists typical RGB values measured for gums, lips and teeth of a particular patient. As may be seen from Table I, values of Rc significantly greater than unity indicate that the red component is dominant, which is the case for soft tissues in general. Hard tissues, on the other hand, have a more even distribution of colour components, resulting in an Rc value very close to unity.

TABLE I

| Intraoral RGB Values measured for a Patient | | | | |
|---|---|---|---|---|
| Tissue | Red component | Green component | Blue component | Rc = 3 * R/ (R + G + B) |
| Gum 1 | 76 | 28 | 28 | 1.6 |
| Gum 2 | 119 | 79 | 80 | 1.28 |
| Lower lip | 165 | 120 | 130 | 1.2 |
| Premolar | 168 | 175 | 167 | 0.99 |
| Incisor | 172 | 174 | 170 | 1.0 |

Thus, an exemplary range for $R_1$ may be from about 0.9 to about 1.1, while an exemplary range for $R_2$ may be from less than about 1.2 to a maximum of 3.0.

The ranges $R_1$, $R_2$ should preferably be sufficiently spaced one from the other and not overlap to facilitate distinction between the different tissues and to prevent ambiguity. At the same time, each range should include all possible variations of colour that may be expected for each of the tissues involved.

The actual values of the ranges $R_1$, $R_2$ may vary between individuals. For example, some individuals may have yellowing teeth and pale soft tissues, while others may have milky white teeth and reddish complexion. Optionally, it is possible to pre-calibrate the ranges $R_1$, $R_2$, for example by scanning an area that is purely soft tissue, and another dental area that is purely hard tissue, and using the colour values for the two scans as datum values for the two ranges $R_1$, $R_2$.

Optionally, each tissue type may also be associated with more than one range of colour values, and thus each one of $R_1$, $R_2$ may comprise a set of ranges. For example, $R_2$ may actually include four separate ranges, each relating to the colour variations of one of the gums, cheeks, lips and tongue. Also, $R_1$ may include a number of separate ranges, one range representative of the variations in the colour of natural teeth, while the other ranges relate to colours associated with prostheses and/or with fillings, particularly when made from materials which do not give a natural appearance to the prostheses, for example gold crowns or amalgam fillings.

In the next step 1130, the data points for entity I are sorted into at least two sub-data sets, $I_2$, according to the colour criteria, that is, for example, whether the value of the colour parameter of each data point is within $R_1$ or $R_2$, respectively. Thus, $I_1$ will contain all data points in which the colour parameter thereof corresponds to the colour of teeth, and thus should comprise the coordinates relating to the surfaces of teeth only within the original entity I (optionally including prostheses and fillings). Similarly, $I_2$ should contain all data points in which the colour parameter thereof corresponds to the colour of the soft tissues, and thus should comprise the coordinates relating to the soft tissues only within the original entity I.

In a modification to this embodiment, it may only be necessary or desired to identify one tissue, such as the teeth for example, and disregard all data not relating to this tissue. In such cases, it is only necessary to compare the value of the colour component of each data point to a single colour criterion, such as for example a predetermined range $R_1$ relating to the teeth only, and then separate out these data points from the entity I to provide an entity $I_1$ that comprises data relating only to the teeth. Of course, it may also be desired to include in this data set artificial teeth and also fillings that do not have a natural colour, and thus the range $R_1$ may optionally include the appropriate values for the colour parameter relating thereto.

Once the original entity I has been separated into two entities, or wherein an entity $I_1$ has been created from the original entity I comprising only the tissue of interest, the new entity may be further manipulated as desired. In step 1140, for example, when the new entity $I_1$ comprises only teeth-related data, each individual tooth may be identified therein. In such a situation, the entity $I_1$ is further separated out into a plurality of smaller entities each of which relates to a separate tooth. Typically, the separation of $I_1$ into is automatically effected using any suitable algorithm In step 1150, after the data relating to the individual teeth has been properly sorted, further manipulation may be carried out for each of the individual data sets of the entities $I_1'$, for example to simulate a particular orthodontic treatment for the teeth.

This embodiment may also be applied to the identification of a finish line profile for a crown or bridge prosthesis.

The finish line may be regarded as the circumferential junction or shoulder between the upper prepared portion of the tooth and the lower unprepared portion of the tooth. The finish line may be above or below the visible gum line, i.e. the exterior visible line of gingival tissue which circumferentially surrounds the tooth. Frequently, the finish line is below the visible gum line and is uneven, i.e. the finish line varies in height along the circumferential direction and can rise or fall on the order of several millimetres in the generally vertical direction. The finish line may even, in some cases, extend as far downwardly as the attachment line, i.e. the circumferential line defined by the neck of the tooth and its immediately adjacent gingival tissue below the aforementioned visible gum line. As with the finish line, the attachment line is uneven and also typically varies several millimetres in height along the circumferential direction. The contour of the attachment line varies from tooth to tooth, as well as from patient to patient, and is not readily visible or accessible to the dentist because it is below the visible gum line. In such cases, a retention ring or wire, made of an elastically deformable material, may be placed around the preparation to retract the gum tissue around the preparation. The ring thus in many cases exposes at least part of the emerging profile—the surface of the tooth between the finish line and the gum.

The ring thus adopts a profile which may often be substantially similar to that of the finish line. By having the ring coloured sufficiently differently to the colour of the teeth or soft tissues, say in blue, it is relatively straightforward to separate out from the entity I all data points having a colour component with a value in a specific range corresponding to the colour of the ring. Identification of the ring itself provides a useful starting point for suitable algorithms that are then applied to determine the location and geometry of the finish line. Such algorithms are known and typically attempt to identify features commonly found with finish lines such as for example, a discontinuity in the slope of the tooth surface, or a mound-shaped projection corresponding to the preparation. Moreover, separation of the hard tissue from the soft tissue results in a smaller data base that needs to be analysed to identify the finish line. In particular, when the data set has been separated into entities $I_1$, then only the specific entity $I_1$ corresponding to the ring needs to be analysed for the finish line, as this entity corresponds to the preparation.

In all variations of this embodiment, the comparison of value for the colour parameter c with an appropriate range, and the sorting of data points into one or more data sets according to this comparison can be executed with any suitable computer with the aid of a suitably constructed program. The manipulation of the entities at each stage with respect to the computer may be manual, interactive, or partially or fully automated.

Figure 15:
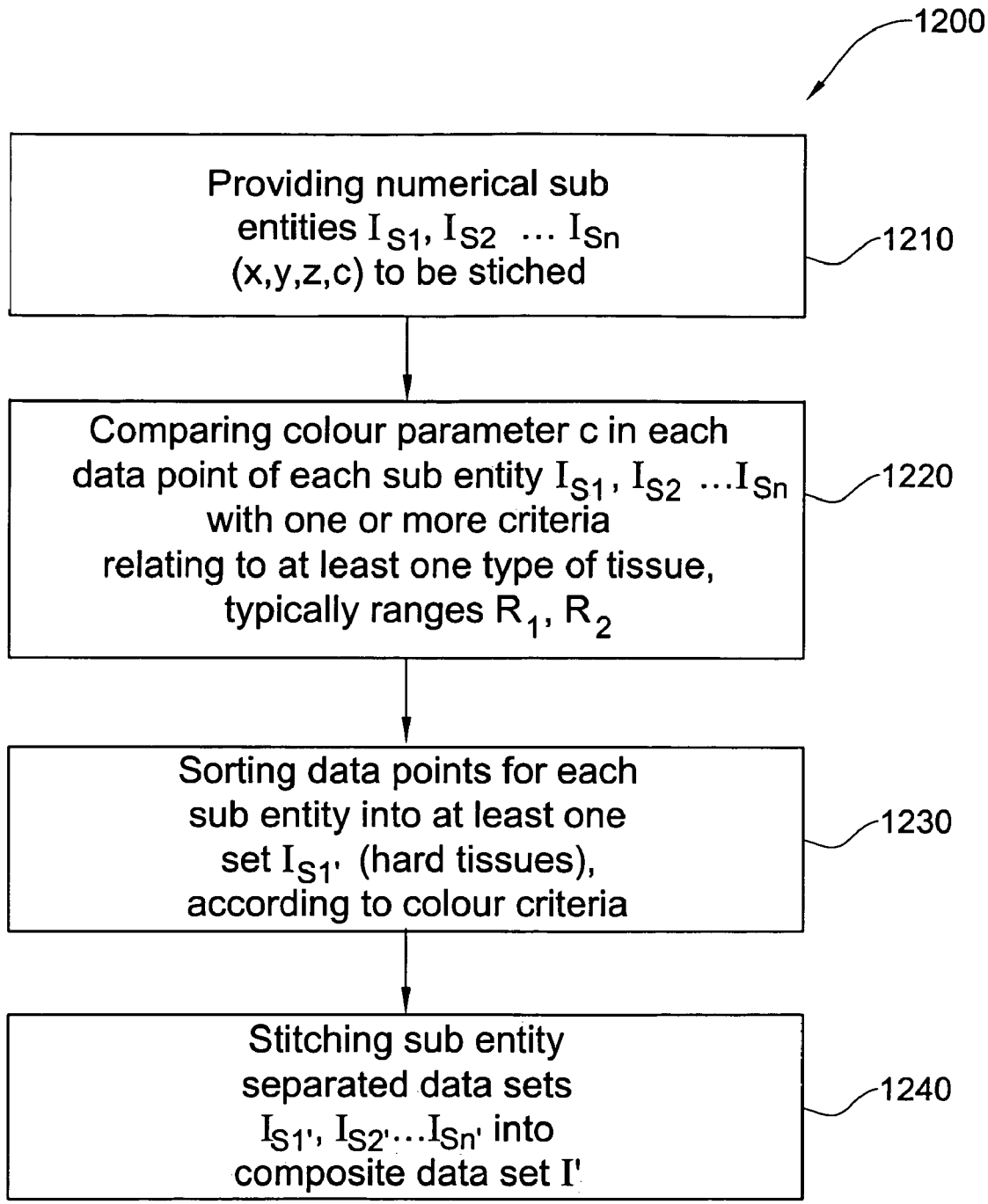
FIG. 15 illustrates the main steps of the method according to the second embodiment of the present invention.

In the second embodiment of the present invention, and referring to FIG. 15, the method, generally designated 1200, finds particular use for accurately stitching data sets of overlapping areas scanned within the intra-oral cavity. In the first step 1210, a suitable scanner, as described herein, for example, may be used for obtaining high resolution numerical sub-entities ($IS_1$, $IS_2$, ... $IS_n$) representative of the surface topography and colour of zones ($A_1$, $A_2$, ... $A_n$) within the intra-oral cavity. The zones that are scanned should together fully span the target zone of interest. Some of these zones may overlap with all the other zones, while other zones may only overlap with one or two other zones, and thus theoretically the corresponding entities should have a portion of their data identical to one another within the overlap zone. However, since the scanner itself moves in orientation and position from scan to scan, the coordinates relating to these overlap zones will usually vary between adjacent scans, even though they relate to the same spatial feature. Nevertheless, by identifying the overlap zone within the entities, the spatial relationship between the entities may be established, and the various entities stitched together or combined to form a global numerical entity that comprises the full geometry and colour representation of the target zone. The larger the overlap zone, the greater the accuracy with which the different zones may be synchronized together spatially.

In prior art methods, the overlap zones may be identified by numerically transforming the coordinates of an entity associated with one zone—by a series of translations and rotations—and in each case comparing the data set with the data set of another entity. This process is repeated until at least a portion of the data from the first entity coincides with at least a portion of the data from another entity. At this point, the data sets comprising the two sub-entities can be combined by adding both sets of coordinates, and discarding every data point that is repeated. However, some ambiguity may occur when using such a technique if a part of the intra-oral cavity (corresponding to part of the overlapping scanned data in some of the entities) moves in relation to other parts. For example, between one scan and another scan, part of the cheek may move relative to the teeth. It is then problematic to construct a composite entity comprising both scans since at least a part of the tissues (in this example the cheek) will be associated with two different data portions representative of the relative movement between scans.

In the second embodiment of the present invention, a method for stitching different data sets for the intraoral cavity is provided, in which the actual stitching technique is applied to data points corresponding to the hard tissues therein. Accordingly, in a second step 1220 of the method, the hard tissues including the teeth, fillings and prostheses are differentiated from the soft tissues including the gums, cheeks, lips and tongue. Substantially the same method as described above for first embodiment of the invention above may be utilized to identify the data, in each of the sub-entities ($IS_1$, $IS_2$, ... $IS_n$) that is associated with the hard tissues, mutatis mutandis. The data in these entities not corresponding to the hard tissues may de discarded or simply noted and set aside for future reference, thereby providing modified entities $(IS'_1, IS'_2, \ldots IS'_n)$ comprising the data of interest relating to the hard tissues, for example.

In the next step 1230 of the method, the modified entities $(IS'_1, IS'_2, \ldots IS'_n)$, are then manipulated in a similar manner in which the original entities $(I_1, I_2, \ldots I_n)$ are manipulated in the prior art, mutatis mutandis, to register and then stitch the various modified entities $(IS'_1, IS'_2, \ldots IS'_n)$ together to provide a composite entity I' that comprises the data points corresponding at least to the hard tissues.

As an optional step, the data referring to the soft tissues may then be added to the composite entity I' as follows. Referring to the soft tissue data corresponding to each scan as entities $(IS''_1, IS''_2, \ldots IS''_n)$, each one of these entities is first manipulated in precisely the same manner as the corresponding entity of the group of modified entities $(IS'_1,$ was manipulated in order to stitch the latter together into I'. After this, the coordinates of each pair of entities within the group $(IS''_1, IS''_2, \ldots IS''_n)$ are compared in turn. Each pair of entities within the group $(IS''_1, IS''_2, \ldots IS''_n)$ is checked to determine whether there exist some data points in one entity having two coordinates, say (x, y) identical to corresponding data points in the other entity, but in which the (z) coordinates are different. All such data points in either one or the other entity are then disregarded. In this manner, a composite entity I" can be constructed for the soft tissues, which can then be added to, if desired to the composite entity I' of the hard tissues previously created.

Typically, course stitching of the original sub entities $(IS_1, IS_2, \ldots IS_n)$ is first carried out, and when the approximate relationships between the sub entities is known, a next step is performed, comprising fine stitching the corresponding separated hard-tissue sub entities $(IS'_1, IS'_2, \ldots IS'_n)$.

Figure 16:
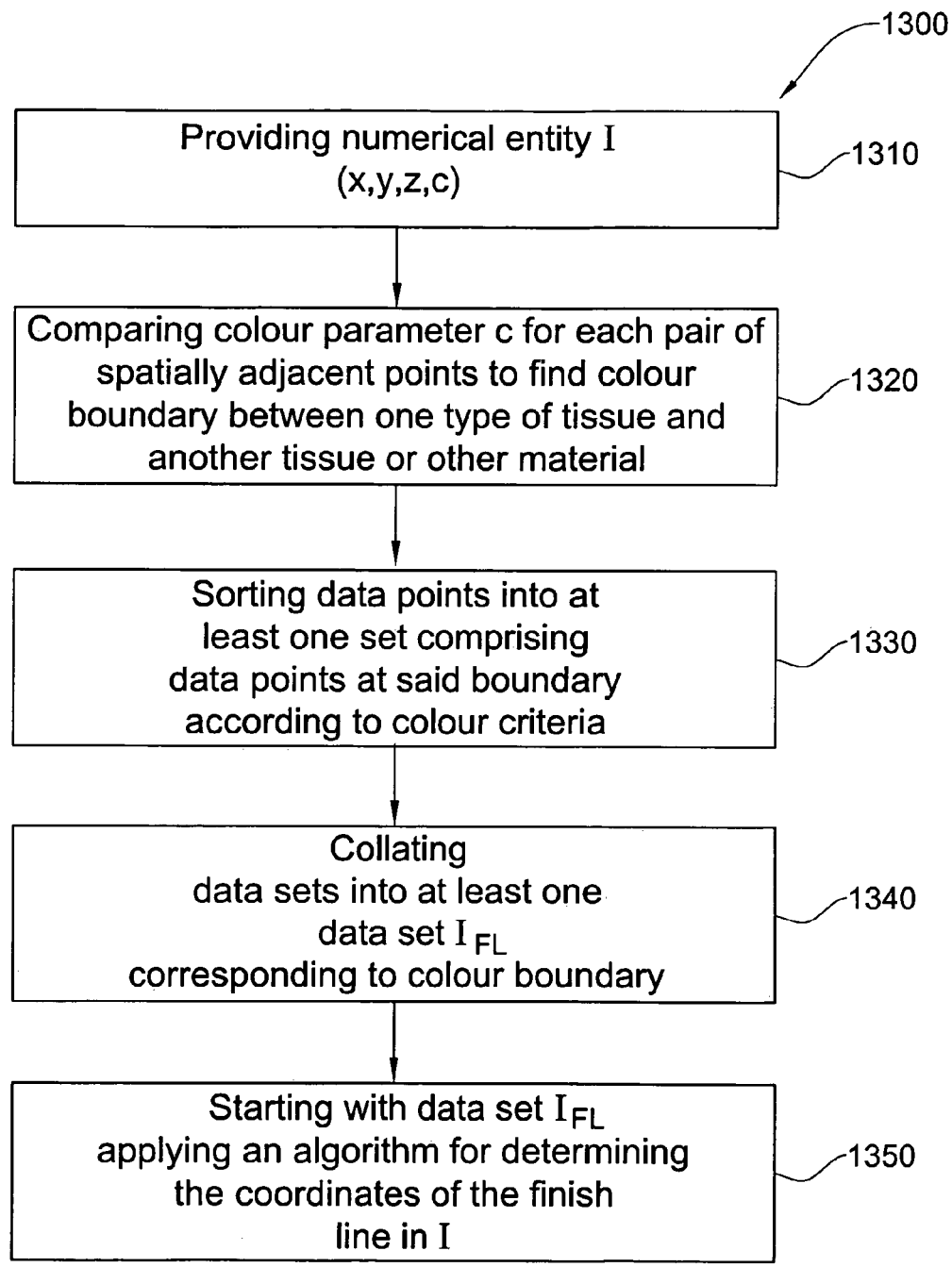
FIG. 16 illustrates the main steps of the method according to the third embodiment of the present invention.

In the third embodiment of the present invention, and referring to FIG. 16, the method, generally designated 1300, is used for automatically defining the finish line of a preparation. As described above, the finish line may be regarded as the circumferential junction or shoulder between the upper prepared portion of the tooth and the lower unprepared portion of the tooth. The finish line may be above or below the visible gum line, i.e. the exterior visible line of gingival tissue which circumferentially surrounds the tooth. In cases where the finish line protrudes from the gum, the complete circumferential extent of the finish line is visible and appears as a shade of white. This may be contrasted with the pink/red colour of the surrounding gums, and at the same time the finish line is assumed to be in close proximity to the gums. In such a case, the method of the invention according to the third embodiment is carried out as follows.

As with other embodiments, the first step 1310 is to provide a numerical entity I that describes the target area—in this case the part of the intraoral cavity that comprises the finish line—geometrically and with respect to colour. Preferably, the target area is confined to the tooth having the preparation, and possibly the adjacent teeth. Then, in step 1320, an algorithm is applied to every pair of spatially adjacent data points, for example, wherein the value of the colour parameter c of each of these points are compared one with the other, or with respect to some colour criteria. When it is determined that the difference in colour values is greater than a predetermined threshold, it is then assumed that the pair of data points are on opposite sides of a boundary between two tissues of different colour, in particular between the edge of the tooth and the gum. Alternatively, the value of parameter c is compared with two predetermined ranges, $R_1, R_2$, wherein each range corresponds to a colour associated with one or the other of teeth and gums. Then, wherever there is a pair of adjacent data points in which one data point has a value for parameter c within $R_1$ and the other data point has a value for parameter c within $R_2$, once again these two data points are considered to be on either side of the boundary between a tooth and the gum. The process is repeated for each adjacent pair of points in the entity I, thereby providing in step 1330 another numerical entity $I_{FL}$ representative of the gum line and comprising topographic (as well as colour) information relating thereto.

Identification of the gum line itself provides a useful starting point for suitable algorithms that are then applied in step 1340 to determine the location and geometry of the finish line. Such algorithms typically attempt to identify features commonly found with finish lines, as has been described herein for the first embodiment. Thus, the algorithm is applied to the entity I, but staring with the surface data thereof corresponding to entity $I_{FL}$.

In cases where the finish line is partially or fully located below the gum, a suitable ring may be placed between the neck of the tooth preparation and the gum such as to retract the latter and expose the finish line. The method according to the third embodiment may then be applied with a modification in that the boundary between the tooth material and the ring material is searched for, in a similar manner to that described regarding the boundary between the tooth material and gum, mutatis mutandis, which provides a starting point for algorithms that are then applied to identify the finish line.

Preferably, where the entity I is viewable as a two dimensional colour image on a screen, the method optionally further comprises the step of displaying on such an image of the entity I the finish line entity $I_{FL}$, preferably in a colour having high contrast with respect to I, to enable the practitioner to check the result.

The method according to this embodiment may be modified to separate the soft tissues from the hard tissues, once the demarcation line between the two tissues is known, as determined above.

Figure 17:
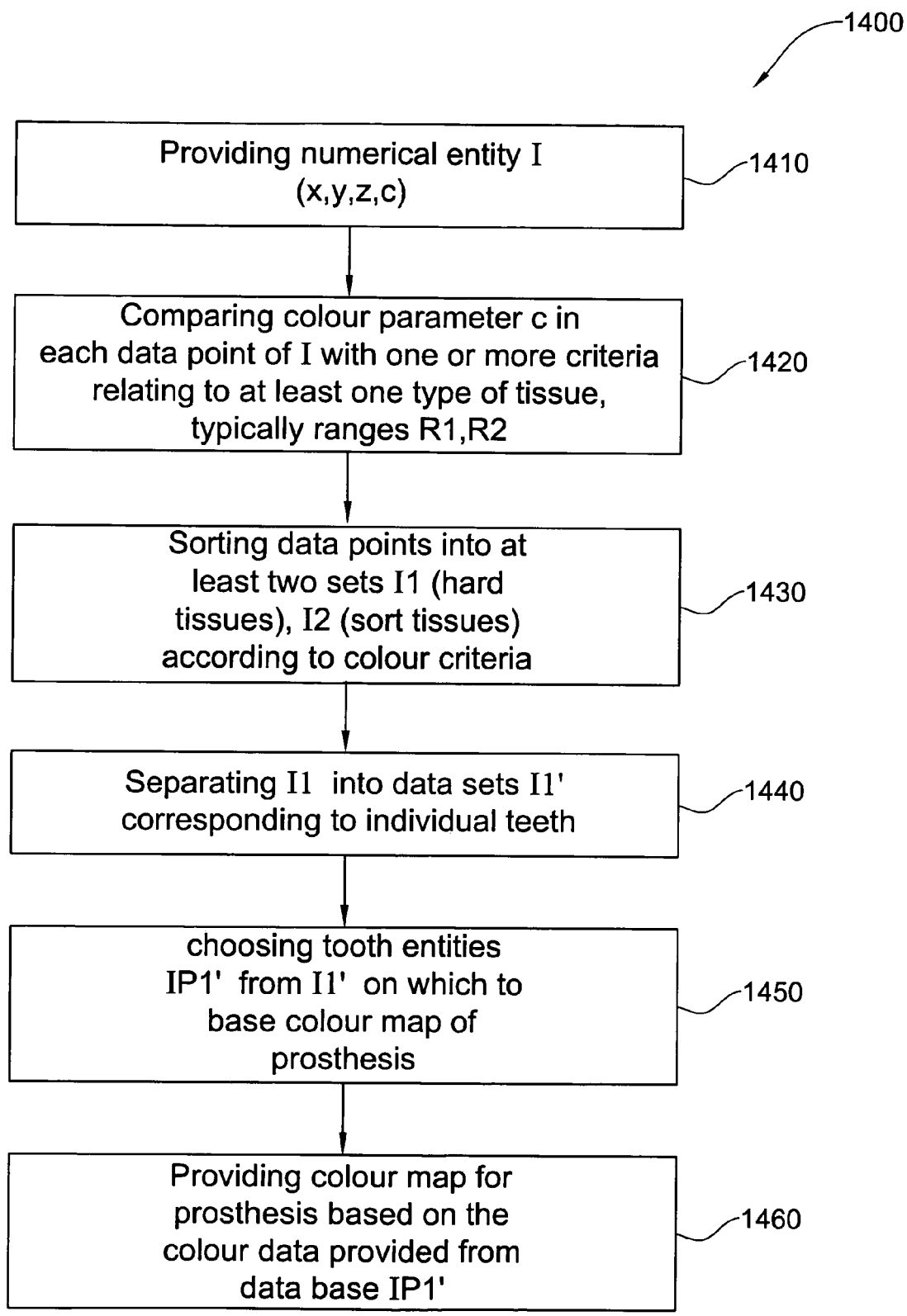
FIG. 17 illustrates the main steps of the method according to the fourth embodiment of the present invention.
Figure 18:
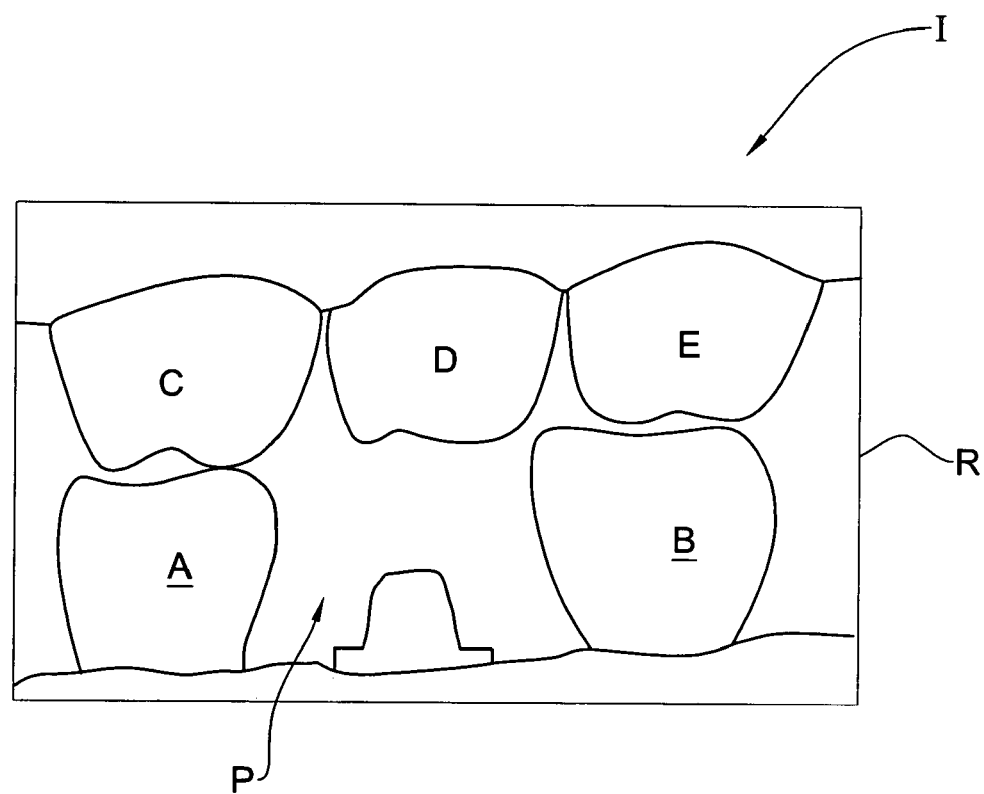
FIG. 18 illustrates a portion of the intraoral cavity on which it is desired to implant a dental prosthesis.

In the fourth embodiment of the invention, and referring to FIG. 17, the method, generally designated 1400, is particularly applied to the shading of a prosthesis. As with the other embodiments of the invention, the first step 1410 involves the creation of a numerical entity I of the region of interest within the oral cavity. Referring to FIG. 18, in this case, the region of interest R includes the preparation area P of the intraoral cavity in which the prosthesis is to be mounted, including adjacent teeth thereto, A, B as well as the teeth C, D, E opposite thereto on the opposing jaw. The region of interest R may optionally or alternatively include at least one tooth or teeth on the other side of the same jaw corresponding to the tooth or teeth that the prosthesis is designed to replace. The desired data in this embodiment that it is desired to create from the entity I relates to shading information for the prosthesis such as to provide a natural-looking appearance thereto that is compatible with the other teeth of the patient. The shading characteristics of the prosthesis according to the invention are to be based on the shading characteristics of at least one tooth of the patient, and thus share the same colour, variations in hue and other features such as reflective qualities and translucency, that may be found on one or more teeth of the patient, according to any desired set of rules or algorithm.

In the next steps 1420, 1430, 1440, the entity I is manipulated such as to extract the data corresponding to the teeth only, and to separate this data into a set of discrete entities each of which represents an individual teeth, substantially as described regarding steps 1120, 1130 and 1140, respectively, for the first embodiment herein, mutatis mutandis.

Then, in step 1450, the decision is taken regarding which teeth are to be considered for modelling the shading of the prosthesis thereon. This decision may be made automatically, for example including only the adjacent teeth A, B, or the tooth D directly opposite the preparation area P, or any other appropriate tooth or combination of teeth. A suitable algorithm may be provided that recognizes which entity in $I_{1'}$ corresponds to the area P, for example by determining the height of each tooth entity, and working out the entity having the shortest height. The height of each tooth may be obtained from the corresponding entity $I_{1'}I_F$ by suitable algorithms and routines, as known in the art. The spatial relationship between the entity corresponding to the area P and the entities corresponding to the other teeth can then be determined in an automated manner by using simple geometrical rules.

Alternatively, the choice may be made manually, and this may be done, for example, by displaying the scanned and separated teeth entities on a suitable display, such as a computer screen for example, and then marking the desired tooth or teeth by means of a cursor or the like. It may be preferable to manually perform this selection, as it would be important not to include certain teeth with particular visual defects or irregularities, e.g. cavities, parts that require restorations, spots that need to be removed etc. that it is not wished to repeat in the prosthesis.

The data sets $I_{P1'}$, corresponding to the chosen teeth are then analysed in turn, and in step 1460 a color map for the prosthesis is provided based on the colour data provided from data base $I_{P1}'$.

Figure 19:
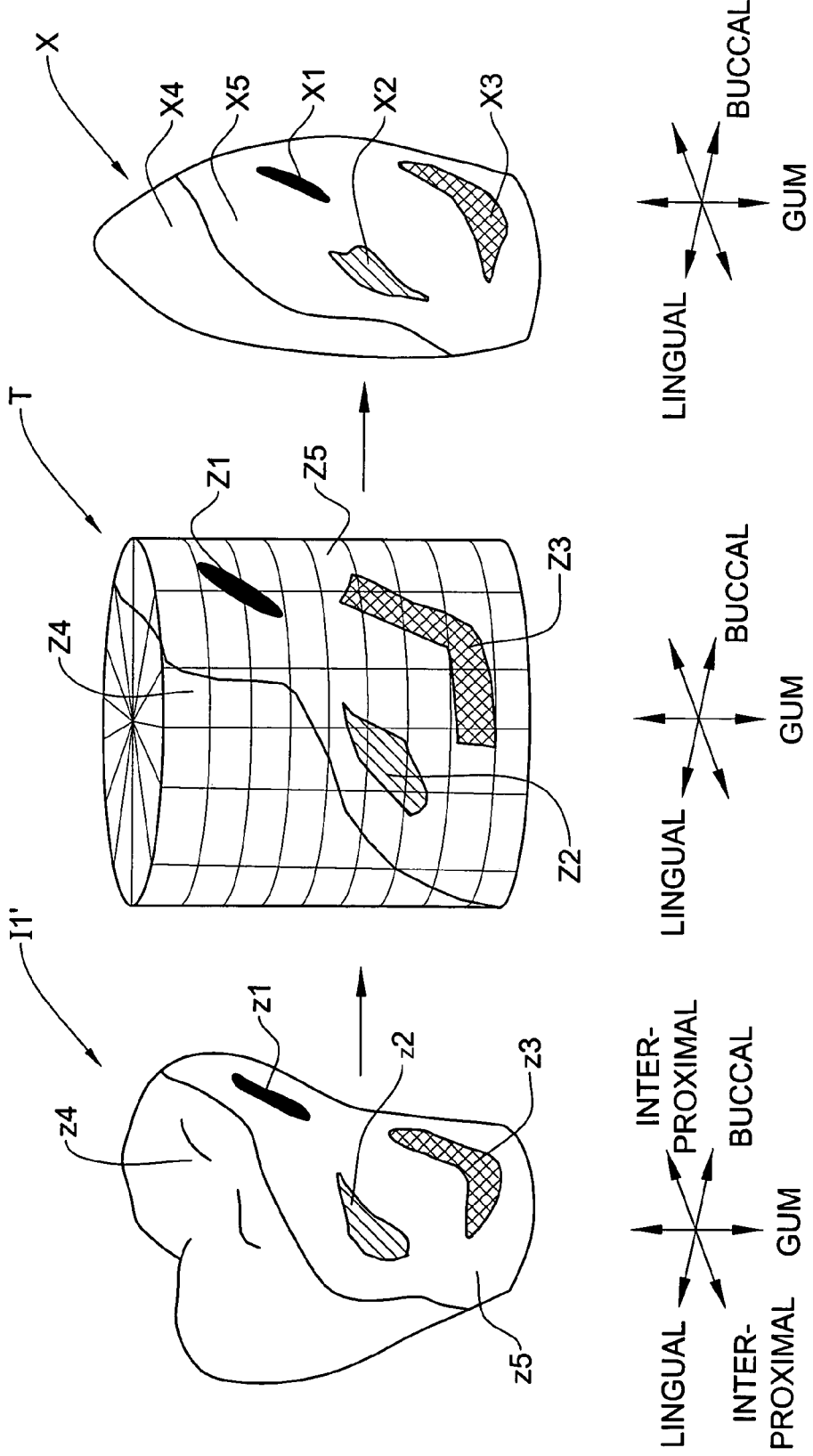
FIG. 19 schematically illustrates a transformation step according to the method of FIG. 17.

Referring to FIG. 19, for each of the teeth chosen, the appropriate entities are each geometrically transformed to conform to a predetermined geometrical shape, for the sake of example illustrated in this figure as a cylinder, to provide a transformed entity T. In the transformation process, the surface geometry of $I_{P1'}$ is transformed into the surface geometry of T, and the values of the colour parameters c associated with every data point are correspondingly transferred. Effectively, then, the colour attributes of each individual entity $I_{1'}$, such as for example features z1, z2, z3, and the two differently coloured zones z4, z5 exemplified in FIG. 19, are thus mapped onto the entity T into areas Z1, Z2, Z3, Z4 and Z5 respectively.

When only one tooth is chosen for basing the shading of the prosthesis on, i.e., corresponding to only a single entity $I_{P1'}$, the transformed entity T thus obtained is then transformed again to assume the shape of the prosthesis, providing a prosthesis entity X, effectively mapping all the colour features of the entity $I_{P1'}$ thereto. The shape of the prosthesis is previously determined by any suitable means, and this does not form part of the present invention. The entity X thus comprises the surface geometry of the prosthesis, and the shading information with respect to this geometry, including features x1-x5 transferred from features Z1-Z5 respectively, that will provide a similar appearance to that of the tooth on which the colour was modelled. In such a case, the intermediate step of transforming $I_{P1'}$ to T may be dispensed with, and thus the entity $I_{P1'}$ may be transformed directly into the form of the crown prosthesis, thereby providing the values for the colour c thereof.

Nevertheless, the inclusion of intermediate entity T may be useful.

Optionally, the tooth may be divided into three general zones: a gingival zone close to the gums, an intermediate body zone, and an incisal zone comprising the cusp of the tooth. The colours can be mapped into each of the zones independently, and then smoothed out between the zones to avoid sharp discontinuities in colour.

When a number of teeth are chosen to serve as the basis for shading the prosthesis, the entities $I_{1'}$ corresponding to each of these teeth is transformed to a corresponding entity T'. Then, the colour data of the entities T' are combined to provide a composite entity T of the same shape but having composite shading information obtained from all the entities $I_{1'}$. For example the colour value at every geometrical point for all the entities T' could be averaged. Alternatively, a weighted average of the colours could be provided, wherein more weight is given to teeth that are closest in location and/or function than to other teeth. Again, when such a combination of the colour information is effected, it is important to ensure that the various entities T' are aligned with respect to the individual interproximal, buccal and lingual sides. The composite entity T is then transformed geometrically to conform to the shape of the prosthesis to provide entity X as described before, but wherein the composite colour values for parameter c are now transferred to the geometrical shape of the entity.

In the above example, the prosthesis has been exemplified as a crown. Nevertheless, the method may be applied to a bridge prosthesis, filing, restoration, or tooth transplant in a similar manner to that described, mutatis mutandis.

While the above embodiments have been described as operations carried out on discrete data points, it is clear that the method of the invention is applicable to similar operations being carried out on new data points suitably interpolated with respect to the original data points, mutatis mutandis. Furthermore, it is also possible to carry out the method of the invention when the numerical entity is structured in a different manner to that described herein, mutatis mutandis. For example, rather than being described as a series of discrete data points on a surface, the surface of the intra-oral cavity could be described as a series of segments, by suitable formulae, or by any other geometric modelling method.

Figure 20:
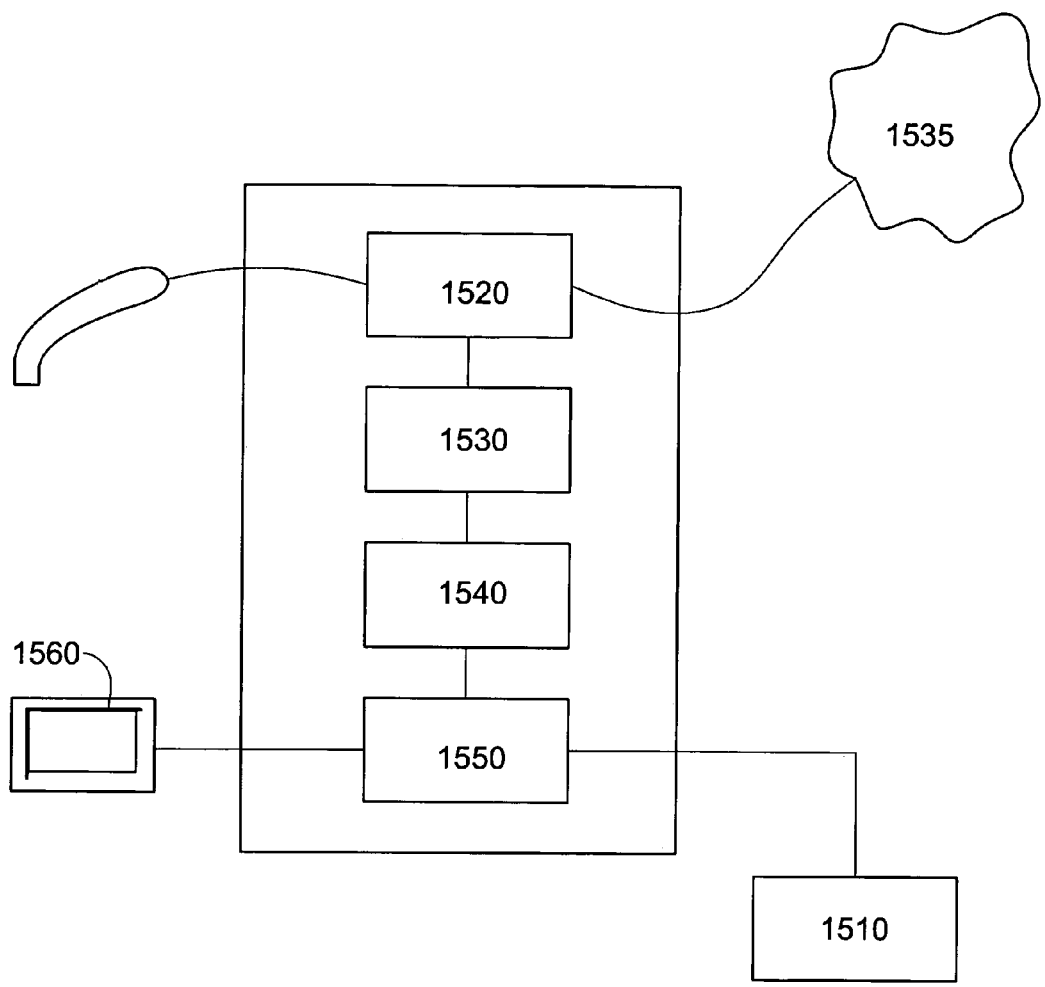
FIG. 20 is a block diagram of a system according to an embodiment of the present invention.

FIG. 20 is a block diagram of a system 1500 according to an embodiment of the present invention. System 1500 presents a software/hardware utility connectable to a virtual treatment system 1510, for example. System 1500 comprises such main elements as follows:

- an input utility 1520 for receiving data indicative of three dimensional colour data of the intraoral cavity, obtained directly using scanner 1525 (for example the device 100 described herein in reference to FIGS. 1 to 13) or obtained elsewhere and transmitted to the input facility via any communication medium 1535, including for example the internet, an intranet, and so on;
- a memory utility 1530 for storing the data;
- a processor utility 1540 for manipulating said first data set to provide desired data therefrom, particularly using any algorithm according to the present method; and
- output utility 1550.

System 1500 can be connected to a display 1560 or a printer (not shown) for visually presenting the manipulated entities. System 1500 can be also connectable to an additional utility such as a virtual treatment system 1510.

In another aspect of the present invention, a computer readable medium is provided that embodies in a tangible manner a program executable for providing data useful in procedures associated with the oral cavity. The computer readable medium comprises:

(a) a first set of data representative of the three dimensional surface geometry and colour of at least part of the intra oral cavity;

(b) means for manipulating said first data set to provide desired data therefrom.

The medium may comprise, for example, optical discs, magnetic discs, magnetic tapes, and so on.

The embodiments illustrated herein are particularly useful for determining the three-dimensional structure of a teeth segment, particularly a teeth segment where at least one tooth or portion of tooth is missing for the purpose of generating data of such a segment for subsequent use in design or manufacture of a prosthesis of the missing at least one tooth or portion, e.g. a crown, or a bridge, or a dental restoration or a filing. It should however be noted, that the invention is not limited to this embodiment, and applies, mutatis mutandis, also to a variety of other applications of imaging of three-dimensional structure of objects, e.g. for the recordal or archeological objects, for imaging of a three-dimensional structure of any of a variety of biological tissues, etc.

While there has been shown and disclosed exemplary embodiments in accordance with the invention, it will be appreciated that many changes may be made therein without departing from the spirit of the invention.

In the method claims that follow, alphabetic characters and Roman numerals used to designate claim steps are provided for convenience only and do not imply any particular order of performing the steps.

Finally, it should be noted that the word "comprising" as used throughout the appended claims is to be interpreted to mean "including but not limited to".

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for generating a 3D model of an intraoral structure portion, the system comprising:
    a hand-held imaging device comprising a probe, focusing optics configured to scan a focal plane of the hand-held imaging device over a range of depths, an illuminator, and an image sensor configured to capture data of light returning from an intraoral structure portion over the range of depths of the intraoral structure portion, wherein the data includes depth data captured in response to illuminating the intraoral structure portion with light of a first wavelength and image data captured in response to illuminating the intraoral structure portion with light of a second wavelength, wherein light from the illuminator and light returning from the intraoral structure portion pass through the focusing optics; and
    one or more processors operably coupled to the hand-held imaging device, the one or more processors configured to cause the system to:
        receive at least two numerical entities representative of the intraoral structure portion and comprising the depth data and the image data;
        differentiate between depth data representing hard tissue of the intraoral structure portion and depth data representing soft tissue of the intraoral structure portion based on the image data;
        stitch the at least two numerical entities together based on a weighted registration of the depth data, the weight being based on the differentiation between the depth data representing the hard tissue and the depth data representing the soft tissue.

2. The system of claim 1, wherein the at least two numerical entities comprise surface data of the intraoral structure portion.

3. The system of claim 1, wherein the illuminator emits light of the first wavelength and depth data comprises light of the first wavelength returning from the intraoral structure portion.

4. The system of claim 3, wherein the light of the first wavelength returning from the intraoral structure portion is reflected from the intraoral structure portion.

5. The system of claim 1, wherein the image data includes color data points.

6. The system of claim 5, wherein the differentiation between the hard tissue and the soft tissue is based on the color data points.

7. The system of claim 6, wherein the weighted registration comprises only registration of the depth data representing the hard tissue.

8. The system of claim 6, wherein the differentiation between the depth data comprises comparing the color data points within the image data to at least one color criterion and the one or more processors are further configured to cause the system to associate each of a plurality of corresponding depth data points with either the hard tissue or the soft tissue based on the comparison.

9. The system of claim 6, wherein the one or more processors are further configured to cause the system to determine a color coefficient for each data point in the image data.

10. The system of claim 9, wherein the differentiation between the depth data comprises comparing the color coefficient for each data point in the image data to at least one color criterion and the one or more processors are further configured to cause the system to associate each of the plurality of corresponding depth data points with either the hard tissue or the soft tissue based on the comparison.

11. The system of claim 1, wherein the differentiation between the hard tissue and the soft tissue also includes differentiation between types of soft tissue.

12. A method for generating a 3D model of an intraoral structure, the method comprising:
    illuminating the intraoral structure with a first light source;
    capturing a plurality of depth image data sets during the illumination with the first light source;
    illuminating the intraoral structure with a second light source;
    capturing a plurality of two-dimensional image data sets during the illumination with the second light source;
    differentiating between hard tissue in the plurality of depth image data sets and soft tissue in the plurality of depth image data sets based on the plurality of two-dimensional image data sets; and
    stitching the plurality of depth image data sets together based on the differentiation between the hard tissue and the soft tissue.

13. The method of claim 12, wherein the plurality of depth image data sets comprise surface data of the intraoral structure.

14. The method of claim 12, wherein the plurality of depth image data sets comprise light of the first light source returning from the intraoral structure.

15. The method of claim 14, wherein the plurality of two-dimensional image data sets comprise light of a first wavelength from the intraoral structure.

16. The method of claim 12, wherein the stitching of the plurality of depth image data sets comprises a weighted registration of data points of the plurality of depth image data sets, the weighted registration based on the differentiation between the hard tissue and the soft tissue.

17. The method of claim 16, wherein the weighted registration comprises only registration of the data points of the plurality of depth image data sets representing the hard tissue.

18. A system for determining surface characteristics of an intraoral structure portion, the system comprising:
- a hand-held imaging device comprising a probe, focusing optics configured to scan a focal plane of the hand-held imaging device over a range of depths, a first light source, a second light source, and an image sensor configured to capture depth image data of light returning from an intraoral structure portion over the range of depths in response to illuminating the intraoral structure portion with the first light source and capture two-dimensional image data in response to illuminating the intraoral structure portion with the second light source, wherein light from the first light source and light returning from the intraoral structure portion pass through the focusing optics; and
- one or more processors operably coupled to the hand-held imaging device, the one or more processors configured to cause the system to:
- receive a plurality of depth image data sets comprising light of a first wavelength;
- receive a plurality of two-dimensional image data sets comprising light of a second wavelength;
- differentiate between hard tissue in the plurality of depth image data sets and soft tissue in the plurality of depth image data sets based on the plurality of two-dimensional image data sets; and
- stitch the plurality of depth image data sets together based on the differentiation between the hard tissue and the soft tissue.

19. The system of claim 18, wherein the plurality of depth image data sets comprise a plurality of data points, each data point comprising three-dimensional surface coordinate data associated therewith.

20. The system of claim 18, wherein the image sensor is a color image sensor.

21. The system of claim 18, wherein the differentiation between the hard tissue in the plurality of depth image data sets and the soft tissue in the plurality of depth image data sets based on the plurality of two-dimensional image data sets comprise comparing color data points within the plurality of two-dimensional image data sets to at least one color criterion and the one or more processors are further configured to cause the system to associate each of a plurality of corresponding depth data points with either hard tissue or soft tissue based on the comparison.

22. The system of claim 18, wherein the two-dimensional image data is color image data.

23. The system of claim 18, wherein the depth image data is surface data of the intraoral structure portion.

24. The system of claim 18, wherein the first light source emits light of at least the first wavelength and the plurality of depth image data sets comprise light of the first wavelength returning from the intraoral structure portion.

25. The system of claim 24, wherein the light of the first wavelength returning from the intraoral structure portion is reflected from the intraoral structure portion.

26. The system of claim 18, wherein the one or more processors are further configured to cause the system to determine a color coefficient for each data point in the depth image data based on the two-dimensional image data; and
- wherein the differentiation between hard tissue and soft tissue in the depth image data comprises comparing the color coefficient for each data point in the depth image data to at least one color criterion and the one or more processors are further configured to cause the system to associate each of a plurality of corresponding depth image data points with either hard tissue or soft tissue based on the comparison.

27. The system of claim 18, wherein the focusing optics, the first light source, the second light source, and the image sensor are configured to:
- sequentially illuminate the intraoral structure portion with each of a plurality of wavelengths of emitted light; and
- capture the plurality of depth image data sets and the plurality of two-dimensional image data sets during the sequential illumination of the intraoral structure portion, each of the plurality of depth image data sets and the plurality of two-dimensional image data sets being captured during emission of a respective one of the plurality of wavelengths.

28. The system of claim 27, wherein the plurality of wavelengths includes the first and second wavelengths.

29. The system of claim 28, wherein the image sensor is a color image sensor.

* * * * *